(12) United States Patent
Skog et al.

(10) Patent No.: US 11,427,864 B2
(45) Date of Patent: Aug. 30, 2022

(54) METHODS AND COMPOSITIONS TO DETECT MUTATIONS IN PLASMA USING EXOSOMAL RNA AND CELL FREE DNA FROM NON-SMALL CELL LUNG CANCER PATIENTS

(71) Applicant: Exosome Diagnostics, Inc., Waltham, MA (US)

(72) Inventors: Johan Karl Olov Skog, Lincoln, MA (US); Elena Castellanos-Rizaldos, Waltham, MA (US); Vasisht Tadigotla, Newton, MA (US); Dominik Grimm, Schondorf am Ammersee (DE); Xuan Zhang, North Reading, MA (US); Wei Yu, Belmont, MA (US)

(73) Assignee: Exosome Diagnostics, Inc., Waltham, MA (US)

( * ) Notice: Subject to any disclaimer, the term of this patent is extended or adjusted under 35 U.S.C. 154(b) by 258 days.

(21) Appl. No.: 16/463,820

(22) PCT Filed: Nov. 17, 2017

(86) PCT No.: PCT/US2017/062370
§ 371 (c)(1),
(2) Date: May 23, 2019

(87) PCT Pub. No.: WO2018/102162
PCT Pub. Date: Jun. 7, 2018

(65) Prior Publication Data
US 2019/0376128 A1 Dec. 12, 2019

Related U.S. Application Data

(60) Provisional application No. 62/428,059, filed on Nov. 30, 2016.

(51) Int. Cl.
| | | |
|---|---|---|
| *C12P 19/34* | (2006.01) | |
| *C12Q 1/6851* | (2018.01) | |
| *C12Q 1/6886* | (2018.01) | |

(52) U.S. Cl.
CPC ......... *C12Q 1/6851* (2013.01); *C12Q 1/6886* (2013.01); *C12Q 2600/106* (2013.01); *C12Q 2600/118* (2013.01); *C12Q 2600/156* (2013.01); *C12Q 2600/16* (2013.01)

(58) Field of Classification Search
CPC .............................. C12Q 1/6851; C12Q 1/6886
See application file for complete search history.

(56) References Cited

U.S. PATENT DOCUMENTS

| | | |
|---|---|---|
| 5,219,727 A | 6/1993 | Wang et al. |
| 5,538,871 A | 7/1996 | Nuovo et al. |
| 5,556,773 A | 9/1996 | Yourno |
| 5,639,606 A | 6/1997 | Willey |
| 5,639,611 A | 6/1997 | Wallace et al. |
| 6,004,755 A | 12/1999 | Wang |
| 6,812,023 B1 | 11/2004 | Lamparski et al. |
| 6,893,837 B2 | 5/2005 | Slamon et al. |
| 6,899,863 B1 | 5/2005 | Dhellin et al. |
| 6,913,879 B1 | 7/2005 | Shena |
| 6,994,960 B1 | 2/2006 | Foote et al. |
| 7,074,563 B2 | 7/2006 | Köster |
| 7,198,893 B1 | 4/2007 | Köster et al. |
| 7,198,923 B1 | 4/2007 | Abrignani et al. |
| 7,186,512 B2 | 5/2007 | Martienssen et al. |
| 7,364,848 B2 | 4/2008 | Van Beuningen et al. |
| 7,378,245 B2 | 5/2008 | Liu |
| 2009/0104120 A1* | 4/2009 | Chinnaiyan ............. A61P 35/00 424/9.2 |
| 2010/0196426 A1* | 8/2010 | Skog ....................... A61P 35/00 424/400 |
| 2011/0028498 A1* | 2/2011 | Ryan .................... C12Q 1/6886 514/266.21 |
| 2014/0038901 A1* | 2/2014 | Lyden .................. C12Q 1/6886 514/19.8 |
| 2014/0296081 A1* | 10/2014 | Diehn .................. C12Q 1/6806 506/2 |

(Continued)

FOREIGN PATENT DOCUMENTS

| | | |
|---|---|---|
| WO | WO 00/71562 A1 | 11/2000 |
| WO | WO 2003/023065 A1 | 3/2003 |

(Continued)

OTHER PUBLICATIONS https://clinicaltrials.gov/ct2/show/NCT02151981, ClinicalTrials.gov Identifier: NCT02151981, First Posted: Jun. 2, 2014, Results First Posted: Jul. 21, 2017, Last Update Posted: Feb. 18, 2020, 10 pages.
http://www.ncbi.nlm.nih.gov/projects/SNP/snp_ref.cgi?rs=1050171, Reference SNP (rs) Report 1050171, released Jul. 9, 2019, 8 pages.
https://www.accessdata.fda.gov/cdrh_docs/pdf16/p160045b.pdf, PMA P160045: FDA Summary of Safety and Effectiveness Data, Nov. 8, 2017, 52 pages.
https://www.accessdata.fda.gov/cdrh_docs/pdf15/p150044b.pdf, PMA P150044: FDA Summary of Safety and Effectiveness Data, Dec. 15, 2015, 30 pages.
Abravaya, K. et al., "Detection of point mutations with a modified ligase chain reaction (Gap-LCR)," Nucleic Acids Research, 23(4):675-682 (1995).

(Continued)

*Primary Examiner* — Kenneth R Horlick
(74) *Attorney, Agent, or Firm* — Cooley LLP; Ivor R. Elrifi; Matthew Pavao

(57) ABSTRACT

The present invention relates generally to methods and kits for detecting one or more biomarkers, such as an Epidermal Growth Factor Receptor (EGFR) mutation, e.g., T790M mutation, L858R mutation, one or more exon19 insertions and/or one or more exon19 deletions in the EGFR gene, in a biological sample to aid in diagnosis, prognosis, monitoring, or therapy selection for a disease such as, for example, cancer. The methods and kits are useful in aiding in diagnosis, prognosis, monitoring, or therapy selection for lung cancer, e.g., non-small cell lung cancer (NSCLC).

12 Claims, 9 Drawing Sheets
Specification includes a Sequence Listing.

(56) References Cited

U.S. PATENT DOCUMENTS

| | | | |
|---|---|---|---|
| 2015/0132256 A1* | 5/2015 | Janku | C12Q 1/6883 424/85.2 |
| 2016/0258021 A1* | 9/2016 | Falk | C12Q 1/6883 |
| 2017/0175200 A1* | 6/2017 | Lyden | C12Q 1/6806 |
| 2019/0376128 A1 | 12/2019 | Skog et al. | |

FOREIGN PATENT DOCUMENTS

| | | |
|---|---|---|
| WO | WO 2006/113590 A2 | 10/2006 |
| WO | WO 2014/107571 A2 | 7/2014 |
| WO | WO 2014/193999 A2 | 12/2014 |
| WO | WO 2016/007755 A1 | 1/2016 |
| WO | WO 2018/102162 A1 | 6/2018 |

OTHER PUBLICATIONS

Altschul, S. F. et al., "Basic Local Alignment Search Tool," J. Mol. Biol., 215:403-410 (1990).

Altschul, S. F. et al., "Gapped BLAST and PSI-BLAST: a new generation of protein database search programs," Nucleic Acids Research, 25(17):3389-3402 (1997).

Canchola, J. A. et al., "Limit of Detection (LoD) Estimation Using Parametric Curve Fitting to (Hit) Rate Data: The LoD_Est SAS® Macro," SAS Macros: Analytical Sensitivity Estimation, Jan. 2016, 10 pages; doi:10.13140/RG.2.1.4799.4969.

Chen, C. et al., Microfluidic isolation and transcriptome analysis of serum microvesicles, Lab Chip., 10(4):505-511 (2010).

Cheruvanky, A. et al., "Rapid isolation of urinary exosomal biomarkers using a nanomembrane ultrafiltration concentrator," Am J Physiol Renal Physiol, 292:F1657-F1661 (2007).

Cotton, R. G. H. et al., "Reactivity of cytosine and thymine in single-base-pair mismatches with hydroxylamine and osmium tetroxide and its application to the study of mutations," Proc. Natl. Acad. Sci., 85:4397-4401 (1988).

Fukuoka, M. et al., "Biomarker Analyses and Final Overall Survival Results From a Phase III, Randomized, Open-Label, First-Line Study of Gefitinib Versus arboplatin/Paclitaxel in Clinically Selected Patients With Advanced Non-Small-Cell Lung Cancer in Asia (IPASS)," Journal of Clinical Oncology, 29(21):2866-2874 (2011).

Gazdar, A. F., "Activating and resistance mutations of EGFR in non-small-cell lung cancer: role in clinical response to EGFR tyrosine kinase inhibitors," Oncogene, 28: S24-S31 (2009).

Guatelli, J. C. et al., Isothermal, in vitro amplification of nucleic acids by a multienzyme reaction modeled after retroviral replication, Proc. Natl. Acad. Sci. USA, 87:1874-1878 (1990).

Hahn, P. J., "Molecular Biology of Double-Minute Chromosomes," BioEssays, 15(7):477-484 (1993).

Isobe, K. et al., "Clinical Significance of BIM Deletion Polymorphism in Non-Small-Cell Lung Cancer with Epidermal Growth Factor Receptor Mutation," J Thorac Oncol., 9:483-487 (2014).

Karlovich, C. et al., "Assessment of EGFR Mutation Status in Matched Plasma and Tumor Tissue of NSCLC Patients from a Phase I Study of Rociletinib (CO-1686)," Clin Cancer Res, 22:2386-2395 (2016).

Kutyavin, I. V., "Use of Base-Modified Duplex-Stabilizing Deoxynucleoside 5'-Triphosphates To Enhance the Hybridization Properties of Primers and Probes in Detection Polymerase Chain Reaction," Biochemistry, 47:13666-13673 (2008).

Kwoh, D. Y. et al., "Transcription-based amplification system and detection of amplified human immunodeficiency virus type 1 with a bead-based sandwich hybridization format," Proc. Natl. Acad. Sci. USA, 86:1173-1177 (1989).

Landegren, U. et al., "A Ligase-Mediated Gene Detection Technique," Science, 241:1077-1080 (1988).

Li, M. et al., "BEAMing up for detection and quantification of rare sequence variants," Nature Methods, 3(2):95-97 (2006).

Li, J. et al., "Replacing PCR with COLD-PCR enriches variant DNA sequences and redefines the sensitivity of genetic testing," Nature Medicine, 14(5):579-584 (2008), and Supplementary Data, 10 pages.

Maheswaran, S. et al., "Detection of Mutations in EGFR in Circulating Lung-Cancer Cells," N Engl J Med, 359:366-77 (2008).

Miele, E. A. et al., "Autocatalytic Replication of a Recombinant Rna," J. Mol. Biol., 171:281-295 (1983).

Miranda, K. C. et al., "Nucleic acids within urinary exosomes/microvesicles are potential biomarkers for renal disease," Kidney International, 78:191-199 (2010); doi:10.1038/ki.2010.106.

Mulloy, R. et al., "Epidermal Growth Factor Receptor Mutants from Human Lung Cancers Exhibit Enhanced Catalytic Activity and Increased Sensitivity to Gefitinib," Cancer Res, 67(5):2325-30 (2007).

Myers, R. M. et al., "Detection of Single Base Substitutions by Ribonuclease Cleavage at Mismatches in RNA:DNA Duplexes," Science, 230:1242-1246 (1985).

Nakazawa, H. et al., "UV and skin cancer: Specific p53 gene mutation in normal skin as a biologically relevant exposure measurement," Proc. Natl. Acad. Sci. USA, 91:360-364 (1994).

Nillson, J. et al., "Prostate cancer-derived urine exosomes: a novel approach to biomarkers for prostate cancer," British Journal of Cancer, 100:1603-1607 (2009).

Orita, M. et al., "Detection of polymorphisms of human DNA by gel electrophoresis as single-strand conformation polymorphisms," Proc. Natl. Acad. Sci., 86:2766-2770 (1989).

Pao, W. et al., "Acquired Resistance of Lung Adenocarcinomas to Gefitinib or Erlotinib Is Associated with a Second Mutation in the EGFR Kinase Domain," PLoS Med., 2(3):e73; Epub Feb. 22, 2005; 11 pages; http://www.plosmedicine.org.

Raposo, G. et al., "B Lymphocytes Secrete Antigen-presenting Vesicles," J. Exp. Med., 183:1161-1172 (1996).

Skog, J. et al., "Glioblastoma microvesicles transport RNA and protein that promote tumor growth and provide diagnostic biomarkers," Nat Cell Biol., 10(12):1470-1476 (2008).

Steemers, F. J. et al., "Whole-genome genotyping with the single-base extension assay," Nature Methods, 3(1):31-33 (2006).

Suda, K. et al., "EGFR T790M Mutation. A Double Role in Lung Cancer Cell Survival?" J Thorac Oncol., 4:1-4 (2009).

Taylor, D. D. & Gercel-Taylor, C., "MicroRNA signatures of tumor-derived exosomes as diagnostic biomarkers of ovarian cancer," Gynecologic Oncology, 110:13-21 (2008).

Thakur, B. K. et al., "Double-stranded DNA in exosomes: a novel biomarker in cancer detection," Cell Research, 24:766-769 (2014).

Thress, K. S. et al., "EGFR mutation detection in ctDNA from NSCLC patient plasma: A cross-platform comparison of leading technologies to support the clinical development of AZD9291," Lung Cancer, 90:509-515 (2015).

Velcelescu, V. E. et al., "Serial Analysis of Gene Expression," Science, 270:484-487 (1995).

Vikis, H. et al., "EGFR-T790M Is a Rare Lung Cancer Susceptibility Allele with Enhanced Kinase Activity," Cancer Res, 67(10):4665-4670 (2007).

Krug, A. K. et al., "Abstract B136: Plasma EGFR mutation detection using a combined exosomal RNA and circulating tumor DNA approach in patients with acquired resistance to first-generation EGFR-TKIs," vol. 14, Issue 12, Supplement 2 (2015), 2 pages.

Kuang, Y. et al., Noninvasive Detection of EGFR T790M in Gefitinib or Erlotinib Resistant Non-Small Cell Lung Cancer, Clin Cancer Res, 15(8):2630-2636 (2009).

Catsburg, A. et al., "Analysis of multiple single nucleotide polymorphisms (SNP) on DNA traces from plasma and dried blood samples," Journal of Immunological Methods, 321:135-141 (2007).

Enderle, D. et al., "Development of a one-step isolation platform for exosomal RNA and circulating cell-free DNA from cancer plasma samples," European Journal of Cancer, vol. 50, Suppl. 6, p. 102 (2014), 1 page.

Müller, B. et al., "Optimized Strategy for Rapid Cytochrome P450 2D6 Genotyping by Real-Time Long PCR," Clinical Chemistry, 49(10):1624-1631 (2003).

Skronski, M. et al., "Reliability of EGFR mutations detection in NSCLC brain metastases by two different allele-specific PCR methods," European Respiratory Journal, vol. 40, Issue Suppl 56, Abstract No. 7263, Publication No. 1397 (2012), 1 page.

(56) References Cited

OTHER PUBLICATIONS

Wang, H. et al., "Allele-Specific, Non-Extendable Primer Blocker PCR (AS-NEPB-PCR) for DNA Mutation Detection in Cancer," The Journal of Molecular Diagnostics, 15(1):62-69 (2013).

* cited by examiner

| Parameter | Training data (StDev) | Clinical validation data |
|---|---|---|
| AUC | 0.94 (± 0.06) | 0.96 |
| Specificity | 0.95 (± 0.06) | 0.89 |
| Sensitivity | 0.91 (± 0.09) | 0.92 |
| Accuracy | 0.93 (± 0.06) | 0.91 |
| Precision | 0.95 (± 0.06) | 0.89 |
| Negative Predictive Value | 0.92 (± 0.07) | 0.92 |
| Positive Predictive Value | 0.95 (± 0.06) | 0.89 |

METHODS AND COMPOSITIONS TO DETECT MUTATIONS IN PLASMA USING EXOSOMAL RNA AND CELL FREE DNA FROM NON-SMALL CELL LUNG CANCER PATIENTS

This application is a national stage application, filed under 35 U.S.C. 371, of International Application No. PCT/US2017/062370, filed Nov. 17, 2017. International Application No. PCT/US2017/062370 claims priority to, and the benefit of U.S. Provisional Application No. 62/428,059, filed Nov. 30, 2016. The contents of each of the aforementioned patent applications are incorporated herein by reference in their entireties.

SEQUENCE LISTING

"The instant application contains a Sequence Listing which has been submitted electronically in ASCII format and is hereby incorporated by reference in its entirety. Said ASCII copy, created on Apr. 30, 2019, is named EXOS_029_N01US_SeqList.txt and is 21,915 bytes in size.

FIELD OF THE INVENTION

The present invention relates generally to the field of biomarker analysis, particularly determining genomic alterations from biological samples, including plasma samples.

BACKGROUND

Increasing knowledge of the genetic and epigenetic changes occurring in cancer cells provides an opportunity to detect, characterize, and monitor tumors by analyzing tumor-related nucleic acid sequences and profiles. These changes can be observed by detecting any of a variety of cancer-related biomarkers. Various molecular diagnostic assays are used to detect these biomarkers and produce valuable information for patients, doctors, clinicians and researchers. So far, these assays primarily have been performed on cancer cells derived from surgically removed tumor tissue or from tissue obtained by biopsy.

However, the ability to perform these tests using a bodily fluid sample is oftentimes more desirable than using a patient tissue sample. A less invasive approach using a bodily fluid sample has wide ranging implications in terms of patient welfare, the ability to conduct longitudinal disease monitoring, and the ability to obtain expression profiles even when tissue cells are not easily accessible.

Accordingly, there exists a need for new, minimally invasive, or noninvasive methods of reliably detecting biomarkers, for example, biomarkers in plasma microvesicles, to aid in diagnosis, prognosis, monitoring, therapy selection, as well as other areas related to any given disease or other medical condition.

SUMMARY OF THE INVENTION

The present invention is in the technical field of biotechnology. More particularly, the present invention is in the technical field of molecular biology.

In molecular biology, molecules, such as nucleic acids, can be isolated from human sample material, such as plasma and other biofluids, and further analyzed with a wide range of methodologies.

Human biofluids contain cells and cell free sources of molecules shed by all cells of the body. Nucleic acids from cell free sources include from extracellular vesicles (EVs), and cell free DNA (cfDNA), which is likely to be derived from apoptotic and necrotic tissue. Small, i.e., between 30-200 nm in diameter, exosomes are one class of EVs that also include apoptotic bodies and shedding microvesicles. Exosomes and other EVs are particularly interesting as cancer biomarkers since they are stable carriers of genetic material and proteins from their cell of origin, but unlike apoptotic bodies from a dying process, exosomes are continuously and actively released into biofluids by all living cells including tumor cells, either through the formation of multivesicular bodies (MVBs) or direct budding from the plasma membrane. For the purpose of describing the present invention, the words of microvesicles, EVs and exosomes can be used interchangeably.

Since cell free nucleic acids such as the RNA contained in exosomes and other EVs (exoRNA), DNA contained in exosomes and other EVs (exoDNA) and free circulating nucleic acids (DNA and RNA) are shed not only by normal somatic cells, but also aberrant cancer cells, an analysis of a combined isolation of nucleic acids from exosomal and other EVs and cell-free nucleic acids from human biofluid samples can reveal the existence and type of cancer cells in a patient.

Non-small cell lung cancer (NSCLC) comprises ~85% of all diagnosed lung cancers and targeted Epidermal Growth Factor Receptor (EGFR) inhibitor therapy is available for patients with known EGFR mutations in their tumor. The T790M mutation on exon 20 of EGFR is a primary mechanism of acquired resistance to first generation EGFR inhibitors such as gefitinib, erlotinib and other molecules that bind to the tyrosine kinase domain such as lapatinib, cetuximab, panitumumab, vandetanib, neratinib and necitumumab. Although this genetic alteration has also been found in tumors from treatment naïve patients, approximately 60% of patients that are refractory to EGFR inhibitor therapy harbor this mutation. Therefore, in addition to being used as a biomarker for patient stratification before treatment and prediction for treatment outcome for the second-generation EGFR inhibitors such as osimertinib, T790M can be used to monitor for the emergence of resistance EGFR inhibitors.

Other genomic alterations within EGFR are of high interest due to the high frequency of occurrence. For instance, exon 21 L858R mutation is present in approximately 43%, exon 19 deletions and insertions in 49% of NSCLC EGFR mutated lung tumors. Patients that harbor these alterations are candidates for treatment with TKIs such as gefitinib and erlotinib.

Obtaining tissue biopsies from NSCLC is challenging, and as many as 49% of patients have no tissue for molecular analysis of EGFR, therefore monitoring the mutations in biofluids as a liquid biopsy have proven useful. In the present invention, we combined the information derived from the dying cellular processes (e.g., apoptosis and necrosis) from circulating nucleic acids, or "circulatingNA" and from the living processes from EV's derived nucleic acids, or "exoNA". Because of this, the co-isolation of exoNA and circulatingNA from the same volume of biofluid sample, leads to an extremely sensitive assay. It is understood that while the examples provided herein demonstrate the co-isolation of exoNA and circulatingNA, the methods and kits provided herein are useful for co-isolating any combination of exoNA, e.g., exoRNA and/or exoDNA, and any DNA and RNA found in the biofluid sample, such as, e.g., cfDNA, necrotic DNA, or any other circulating DNA or RNA found in the sample including those isolated through enrichment of different fractions such as platelets.

The existence and quantity of a modification in one or more of exons 19, 20, and/or 21 in EGFR, in particular, T790M, L858R, one or more exon19 insertions and/or one or more exon19 deletions in EGFR in a patient can be used to guide or select the treatment options, as well as monitor disease relapse, molecular residual disease, amongst other applications. As used herein, a "modification" includes a mutation, one or more insertions, and one or more deletions at one or more bases.

Here we describe the application of a PCR-based assay on exoNA and circulatingNA isolated from human biofluids that detects T790M, L858R, one or more exon19 insertions and/or one or more exon19 deletions in EGFR with high sensitivity and specificity.

The present invention is a method directed to a complete workflow from sample extraction to mutation identification using exoNA and circulatingNA. This invention uses a mutant enrichment strategy during the pre-amplification reaction to selectively amplify the mutant sequences. An additional modification in the mutant specific primer during the Amplification Refractory Mutation Detection System (ARMS)-triplex qPCR step includes the presence of a modified base, such as 2-aminopurine, 8-amino-2'-deoxyadenosine, trimetroxystilbene, C-5 propynyl-deoxycytidine, C-5 propynyl-deoxyuridine, 2-amino-2'-deoxyadenosine-5'-triphosphate, 2,6-diaminopurine (2-amino-dA), inverted dT, inverted dideoxy-T, hydroxymethyl dC, iso-dC, 5-methyl dC, aminoethyl-phenoxazine-deoxycytidine, and locked nucleic acids (LNA's), and the inclusion of at least one mismatched base at one of the bases to increase the nucleic acid interaction at the 3' end of the mutant specific primer. In some embodiments, the at least one mismatched base is the fourth to the last, antepenultimate, penultimate or the last base of the mutant specific primer. State-of-the-art machine learning and data-mining techniques are applied to the qPCR data generated by the real time PCR instrument to discriminate between positive and negative samples or to quantify the strength of positive or negative samples.

The present disclosure provides methods of detecting one or more biomarkers in a biological sample to aid in diagnosis, prognosis, monitoring, or therapy selection for a disease such as, for example, cancer. The methods and kits provided herein are useful in detecting one or more biomarkers from plasma samples. The methods and kits provided herein are useful in detecting one or more biomarkers from the extracellular fraction of plasma samples.

The methods and kits provided herein are useful for detecting an Epidermal Growth Factor Receptor (EGFR) mutation in a biological sample. In some embodiments, the EGFR mutation is a modification in one or more of exons 19, 20, and/or 21 in EGFR, including the T790M mutation on exon 20. In some embodiments, the EGFR mutation are sensitizing mutations and other EGFR mutations, such as, L858R in exon 21, one or more exon19 insertions and/or one or more exon19 deletions of EGFR.

The present disclosure provides methods and kits for detecting the EGFR T790M, mutation, the L858R mutation, one or more exon19 insertions and/or one or more exon19 deletions in a biological sample. In some embodiments, the biological sample is plasma.

The present disclosure provides a reaction designed to capture and concentrate EVs, isolate the corresponding nucleic acids, and to simultaneously detect the presence of T790M, the L858R mutation, one or more exon19 insertions and/or one or more exon19 deletions in circulatingNA and exoNA using quantitative PCR and other PCR-based or PCR-free methods as the downstream analytical platform such as BEAMING or NGS.

Generally, the methods and kits of the disclosure include the following steps:
1) Isolation of exoNA and circulatingNA from a biofluid sample:
   a. Binding of exosomes and other EVs as well as circulatingNA to IEX, size exclusion columns, beads and/or other solid surfaces;
   b. Release from matrix using lysing conditions as well as other denaturation methods;
   c. Isolation of total nucleic acids from lysate using silica columns, beads and other surface-based methods;
2) Reverse Transcription (RT) of isolated total exoNA, including circulatingNA:
   a. First strand synthesis using a single or a blend of RT enzymes and oligonucleotides;
   b. Use of a control of inhibition, exogenous RNA spike.
   c. Use of other controls (i.e. positive and negative controls, extraction controls, etc.)
3) Pre-amplification of the complete isolated and reverse transcribed material:
   a. Pre-amplification reaction using PCR specific for:
      i. T790M in EGFR exon20 and/or L858R in EGFR exon 21, and/or one or more deletions and/or insertions in EGFR exon19;
      ii. Small amplicons to capture fragmented material (from the circulatingNA and fragmentedexoNA);
      iii. Multiple control amplifications at other genomic locations;
      iv. Control of inhibition and other controls (e.g., extraction control);
      v. Inclusion of hydrophobic nucleic acid and other blocker technologies to enrich for the mutant fraction of the nucleic acid molecules;
4) Detection and quantification of T790M and/or L858R and/or the one or more exon19 deletions and/or exon19 insertions and control amplicons in the pre-amplification reaction:
   a. A part of the pre-amplification reaction is used as a template for multiplex qPCR reactions used to detect T790M and/or L858R and/or one or more the one or more exon19 insertions and/or exon19 deletions, and other controls (e.g., control of inhibition, extraction control, wild type control, etc.).
   b. The presence of an additional modification in the mutant specific primer during the Amplification Refractory Mutation Detection System (ARMS)-triplex qPCR step such as 2-aminopurine, 8-amino-2'-deoxyadenosine, trimetroxystilbene, C-5 propynyl-deoxycytidine, C-5 propynyl-deoxyuridine, 2-amino-2'-deoxyadenosine-5'-triphosphate, 2,6-diaminopurine (2-amino-dA), inverted dT, inverted dideoxy-T, hydroxymethyl dC, iso-dC, 5-methyl dC, aminoethyl-phenoxazine-deoxycytidine, and locked nucleic acids (LNA's), and the inclusion of at least one mismatched base at one of the bases to increase the nucleic acid interaction at the 3' end of the mutant specific primer.
   c. The incorporation, in addition to previous claim of an additional mismatch at one of the bases of the mutant specific primer. In some embodiments, at least one mismatched base is the fourth to the last, antepenultimate, penultimate or the last base of the mutant specific primer.

In some embodiments, the methods provided herein employ further manipulation and analysis of the detection and quantification of T790M, L858R, the one or more exon19 insertions and/or the one or more exon19 deletions. In some embodiments, the methods further include the following step:

5) Machine-learning model and statistical analysis:
   a. To discriminate or quantify the disease outcome of patients and to generalize to unseen patients, a state-of-the-art machine learning model was trained on clinical data in a k-fold cross-validation.
   b. For each sample several features are used for training the model from the qPCR step such as but not limited to CT values, delta CT values, raw Rn values as well as ROX normalized dRn values.
   c. Within each cross-validation step an internal optimization step is used to find the optimal parameters of the model.
   d. Bootstrapping is used to repeat steps (a)-(c) n-times to derive stability estimates on how well the model performs on different train-test splits.
   e. We determine various boundary conditions on internal controls to establish filters for quality control before sample classification to exclude samples that show spurious behavior.

In some embodiments, the methods and kits described herein isolate the EV fraction by capturing the extracellular vesicles to a surface and subsequently lysing the EVs to release the nucleic acids, particularly but not exclusively to RNA, contained therein.

Previous procedures used to isolate and extract nucleic acids from the EV fraction of a biological sample relied on the use of ultracentrifugation, e.g., spinning at less than 10,000×g for 1-3 hours, followed by removal of the supernatant, washing the pellet, lysing the pellet and purifying the nucleic acids, e.g., RNA on a column. These previous methods demonstrated several disadvantages such as being slow, tedious, subject to variability between batches, and not suited for scalability. The isolation and extract methods used herein overcome these disadvantages and provide a spin-based column for isolation and extraction that is fast, robust and easily scalable to large volumes.

The methods and kits isolate and extract nucleic acids, e.g., exoNA and cell free NA from a biological sample using the following extraction procedures described in PCT Publication Nos. WO 2016/007755 and WO 2014/107571, the contents of each of which are incorporated by reference herein in their entirety. Briefly, the EV fraction is bound to a membrane filter, and the filter is washed. Then, a reagent is used to perform on-membrane lysis and release of the nucleic acids, e.g., RNA and cfDNA. Extraction is then performed, followed by conditioning. The nucleic acids, e.g., exoNA and circulating NA, is then bound to a silica column, washed and then eluted.

In some embodiments, the biological sample is a bodily fluid. The bodily fluids can be fluids isolated from anywhere in the body of the subject, for example, a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof. For example, the bodily fluid is urine, blood, serum, or cerebrospinal fluid.

The methods and kits of the disclosure are suitable for use with samples derived from a human subject. The methods and kits of the disclosure are suitable for use with samples derived from a non-human subject such as, for example, a rodent, a non-human primate, a companion animal (e.g., cat, dog, horse), and/or a farm animal (e.g., chicken).

The methods described herein provide for the extraction of nucleic acids from EV. In some embodiments, the extracted nucleic acids are RNA. The extracted RNA may comprise messenger RNAs, transfer RNAs, ribosomal RNAs, small RNAs (non-protein-coding RNAs, non-messenger RNAs), microRNAs, piRNAs, exRNAs, snRNAs and snoRNAs, circulating RNA or any combination thereof.

In any of the foregoing methods, the nucleic acids are isolated from or otherwise derived from an extracellular vesicle fraction.

In any of the foregoing methods, the nucleic acids are cell free nucleic acids, also referred to herein as circulating nucleic acids. In some embodiments, the cell free nucleic acids are DNA or RNA.

In some embodiments, one or more control particles or one or more nucleic acid(s) may be added to the sample prior to microvesicle isolation and/or nucleic acid extraction to serve as an internal control to evaluate the efficiency or quality of microvesicle purification and/or nucleic acid extraction. The methods described herein provide for the efficient isolation and the control nucleic acid(s) along with the microvesicle fraction. These control nucleic acid(s) include one or more nucleic acids from Q-beta bacteriophage, one or more nucleic acids from virus particles, or any other control nucleic acids (e.g., at least one control target gene) that may be naturally occurring or engineered by recombinant DNA techniques. In some embodiments, the quantity of control nucleic acid(s) is known before the addition to the sample. The control target gene can be quantified using real-time PCR and/or any other PCR-based or PCR-free downstream methodology (such as droplet digital PCR, OD measurement, etc.). Quantification of a control target gene can be used to determine the efficiency or quality of the extracellular vesicle purification or nucleic acid extraction processes.

In some embodiments, the control nucleic acid is a nucleic acid from a Q-beta bacteriophage, referred to herein as "Q-beta control nucleic acid." The Q-beta control nucleic acid used in the methods described herein may be a naturally-occurring virus control nucleic acid or may be a recombinant or engineered control nucleic acid. Q-beta is a member of the leviviridae family, characterized by a linear, single-stranded RNA genome that consists of 3 genes encoding four viral proteins: a coat protein, a maturation protein, a lysis protein, and RNA replicase. When the Q-beta particle itself is used as a control, due to its similar size to average microvesicles, Q-beta can be easily purified from a biological sample using the same purification methods used to isolate EV, as described herein. In addition, the low complexity of the Q-beta viral single-stranded gene structure is advantageous for its use as a control in amplification-based nucleic acid assays. The Q-beta particle contains a control target gene or control target sequence to be detected or measured for the quantification of the amount of Q-beta particle in a sample. For example, the control target gene is the Q-beta coat protein gene. When the Q-beta particle itself is used as a control, after addition of the Q-beta particles to the biological sample, the nucleic acids from the Q-beta particle are extracted along with the nucleic acids from the biological sample using the extraction methods described herein. When a nucleic acid from Q-beta, for example, RNA from Q-beta, is used as a control, the Q-beta nucleic acid is extracted along with the nucleic acids from the biological sample using the extraction methods described herein. Detection of the Q-beta control target gene can be determined by RT-PCR analysis, for example, simultaneously with the biomarker(s) of interest (e.g., T790M EGFR mutation, L858R mutation, the one or more exon19 insertions and/or the one or more exon19 deletions, each alone or in combination with one or more additional biomarkers). A standard curve of at least 2, 3, or 4 known concentrations in 10-fold dilution of a control target gene can be used to determine copy number. The copy number detected and the quantity of Q-beta particle added or the copy number detected and the quantity of Q-beta nucleic acid, for example, Q-beta RNA, added can be compared to determine the quality of the isolation and/or extraction process.

In some embodiments, 10-10,000 copies, such as 50, 100, 150, 200, 250, 300, 350, 400, 450, 500, 1,000 or 5,000 copies of Q-beta particles or Q-beta nucleic acid, for example, Q-beta RNA, added to a bodily fluid sample. In some embodiments, 100 copies of Q-beta particles or Q-beta nucleic acid, for example, Q-beta RNA, are added to a bodily fluid sample. When the Q-beta particle itself is used as control, the copy number of Q-beta particles can be calculated based on the ability of the Q-beta bacteriophage to infect target cells. Thus, the copy number of Q-beta particles is correlated to the colony forming units of the Q-beta bacteriophage.

In some embodiments, the methods and kits described herein include one or more in-process controls. In some embodiments, the in-process control is detection and analysis of an internal reference gene that indicates plasma quality (i.e., an indicator of the quality of the plasma sample). In some embodiments, the reference gene(s) is/are a plasma-inherent transcript. In some embodiments, the reference gene(s) (and their corresponding alternative aliases) is/are selected from the group consisting of EML4, RPL4, NDUFA1, beta-actin, exon 7 of EGFR, ACADVL; PSEN1; ADSL; AGA; AGL; ALAD; ABCD1; ARSB; BCKDHB; BTD; CDK4; ERCC8; CLN3; CPDX; CST3; CSTB; DDB2; DLD; TOR1A; TAZ; EMD; ERCC3; ERCC5; ERCC6; ETFA; F8; FECH; FH; FXN; FUCA1; GAA; GALC; GALT; GBA; GBE1; GCDH; GPI; NR3C1; GSS; MSH6; GUSB; HADHA; HMBS; HMGCL; HPRT1; HPS1; SGSH; INSR; MEN1; MLH1; MSH2; MTM1; MTR; MUT; NAGLU; NF1; NF2; NPC1; OAT; OCRL; PCCA; PDHA1; PEPD; PEX12; PEX6; PEX7; PGK1; PHKA2; PHKB; PKD1; PLOD1; PMM2; CTSA; PPDX; PTEN; PTS; PEX2; PEX5; RB1; RPGR; ATXN1; ATXN7; STS; TCOF1; TPI1; TSC1; UROD; UROS; XPA; ALDH3A2; BLMH; CHM; TPP1; CYB5R3; ERCC2; EXT2; GM2A; HLCS; HSD17B1; HSD17B4; IFNGR1; KRT10; PAFAH1B1; NEU1; PAFAH2; PSEN2; RFX5; SOD1; STK11; SUOX; UBE3A; PEX1; APP; APRT; ARSA; ATRX; GALNS; GNAS; HEXA; HEXB; PCCB; PMS1; SMPD1; TAP2; TSC2; VHL; WRN; GPX1; SLC11A2; IFNAR1; GSR; ADH5; AHCY; ALDH2; ALDH9A1; BCKDHA; BLVRB; COMT; CRAT; CYP51A1; GART; GGCX; GRINA; GSTM4; GUK1; IGF2R; IMPDH2; NR3C2; NQO2; P4HA1; P4HB; PDHB; POLR2A; POLR2B; PRIM2; RPL4; RPL5; RPL6; RPL7A; RPL8; RPL11; RPL23; RPL19; RPL22; RPL23A; RPL17; RPL24; RPL26; RPL27; RPL30; RPL27A; RPL31; RPL32; RPL34; RPL35A; RPL37A; RPL36AL; ITSN1; PRKCSH; REEP3; NKIRAS2; TSR3; ZNF429; SMAD5; STX16; C16orf87; LSS; UBE2W; ATP2C1; HDGFRP2; UGP2; GRB10; GALK2; GGA1; TIMM50; MED8; ALKBH2; LYRM5; ZNF782; MAP3K15; MED11; C4orf3; RFWD2; TOMM5; C8orf82; PIM3; TTC3; PPARA; ATP5A1; ATP5C1; PLEKHA1; ATP5D; ATE1; USP16; EXOSC10; GMPR2; NT5C3; HCFC1R1; PUS1; ATP5G1; ECHDC1; ATP5G2; AFTPH; ANAPC11; ARL6IP4; LCLAT1; ATP5G3; CAPRIN2; ZFYVE27; MARCH8; EXOSC3; GOLGA7; NFU1; DNAJB12; SMC4; ZNF787; ZNF280D; BTBD7; THOC5; CBY1; PTRH1; TWISTNB; SMAD2; C11orf49; HMGXB4; UQCR10; SMAD1; MAD2L1BP; ZMAT5; BRPF1; ATP5J; RREB1; MTFP1; OSBPL8; ATP5J2; RECQL5; GLE1; ATP5H; STRADA; ERLIN2; NHP2L1; BICD2; ATP5S; HNRNPD; MED15; MANBAL; PARP3; OGDH; CAPNS1; NOMO2; ALG11; QSOX1; ZNF740; RNASEK; SREBF1; MAGED1; HNRNPL; DNM2; KDM2B; ZNF32; MTIF2; LRSAM1; YPEL2; NEURL4; SF3A1; MARCH2; PKP4; SF3B1; VPS54; NUMB; SUMO1; RYK; IP6K2; JMJD8; C3orf37; IP6K1; ERBB2IP; LRRC37A2; SIAH1; TSPAN17; MAPKAP1; WDR33; ARHGAP17; GTDC1; SLC25A25; WDR35; RPS6KA4; UHRF1BP1L; RPS4X; GOSR1; ALG8; SDCBP; KLHL5; ZNF182; ZNF37A; SCP2; ZNF484; L3MBTL3; DEPDC5; CACYBP; SPOP; METTL13; IFRD1; GEMIN7; EI24; RWDD1; TULP4; SMARCB 1; LMBRD2; CSDE1; SS18; IRGQ; TFG; BUB3; CEPT1; COA5; CNOT4; TTC32; C18orf25; CISD2; CGGBP1; LAMTOR4; BCAP29; SLC41A3; SEPT2; TMEM64; MXI1; USP20; NUPL1; TPST2; PICALM; CCBL2; THAP7; TFIP11; C6orf1; PPP1CA; WDR89; ZNF121; FNIP1; C6orf226; CCT3; NIPA2; CUL4A; TCP1; STK16; RCHY1; CKAP5; RPS5; GEMIN2; CCT6A; PPP2CB; CCT7; VWA8; BRD9; KIAA0930; ZCCHC11; C12orf29; KIAA2018; VPS8; TMEM230; ANKRD16; SSBP3; ZNF655; C20orf194; FAM168B; DALRD3; SSBP4; KDM1A; RPS6; ZNF766; TTC7B; RNF187; IBA57; ERCC6L2; RAP1A; TNK2; RAP1B; GLT8D1; SPRTN; ATP11C; HERPUD1; RPS7; PDLIM5; FYTTD1; SEPT7; CDK5RAP2; TRAPPC2; PCGF6; CHCHD7; OLA1; NAA30; ARHGEF10L; BTBD1; RPS8; MSL1; MCRS1; ZNF302; CTNNBIP1; DNAJC21; AKTIP; FOXP4; SEC61G; U2AF2; CCDC66; GOSR2; CTBP1; MYPOP; SLC3A2; DCTD; ABI1; CTU2; RGMB; COA6; UBE2NL; C16orf88; RPS9; CCNC; KRIT1; SEH1L; FXR1; AGPHD1; ALG10B; C2orf68; GDPGP1; PTRHD1; SRRD; EIF2AK4; MAD1L1; EXOC7; SLTM; CXorf40B; EXOC6; SUPT2OH; AKT1; CUTA; DBNL; CARS; USP21; DDX19B; ETFB; EMC6; ILK; FAM96A; TM9SF1; ZNF638; MRPL22; RPS11; FAM13A; MPG; DNAJC25; TAF9; RPS13; RFFL; SP3; TMCC1; ZNF2; MAEA; GOPC; SIRT3; ERMAP; C14orf28; ZHX1; C2orf76; CCDC58; OS9; RAB28; VMA21; C5orf45; OPA3; RPS15; SORBS3; TPM1; CMC4; VPS13A; POLR3H; BRCC3; SERBP1; CORO1B; FPGS; VPS13C; NARG2; GCOM1; POLR2M; FAHD1; SERF2; NME1-NME2; NME2; NAE1; HAX1; RPS16; PUM1; RPS20; ZSCAN26; ZNF805; IQCB1; RPS21; GPHN; ARF1; TM2D2; CANX; KALRN; LIN52; LRRC24; ZNF688; TNRC6B; CD82; ZNF197; CBWD5; EXOC1; MINK1; YIPF5; BRMS1; ARPC4; RPS23; RPS14; ABCF1; CSNK1A1; ADAR; U2AF1; AP2M1; IRAK1; TAF5L; DUT; RAB12; ANO6; NDEL1; ARFIP1; CELF1; VRK3; FAM108B1; RPS24; RPS25; CCM2; TCAIM; KCTD21; C6orf120; PLEKHG1; GLTPD1; WDR45; ZFAT; ZNF16; METTL17; ZNF181; AP2B1; AP1G1; ARHGAP5; COX19; ZNF451; RAB24; CTNS; SRSF7; TP53BP2; PLAA; PLD3; ELP6; ERGIC1; TRMT11; CCDC90A; INF2; CRELD1; DHRS12; ZNF613; DNAJB14; DDX59; C19orf12; MRI1; YTHDC1; FDX1L; TMEM150A; TIPRL; CSNK1G3; CPT1A; KLF10; TMPO; NR2C1; UBE2V1; SLC35A2; ZNF174; ZNF207; STK24;

MINOS1; ZNF226; PQBP1; LCMT1; HNRNPH2; USP48; RRM1; RPAIN; FBXO7; TMEM259; CYFIP1; FAIM; GPR155; MTERFD3; AMD1; NGRN; PAIP2; SAR1B; WIPI2; CSTF1; BABAM1; PPM1B; PHF12; RHOT1; AMZ2; MYO19; ACOT9; BBS9; TRPT1; NOP2; TIAL1; UBA52; DMAP1; EIF2B4; NHP2; ITPRIPL2; RPL14; C18orf32; SRA1; UFD1L; VPS26A; BOLA3; SDHC; GTF3C2; HHLA3; EXOC4; AGAP1; FOXK1; ARL5A; GGPS1; EIF3B; THYN1; STAU1; USP14; RUFY3; GON4L; AGPAT3; SIL1; BTF3; PARL; EEF1B2; GATSL3; ZNF630; NPM1; NCKAP5L; HSD17B10; REV1; DIXDC1; SLC38A10; NARF; ALG13; ATP6V1E1; NDUFAF5; ATP6V0B; NPRL3; KIAA0317; ETNK1; DNAJB2; SEC14L1; CCNL2; PICK1; DPH2; USP9X; IAH1; CREBZF; PRMT5; ZMYM5; TIRAP; YIF1B; UNC45A; CHTF8; TYW5; SNAPC3; NBPF10; SDCCAG3; DEDD; C4orf29; CDC42; OXLD1; GPX4; STRN4; FKRP; ZNF808; C19orf55; ZNF674; ZNF384; INTS6; MLLT4; TCERG1; ARL16; MAPK3; FAM133B; MOSPD3; MLH3; NRF1; PQLC2; CEP44; H2AFY; C16orf13; FAM63A; PAPD5; DCUN1D4; PRDM15; U2AF1L4; HAGH; COA3; YARS2; PHF11; ASB1; MTMR12; RUFY1; SIDT2; RHBDD2; ERAP1; EFTUD1; TMEM70; LINS; CRCP; ACP1; ZXDC; METTL21D; PPAN-P2RY11; INCENP; UEVLD; ABCE1; TROVE2; PGP; CEP63; PPP4R1; CEP170; ANKZF1; PSPC1; WHSC1; ZNF205; FAM98B; CAST; TRAPPC5; TMEM80; PSAP; SUMF2; ABHD12; ACBD5; ZNF565; GEMIN8; DLGAP4; SMIM8; ZNF706; COASY; MINA; AGAP3; SLC9A6; MAZ; NCBP2; ATPAF1; FEZ1; NSL1; SMC2; TATDN3; FRS2; EIF4G2; CHD2; ENGASE; CRTC3; SNUPN; POT1; TTC14; KDM5A; XRN1; PIGY; PARP2; NGDN; TRAK1; MFSD12; SHPRH; ZSWIM7; GTPBP10; SEC24B; STAG2; TPM3; MSMP; SMAP1; ZNF557; NET1; DPH3; MUTYH; PHACTR4; HIPK3; CLCC1; SCYL1; UBL5; TNFRSF1A; TOP2B; ACSS2; TMUB2; CLTA; UBTF; QSER1; CDC14B; ATG9A; SREK1; SENP7; SEC31A; SPPL2B; RNF214; SLC25A45; NCOR2; ZFYVE19; RBM23; POMT1; DPH5; IRF2BP2; PNKD; BCLAF1; HNRNPC; PHF16; TSEN34; PPCS; SLC39A7; MTMR14; UBXN2B; APH1A; WTH3DI; URGCP; AGAPE; ALG9; MIER1; SRSF1; FAM127B; CDC16; TMEM134; UBN1; TBCE; MED24; FAM177A1; KTN1; PAICS; TRAPPC6B; HNRNPUL2; TMTC4; FNDC3A; KIAA1191; FKTN; TMEM183B; OCIAD1; CREBBP; TAX1BP1; BCS1L; CUL4B; KIAA1147; KIAA0146; U2SURP; ZNF629; UNK; FTO; WHAMM; SNED1; BEND3; GPR108; INTS1; ZNF697; PLEKHM3; USP45; USP6NL; ZNF823; TNRC18; RGP1; TMEM223; METTL23; SETD5; BAHCC1; UNC119B; MGA; CACTIN; TMEM218; C15orf57; DNLZ; COMMD5; JMJD6; NXF1; THOC2; CPSF4; PRKDC; ZNF623; ACD; TCTN1; PIH1D2; C11orf57; ZGPAT; CHMP1A; ZNF133; CEP57L1; RABEP1; TMEM214; NAA60; TMEM219; EARS2; RB1CC1; ZBTB40; ANKRD12; STRN3; DNAAF2; WBP1L; THADA; PLOD3; DDT; DDTL; MZT2A; C11orf83; NADKD1; CTNND1; FOXN3; MAP1LC3B2; MYSM1; C17orf89; AAMP; UQCRHL; TRAPPC13; FAM195B; TXNRD1; ACLY; RPP38; ACO2; HNRNPF; CTNNB1; LIG4; COPA; ZBTB21; ZNF621; DLG1; GRSF1; CRTC1; ZNF419; CHCHD4; DDX17; SGSM2; HTATIP2; CDK10; BAG6; USP5; TMBIM6; C1orf43; PCBP2; TMEM251; JKAMP; AKT1S1; C12orf44; RPP14; FAM89B; BET1L; MID1IP1; FAM160A2; FAM210A; INO80C; ATXN7L3; ZNF862; CCDC43; ZNF506; TINF2; COMMD7; CCNK; KAT6A; POM121C; BCAS3; ULK3; ZNF30; MTFR1L; ZNF146; FTSJD1; RPL22L1; GXYLT1; PTAR1; HIGD1A; C8orf59; EIF5AL1; REPIN1; WDR83; C4orf33; SYS1; IKBKG; C7orf25; SBNO2; IMMT; TMEM192; PDS5A; SENP6; DROSHA; C19orf60; SPATS2L; RAP1GDS1; RC3H2; KIAA0232; KDELR2; PLEKHB2; CENPN; ERLIN1; TMEM55B; MEDT; PID1; MOB4; SLC9B1; PACS2; COMMD9; CXXC1; NRD1; ACOX3; PHF21A; FOXRED2; SIKE1; HNRNPR; TTI2; PCTP; ALPK1; ZFAND5; TBC1D8; PPAPDC1B; IFT43; SNX18; ZNF160; TUBGCP5; ZNF554; OTUD4; PSMA4; RRAS2; GIGYF2; RPP30; FAM118A; PCMTD2; ACVR1; FBRS; TMEM177; RUSC1; ASH2L; CORO1C; ARMC5; ZFYVE16; FAM135A; ZNF142; MYBBP1A; ZBTB10; UBE4B; KIF13A; NUDT19; FBXO45; NUDT7; HECTD4; ZNF250; C6orf136; ADAM10; TMEM87A; SLC35E2B; MECP2; NAA16; SUPT5H; UBE2K; DDX54; TLK2; ZSCAN30; FAM208A; FPGT-TNNI3K; BRD2; NACA; ECE1; TBC1D14; FANCI; FGGY; C17orf51; SEPT9; ARHGEF7; METTL15; ENTPD6; CDC27; THUMPD3; LSM14A; C17orf85; ELK1; NBEAL1; AEBP2; IRAK4; MTRF1L; CLCN7; PAPD4; DHX36; SZRD1; JMJD7; PLA2G4B; FANCL; LIN54; KANSL3; WDR26; GDI2; ADD1; LAMP2; HCCS; CCBL1; ABCD3; MICAL3; SET; GTF3C5; TTC13; NCOA7; BSCL2; BCKDK; SMEK2; ADK; ARIH2OS; MTO1; ZBTB1; PPP6C; PARK7; BCOR; ADPRH; HDGF; CASK; OSGIN2; POLG; THTPA; AP1B1; PIGG; CFLAR; CNBP; PCID2; HMOX2; SMARCAL1; ACSF3; POLD2; AURKAIP1; AUTS2; GPBP1; LRRC8A; TMEM129; UBAP2L; CBX5; MAD2L2; MED18; ZNF84; C14orf2; TSEN15; METTL21A; ERLEC1; CRY2; CRLS1; PAN2; SPRYD7; ASAH1; ING4; NMRK1; PEX26; MFN2; ATXN3; TMEM14B; STXBP5; SPG21; CEACAM19; AP4S1; RWDD3; TFRC; ORMDL1; VPS53; UBP1; NUDCD1; KCTD6; VGLL4; ZNF717; SLC39A13; DIS3; GNE; TPRN; LYRM1; LACC1; AP1AR; SMARCAD1; PSMG4; MAPKBP1; USP8; NUDT22; REPS1; LUZP6; DCAKD; SMARCA4; SRRT; GTPBP3; TOMM40; MARK3; INPP1; ENTPD4; NSDHL; TEX264; DNAJC2; KRBOX4; SYCE1L; KIAA1841; AES; GSPT1; ATP6V0A1; ZNF680; CLK3; ZNF562; SHC1; TBCEL; ATF7; MYO9B; EPN1; KARS; COL4A3BP; HSPBP1; FAM108A1; RFC5; SMARCC2; SPTAN1; SRP9; HRAS; SSFA2; HAUS2; THAP5; VRK2; ZNF195; AP1M1; SPAG9; CALU; EIF4E; STYX; C14orf93; LSM5; PSMB5; CCDC149; DNMT1; RTCA; AIFM1; CAB39; PPIP5K1; PWWP2A; SUGT1; ZNF720; TGFBR1; MEF2A; C7orf73; PLCD1; SUN1; HYOU1; FAM58A; PTPN12; SATB1; CIZ1; ATG10; ZCCHC9; SAP30L; ACP2; TMEM106B; EIF2AK1; PSMG3; MAP4; LRRFIP2; NT5C2; CCNJ; TBC1D5; IQSEC1; ZDHHC4; C7orf50; TBCCD1; CDV3; AZI2; C3orf58; GSE1; PARN; HS2ST1; TOMM6; TRMT10A; DERL1; FAM204A; DEK; ARFRP1; IPO11; CCDC152; FIP1L1; ELMOD3; PDHX; MFAP3; DCTN1; MAPK9; FAM160B1; FNDC3B; CRELD2; DNAJA3; NEDD1; ZNF397; ZDHHC3; AGFG1; FKBP2; GIT2; TAF12; LDHA; RBBP4; MKNK1; HDHD1; C12orf73; SMIM13; C5orf24; GDAP2; RPS27A; PPP1R21; PIP5K1A; INPP5K; DCTN4; FAM53C; PTPRK; EEF1E1; EIF2AK2; XPR1; MSRA; ATL2; C8orf40; VDAC3; YWHAZ; HMBOX1; NEIL2; ECD; RPN2; SPATA2; FDPS; RNF185; PHPT1; METTL20; SLC46A3; KIAA1432; MADD; URM1; UCK1; NDUFB11; RUSC2; ABL2; ATG7; PUF60; TRMT1; NIF3L1; CPSF7; PTGES3L-AARSD1; TMUB1; TPRA1; R3HCC1; FBXO28; FAM178A; RPL28; RPS6KC1; CMPK1; ATF6B; ZNF507; OTUD5; FASTKD2; TNPO2; FZR1; ISOC2; CCDC124; RCOR3; SEC13; SGMS2; ATXN7L3B; AKIRIN1; ANP32E; CISD3; ACAD10; APOL1; LYSMD1;

TLK1; GPR107; LANCL1; LRRFIP1; MCTS1; ANAPC5; MEMO1; POLR1B; ANAPC7; ILF3; ATXN1L; BCAP31; TTLL11; CNST; TBL1X; TRAF3IP1; PRKRA; DAXX; ATP13A2; TP53BP1; RAB11FIP3; CLASP1; APLP2; RNASEH2B; ARCN1; SMC6; EMC8; MGRN1; LMAN2L; ARFGAP3; SQSTM1; GTF2H1; TXNL4B; DMTF1; THOC6; PPP3CB; ALG5; PNPLA4; CTIF; CD164; AIMP1; MORF4L2; MGEA5; EDC3; SPNS1; DKC1; ECSIT; C6orf203; INTS12; FLYWCH2; MON1A; SLC35B3; ADCK1; RPUSD3; ADCK4; RRNAD1; RAD51D; ZNF669; NFYC; ITPK1; CLP1; KIAA0141; EFTUD2; ULK2; EHBP1; TGFBRAP1; GHDC; TNRC6C; FBRSL1; SAR1A; HNRPLL; ATG13; CHID1; ERI2; C1orf122; IL11RA; C17orf49; EYS; API5; DAGLB; MPC2; GSTK1; DIS3L; EIF5A; ZNF438; CTDNEP1; SLC25A39; PPHLN1; TPCN1; ZBTB14; MAPRE2; NFRKB; TMEM106C; TCHP; WIBG; COPS2; BSDC1; C12orf65; TRAFD1; LOC729020; C15orf61; PSMA1; LEMD2; TMEM30A; C2orf74; TBC1D7; CDYL; TCTN3; PTPMT1; BANF1; WRAP53; AMFR; AGAP5; CTPS2; TMX2; NAT10; COPB1; UBAC2; DET1; DNAJC7; CD58; DENND4A; PHB2; IMPA1; SMCR7; C11orf95; MYL12B; DTWD1; NFKBIL1; MTHFD2L; ZNF814; CCDC85C; ITGAV; COG2; GPN1; SLC44A2; USP27X; COG6; ZNF619; SKIL; RRP12; MKRN1; AKD1; RELA; VPS37A; HBS1L; INTS9; DOHH; PRMT3; KIAA1671; LAMTOR2; SLC35C1; FAM185A; NGLY1; ETV3; DSN1; ZNF566; ZNF576; KDM8; IPP; MKLN1; CBWD1; SIN3A; ABHD11; ZNF652; OXSM; TSEN2; TEF; NONO; NFE2L2; SETDB1; TMEM205; C4orf52; PGAP2; SCAF4; SPECC1L; EHMT1; TCP11L1; RBM17; ZDHHC7; KIAA0226; GLG1; SAE1; HOMER3; XPC; MEF2BNB; SH2B1; MTFR1; SARS2; SCAPER; SLC12A4; RDH13; TJAP1; FCHO2; HSDL1; TDRD3; RPAP3; FAN1; PARP9; DIP2A; GSK3B; MOGS; TATDN1; ZNF414; ZNF407; TBC1D15; WRB; PIP4K2C; TCF7L2; SRP54; LEPRE1; C1orf86; PQLC1; KDM3A; KDM4C; RBM19; KDM5C; SLC25A5; ANXA4; SCOC; ANXA6; ANXA7; ANXA11; MTHFSD; BIVM; BOD1; SYNCRIP; PLBD2; BUD13; RIOK2; CANT1; MPND; EBNA1BP2; EVI5L; EPS15; TXNDC16; ACOT13; C15orf40; RNF170; SPG11; SETD6; SETDB2; TRAPPC9; POLR3B; NUDT2; ARMC10; CHFR; NPTN; NDFIP2; JMJD4; WDR25; COG5; TINP2; RBM34; TEX10; DUS3L; PPP2R5C; CLK1; PDCD6IP; TMEM189; RBMXL1; COX11; TYW3; RPTOR; HTATSF1; EWSR1; FBXL17; RAB2B; ZSCAN12; ZNF580; MYEOV2; TBCK; ZNF746; DCAF11; DCAF4; GTF2I; WDR81; KCNMB3; C10orf2; COPS7A; CHAMP1; PPP6R3; GPR75-ASB3; PLIN3; DHX16; C1orf27; WDR46; TRAF3IP2; FLNB; BRD8; THAP4; GPN3; STAU2; MTF2; TMED7-TICAM2; EIF4ENIF1; C16orf52; ASXL1; ENDOV; ZFHX3; BCAT2; SLC25A26; RBMX; PET117; ACIN1; DCAF17; SMIM12; LYRM4; TMEM41B; DTYMK; TMEM14C; NFKB1; SLC25A11; CD320; MKS1; DAG1; STARD3; IDE; ELAC2; BIRC2; ECI2; ERCC1; NDUFV1; TADA2A; PNPLA6; RBM28; LCORL; NDUFS2; UTP14A; CEP120; C22orf39; FHIT; MTIF3; HAUS4; DHX40; PIGX; SHMT2; HDAC8; WDR13; MPP1; SLC16A1; EIF2B3; FAM122B; TRAPPC1; AFF1; FAM104B; XIAP; RBM6; XPNPEP1; RAB35; RHBDD1; LEMD3; ATXN10; LPP; VARS2; SMYD3; TMED5; NSMCE4A; ATP5SL; LHPP; ANKRD50; TIMM17B; TRMT2B; TBC1D17; NDUFB4; ME2; NSUN5; CUL7; SLC35A1; TSPAN3; ARMCX5; CNDP2; TMEM48; IFT46; TXLNG; TMEM135; FAM21C; SCO2; STIM2; TJP2; CDK16; CDK17; ATAD3A; PGAM5; CXorf56; CHD8; FUS; LPPR2; SRGAP2; LAS1L; ZNHIT6; MIB2; GPR137; PIN4; LCOR; MFSD5; ATRAID; ZFAND1; LARP4; RBM41; SMPD4; UBXN6; FAM3A; STRBP; PET100; CAMTA2; UBAP1; MCFD2; TRIQK; PAPD7; PPARD; FGFR1OP2; VPRBP; NUDT16; CXorf40A; KXD1; RBFA; SETD9; MASTL; VANGL1; BAG1; RAB3GAP1; RRM2B; GOLGA3; MCPH1; NEO1; TECPR2; TK2; RAB40C; ZNF668; ZNF347; ZNF764; ZNF641; TSFM; PPARGC1B; SLC38A6; GGA3; GOLGA4; SEC23B; DPY19L3; ZNF555; YTHDF2; TFCP2; AAAS; CRBN; NKRF; MRRF; DGCR2; BANP; BRD7; SMG7; POLL; NCOA3; PCBP4; ZBED6; ARL13B; RABEPK; SAMD8; ARL1; ABHD16A; PPP2R2A; SUCLG2; CINP; RIF1; IFT27; KLF11; RANGRF; SRPR; SYCP3; MNAT1; ECI1; SF1; ZC4H2; ZFX; SYNJ2; MINPP1; SUFU; ATP6AP1; ATR; HADH; TIPARP; PIGT; CTTN; ZBTB33; PAFAH1B2; ZNF408; UHMK1; VDAC2; PEX11B; ESYT1; TMLHE; UBR2; CD99L2; GNL3L; PRMT7; KLHDC4; FLAD1; FBXL20; WDR44; PACSIN2; UQCC; NDUFS5; WNK1; NDUFC1; KIAA0430; RNF4; NCAPH2; NDUFA2; ZDHHC8; ACOX1; ZCCHC6; ZNF75D; FMR1; ARHGDIA; NIT1; MYNN; PFDN6; BAK1; DNAJC19; C1D; ATG16L1; FBXO11; DGCR8; TAF6; NCOR1; IKBKB; ZNF317; NCK1; DHX35; SMAD7; MRPS35; ORC4; HYI; FAM193B; ZMYM2; YAF2; IL6ST; SRSF11; SLC33A1; IPO8; ARPC1A; BCL2L1; GSTO1; SRSF10; CTCF; TNPO3; PSMD1; SIRT5; EML2; MSL3; RBBP5; SIRT6; SIRT2; TMEM127; VIPAS39; C9orf3; MRPS18A; NUP62; EXD2; DIDO1; NDUFA11; UCKL1; PPP2R4; DDX3X; NSUN2; KANSL1; LIMS1; SLC1A4; REST; TTC27; SLC30A6; CHMP3; FAM65A; SCRN3; NEK4; FBXL5; ENY2; TUBD1; DHRS4L2; PEX19; POGZ; EIF4G1; MATR3; MEPCE; MR1; PPIE; TMEM184B; ANKRD28; PTP4A2; COG4; NASP; CCDC107; YIPF6; DENND1B; APTX; SERPINB6; USB1; RAB9A; SRSF2; MICU1; CHMP5; CLINT1; CAMTA1; DICER1; SEPHS1; ZNF865; TOPORS; MLLT10; VAPB; THAP3; HSDL2; ANKHD1; ZFP91; MLL; GCLC; IRF3; BCL7B; ORC3; GABPA; MCL1; HIRIP3; ARNT; OXR1; ATP6VOC; JMJD7-PLA2G4B; ARHGEF12; LEPROT; RBBP7; PI4KB; CUL2; POU2F1; ARPC4-TTLL3; ASCC1; EIF4G3; MSANTD3; MSANTD3-TMEFF1; RBM14; RBM12; CCT2; RBM4; RBM14-RBM4; CPNE1; CAPN1; ATP5J2-PTCD1; YY1AP1; ATP6V1F; ABCC10; RNF103; RNF103-CHMP3; TMEM110-MUSTN1; NFS1; DCTN5; CDIP1; C15orf38-AP3S2; NT5C1B-RDH14; TBC1D24; TRIM39-RPP21; RPP21; COPS3; TANK; AMMECR1L; KAT7; USP19; PSMC5; MLST8; CCNH; ARMC6; TBC1D23; AK2; GPANK1; TOR1AIP2; UCHL5; CABIN1; LRBA; UIMC1; CNOT2; BLOC1S5; FPGT; RPL17-C18orf32; GBF1; RNF145; NEK1; TRAF3; NIP7; PDCD2; ISY1; ZSCAN9; C20orf24; TGIF2-C20orf24; SUN2; PTK2; PMF1; PMF1-BGLAP; SLC4A2; DHX33; PPP2R5A; PSMA5; CPD; POC1B; PSMB2; INTS7; GGCT; MDP1; NEDD8-MDP1; SMURF1; DAP3; AK3; BCL2L2-PABPN1; KIF16B; MARK4; GLRX3; B4GALT3; HYPK; PDK2; PGM3; SIAE; SESN1; DOPEY1; SH3GL1; NDUFB5; UQCRB; NDUFB6; GCFC2; SAFB; HMGN3; RNF14; RNF7; ZNF778; GORASP2; ZNF513; C18orf21; EIF2D; CORO7-PAM16; PIGO; RBM15; PLRG1; SEC22C; ASB3; ASB6; AKR1A1; TRMT1L; PRDX1; C10orf137; ZMYND11; RPS10-NUDT3; UBE2E1; HSPE1-MOB4; UBE2G2; UBE2H; CTDP1; CUX1; SYNJ2BP-COX16; PIGV; CHURC1-FNTB; WBSCR22; MTA1; NDUFC2-KCTD14; IL17RC; NDUFC2; COMMD3-BMI1; CHURC1; UBE4A; COX16; PPT2; MBD1; SPHK2; MDM4; ZHX1-C8ORF76; SRP19;

ZNF670; SCARB2; PPP5C; ZNF664; PRPS1; BIVM-ERCC5; CCPG1; PSMC2; RBAK; RBM10; EIF4A1; RBAK-LOC389458; KIFAP3; RFC1; ZNF587; LIPT1; ANO10; TNFAIP8L2-SCNM1; SCNM1; TCEB1; URGCP-MRPS24; NPEPL1; BAG4; ISY1-RAB43; BNIP1; TTF1; KLF9; USMG5; MAVS; CAPZB; POLR1D; CHTOP; AKIP1; SH3GLB1; IGSF8; PRKAG1; NSFL1C; GTF3C3; ARID4B; MAP2K5; KAT5; RAB11A; TGOLN2; STRADB; FAM115A; DHPS; HNRPDL; PTPN2; M6PR; RNF40; PRMT1; ATRN; BACE1; VWA9; BZW1; C1QBP; ZNF48; CAMK2D; CASP6; CASP7; CASP9; CCNT1; CCNT2; PITRM1; ATAD2B; ODF2; ANAPC13; TWF1; WDR20; PIK3R1; EIF1AD; ZSWIM8; MIF4GD; MFSD11; NCOA6; ANAPC16; MAP4K4; RIN2; TMEM147; RBM39; RAB2A; AHCYL1; LOC100289561; ZNF691; TRIM26; BRF1; NUP93; ZNF322; ZNF790; DEF8; RNF41; ARFGAP2; AP2A2; RNF146; ARFIP2; ELP2; CARKD; ZBTB17; ZKSCAN3; PPP6R2; AKAP1; MPPE1; ASCC2; ZFAND6; EIF3L; ZNF410; SNX1; AKT2; PLD2; NFKBIB; PDE8A; TAF1C; PIM1; INPP5F; HIP1; RANBP6; PES1; NARS2; TIGD6; HINFP; NUB1; CLCN3; GLRX2; CLEC16A; PDIK1L; MTMR2; CD2BP2; GFOD2; LETMD1; RAB6A; SETMAR; LAMTOR3; RGL2; C7orf49; POMGNT1; BTF3L4; CEP57; SMUG1; CHST12; TOB1; TRA2B; TPD52L2; HDLBP; PRPSAP2; PPP3CC; KIAA0586; APEX1; HBP1; TRRAP; C7orf55-LUC7L2; LUC7L2; IMMP2L; CHMP2B; STX5; GFPT1; RAD23B; TMEM126A; FOXP1; DLST; PRPF4; TXN; PPP1CC; SEL1L; CTAGE5; ASAP1; TRIM3; NUDT9; SP1; USP4; ASPSCR1; APPL2; SLC30A5; PAPOLA; RAB5B; RAB5C; TAOK2; PCMT1; USP15; AP4E1; LSM4; GEMIN5; SEC24A; CEBPG; NT5C; TNIP1; URI1; ACSS1; BBS4; CDC5L; RPL15; ZNF444; SLC52A2; GMDS; AP4B1; YME1L1; UXS1; MED27; TBC1D1; CYB5D2; CREB3L4; PNPLA8; PSMC3IP; PIK3CB; ANKRD26; C9orf72; ATF2; NAA10; TRIM65; CERS6; ARL8A; CSE1L; TMCO1; ZNF620; ANKRD11; SNX12; ARAF; ETS2; STK3; PTGES2; CHD1L; UBE2L3; MCMBP; LRRC39; NOL8; ELOVL1; SLMO2; KDM2A; LRRC42; RAB18; CPSF3L; KAT6B; WDR92; GOLGB1; MAN2C1; SSBP1; C9orf69; SLC25A1; NOP16; PCGF5; MPP5; PPFIBP2; RPL10; C1orf5; TUBGCP2; R3HCC1L; NR1H2; FAM193A; DPP3; STOML1; KIAA0391; CSNK2A3; PRDM11; ANAPC10; CCT4; USP39; CNOT10; TMEM161A; GAPDH; RIT1; PAF1; SMG6; LOC100862671; POLD1; BTRC; RNF34; SRI; DDX21; CLCN6; CCDC51; FBXW7; NDUFB3; COX14; ITCH; DDX56; POM121; DDX6; CUL3; DIS3L2; HNRNPH1; SCFD1; ABCG2; CD63; TRMT2A; CCDC132; ANKFY1; COPS4; SERINC4; POLR3E; HARS; MIS12; NDUFA12; SPATA20; IDH3B; FAM173B; SMS; TARS; FBXO18; FASTK; CDK8; WDR4; ZNF155; SLC9A8; RDX; SRP68; CDK9; CALCOCO2; NOL10; PSMD9; TSN; SFSWAP; DCTN2; LPIN1; AARSD1; ADAM15; NSRP1; PDPK1; AP3D1; TBRG4; BRE; MORF4L1; CNOT1; MZF1; LARP7; ARMC8; PSME3; SNX17; PEMT; PDCD6; EIF3C; TOR1AIP1; UBOX5; FAM189B; ITPA; SRP72; CCDC61; ARSG; ING1; IFT20; AMBRA1; PAAF1; ILF2; EIF6; SLC12A9; ZNF839; CLOCK; SLIRP; HSD11B1L; SHOC2; CHD1; TMEM254; ANKRD46; FAM73A; RXRB; MAP4K3; PSMD5; CDK2AP1; UBE3B; WWP2; MCM3; PPP2R5D; PSMB6; PSMD11; CAMKK2; TAF11; RPL13A; LATS1; DAAM1; MED23; STOM; RNF111; WTAP; MED4; JOSD2; MARCH6; MCU; ARHGAP12; BCL2L13; NTAN1; STRIP1; TFAM; MEAF6; HAUS6; TRAPPC6A; TRAPPC3; UCHL3; NOSIP; IST1; ZFAND2B; MAX; VPS72; PCED1A; RAP2C; FAM173A; TTC19; EMC1; C21orf2; PEX11A; DNAJC10; LOC100129361; PPME1; HERC3; STX10; PPP1R12C; RQCD1; ZNF138; MTCH1; NSA2; LOC441155; PYCR2; SLC35A3; ABCB7; MKRN2; FBXO38; COPZ1; APEX2; AP3B1; PSMD6; DYNC1I2; MED21; DCLRE1A; PRE-LID1; RSRC1; RCN2; IKZF5; ZNF700; CDK2AP2; RRAGC; GTF2H3; AAR2; CUEDC1; KHDRBS1; AAGAB; TARS2; SEC11A; CEP164; RMND1; MEGF8; SLC39A1; HSP90AB1; STK25; PUS3; RAB4A; DOCK7; EPC1; LRRC14; RPS6KB1; TRAP1; C16orf91; MRFAP1; SHISA5; ABHD10; QARS; USP10; STX4; CHD4; WDTC1; RGS3; MBD4; PPIP5K2; PRKAR1A; NISCH; PPP1R3E; YOD1; C18orf8; USF 1; ESF 1; UNKL; SEC16A; KPNB 1; ELF2; LONP1; CHUK; CIRBP; TB CB; AP1S1; AP3S1; CLNS1A; CLPTM1; CREBL2; MAPK14; CSNK1G2; CSNK2B; CSTF3; CTSO; CTSZ; DAD1; DGKQ; DARS; DHX9; DHX15; DECR1; DNASE2; DYNC1H1; DPAGT1; DPH1; DRG2; DYRK1A; ECH1; EEF1G; EIF2B1; EIF2S3; EIF4B; ELAVL1; ENO1; EP300; FBL; EXTL3; XRCC6; BLOC1S1; GDI1; GTF2B; GTF2H4; GTF3C1; HDAC2; HSBP1; DNAJA1; NDST1; ICT1; IL13RA1; ING2; INPPL1; EIF3E; AARS; ACVR2A; PARP1; AKR1B1; APEH; TRIM23; ARF4; ARF5; ARF6; RHOA; ARVCF; ATF4; ATP5B; ATP5F1; ATP6V1C1; ATP5O; AUH; POLR3D; BPGM; BSG; CAT; CBFB; CDK7; CENPB; CENPC1; CLTB; SLC31A1; COX4I1; COX5B; COX6B1; COX7A2; COX7C; CSNK1D; CSNK2A1; CTNNA1; CTPS1; CTSB; CTSD; CYC1; DBT; DDB1; DLAT; DR1; DUSP7; E2F4; EEF2; EIF5; ELK4; STX2; ESD; ETV6; EYA3; FAU; FKBP3; FKBP4; FNTA; FNTB; FTH1; KDSR; GAB1; GABPB1; GARS; GCLM; GNAQ; GNB1; GNS; GOLGA1; GOT2; GTF2E2; GTF2F1; GTF3A; H2AFX; H2AFZ; HTT; HIVEP 1; HMGB 1; HNRNPA1; HNRNPA2B 1; HNRNPK; HSPA4; HSPD1; HSPE1; IARS; ID2; ID3; ACO1; IRF2; ITGAE; ITGB1; ITPR2; JAK1; KPNA1; KPNA3; KPNA4; TNPO1; IPO5; LIG3; LRP1; LRP3; LRP6; LRPAP1; MAGOH; MAN2A1; CD46; MDM2; MAP3K3; MGAT2; MGMT; MIF; MAP3K11; MPI; MPV17; MSH3; MAP3K10; MTAP; MTRR; MTX1; MVD; NUBP1; NBN; NCBP1; NDUFA4; NDUFA6; NDUFS4; NDUFS8; NFX1; NFYA; NME3; NRAS; NTHL1; NUP88; NVL; TBC1D25; OAZ2; ODC1; OGG1; ORC5; OSBP; PEBP1; FURIN; PAK2; PBX2; PCNA; PDE6D; PERI; PEX10; PEX13; PFDN1; PFDN4; PFDN5; PFKL; PHB; SLC25A3; PHF1; PIGA; PIGC; PIGF; PIK3C2A; PIK3C3; PI4KA; PMM1; PNN; POLA2; POLR2E; POLR2G; PPAT; PPP1R7; PPP1R8; PPP1R10; PPP2CA; PPP4C; PREP; PRKACA; PRKCI; MAPK1; MAPK6; MAPK7; MAPK8; MAP2K1; MAP2K3; PRP-SAP1; PSMA2; PSMA3; PSMA6; PSMA7; PSMB1; PSMB3; PSMB4; PSMB7; PSMC1; PSMC3; PSMC6; PSMD2; PSMD3; PSMD4; PSMD7; PSMD8; PSMD10; PSMD12; PSMD13; PSME2; PTBP1; PTPN1; PTPN11; PTPRA; RAD1; RAD17; RAD51C; RAF1; RALB; RANBP1; RANGAP1; RARS; RASA1; ARID4A; RCN1; NELFE; RECQL; UPF1; REV3L; RFC2; RFC4; RFNG; RFX1; RGS12; RING1; RNASEH1; RNH1; RORA; RPA1; RPA2; RPA3; MRPL12; RPN1; RXRA; SBF1; ATXN2; SDHB; SDHD; MAP2K4; SRSF3; SGTA; SKI; SMARCA2; SMARCC1; SMARCD1; SMARCE1; SNAPC1; SNAPC4; SNRNP70; SNRPB; SNRPB2; SNRPC; SNRPE; SNRPF; SNRPG; SNX2; SP2; UAP1; SPG7; SPTBN1; SRM; SRP14; SRPK1; SSB; SSR1; SSR2; SSRP1; STAT3; STIM1; STRN; SUPT4H1; SUPT6H; SUPV3L1; SURF1; SUV39H1; ADAM17; TAF2; TAF4; MAP3K7; TAPBP; TBCC; TCEB3; TCF12; TDG; TERF1; THOP1; SEC62; TRAPPC10; TOP1; TPP2; TPR; TPT1;

NR2C2; TSPYL1; TSSC1; TSTA3; TTC1; TUFM; HIRA; TYK2; UBA1; UBE2A; UBE2B; UBE2D2; UBE2D3; UBE2G1; UBE2I; UBE2N; UBE2V2; UNG; UQCRC1; UQCRC2; USF2; UVRAG; VBP1; VDAC1; XPO1; XRCC4; YY1; YWHAB; ZNF7; ZNF35; ZNF45; ZNF76; ZNF91; ZNF131; ZNF134; ZKSCAN1; ZNF140; ZNF143; ZNF189; ZNF202; USP7; STAM; CUL5; MLL2; TAF15; NRIP1; TMEM187; AXIN1; HIST1H2BC; PIP4K2B; ULK1; EEA1; ANXA9; STX7; VAPA; ZNF282; DUSP11; CUL1; TTF2; SMARCA5; OFD1; PPM1D; RANBP3; PPFIA1; PARG; NDST2; IKBKAP; HAT1; DGKE; CAMK1; AGPS; BLZF1; MAPKAPK5; PRPF18; DEGS1; DENR; YARS; RRP1; KHSRP; AKR7A2; NOP14; RUVBL1; USO1; CDK13; RFXANK; SSNA1; NCOA1; TNKS; EIF3A; EIF3D; EIF3F; EIF3G; EIF3H; EIF3I; EIF3J; BECN1; MRPL40; B4GALT4; MBTPS1; EDF1; CTSF; SNX4; SNX3; EED; RNMT; RNGTT; GPAA1; RIPK1; CRADD; TNFSF12; ADAM9; CDS2; RIPK2; FADD; SNAP23; NAPG; NAPA; MTMR1; RIOK3; TNFRSF10B; DYRK4; SUCLG1; SUCLA2; CREG1; TRIM24; DPM1; DCAF5; DPM2; SAP30; CES2; TMEM11; HDAC3; KAT2B; SGPL1; FUBP1; ZNF259; MCM3AP; EIF2B5; EIF2S2; CPNE3; BUD31; PRPF4B; TIMELESS; HERC1; MBD3; MBD2; ST13; FUBP3; TOP3B; WASL; ATP6V0E1; SLC25A14; RPS6KB2; RNF8; UBA3; UBE2M; BTAF1; AIP; CLK2; RHOB; ATIC; ATOX1; BYSL; CCNG1; CDKN1B; AP2S1; COX8A; CRY1; CS; TIMM8A; DUSP3; ECHS1; EIF2S1; EIF4EBP2; FDX1; FEN1; GMFB; GPS1; GTF2F2; HSPA9; IDH3G; IREB2; NDUFB7; NINJ1; OAZ1; PRKAR2A; RAB1A; RAB5A; SDHA; SNRPD3; TARBP2; UXT; PIGQ; FIBP; EBAG9; RAB11B; UBE2L6; MFHAS1; CYTH2; MED14; SOCS6; ZNF235; TRIP12; TRIP11; JMJD1C; MED17; MED20; PIGL; PMPCB; GTPBP1; NFE2L3; MTRF1; ACTL6A; ACVR1B; ARHGAP1; ARL3; ASNA1; BAD; BCL9; BNIP2; BPHL; BRAF; PTTG1IP; CAD; CALR; CASP3; CD81; CDC34; COX6C; COX15; CREB1; CTBS; DDX5; DDX10; DFFA; RCAN1; DVL2; DVL3; E4F1; PHC2; ENDOG; ENSA; EPRS; ERH; ESRRA; ACSL3; ACSL4; BPTF; FARSA; FDFT1; FLOT2; FRG1; GALNT2; GOLGA2; GPS2; ARHGAP35; GTF2A2; HNRNPAB; HNRNPU; HUS1; IDI1; FOXK2; MGST3; MOCS2; NARS; NDUFA1; NDUFA3; NDUFA10; NDUFB1; NDUFB2; NDUFB10; NDUFS3; NDUFS6; NFATC3; YBX1; PARK2; PET112; PEX14; PIGH; PSPH; RABGGTA; RABGGTB; RPS6KA3; SCO1; SNRPA; SNRPD2; SREBF2; TAF1; TBCA; TOP3A; TRAF6; TTC4; RAB7A; PRRC2A; DDX39B; PABPN1; C21orf33; BAP1; CDC23; HERC2; PIAS2; MTMR6; MTMR4; ATP6V0D1; PRPF3; FAM50A; RRP9; PRKRIR; ATG12; PDCD5; HGS; NEMF; PCSK7; COX7A2L; SCAF11; AP4M1; ZW10; ETF1; MTA2; NOLC1; MAPKAPK2; ITGB1BP1; COPB2; ZNHIT3; MED1; B4GALT5; CNOT8; VAMP3; SNAP29; TXNL1; PPIG; KIF3B; TM9SF2; CIAO1; POLR2D; HS6ST1; NMT2; PEX16; SNRNP40; DDX23; SYMPK; EIF2AK3; SH3BP5; EIF4E2; ATG5; ROCK2; STX8; PIGB; CLTC; FXR2; MPDU1; TMEM59; CIR1; APBA3; ATP6V1G1; SPAG7; MRPL33; SEC22B; PRDX6; VPS9D1; SEC24C; ACTN4; MRPL49; DDX1; DHX8; MTOR; KRAS; MARS; MYO1E; NDUFA5; NDUFA7; NDUFA9; NDUFAB1; NDUFB8; NDUFB9; NUCB2; OXA1L; PCYT1A; PFN1; PGGT1B; PIK3R2; POLR2K; POLRMT; PPID; PRCP; PWP2; ABCD4; SFPQ; SIAH2; TLE1; TRIM25; NUP214; ZRSR2; SLC27A4; ZMYM4; RBM8A; OXSR1; WDR1; GOLGA5; MVP; THRAP3; MED12; MED13; NUP153; CCS; DOPEY2; THOC1; SART1; ABL1; ATF1; BMI1; CHKB; CRK; CRKL; DDOST; ERCC4; GAK; GFER; GLUD1; GNB2; RAPGEF1; PDIA3; HCFC1; HINT1; ZBTB48; HSPA5; JUND; SMAD4; NCL; NFIL3; NKTR; NUP98; PDCL; PHF2; RALA; ROCK1; SLC20A1; STAT2; YES1; CCDC6; MLF2; SMC3; ZRANB2; MED6; ACOT8; GNPDA1; MED16; PIGK; RANBP9; UBA2; CFL1; DMXL1; DOM3Z; GTF2E1; HSF1; DNAJC4; IDH3A; IFI35; IFNGR2; INPP5A; INPP5B; LAMP1; LMAN1; ALDH6A1; MRE11A; RBL2; RHEB; SRSF4; SOLH; SOS1; TAF13; TARBP1; ZNF354A; TCF20; TERF2; NELFA; EVI5; REEP5; TAF1B; SOX13; FARSB; ABCC5; DNM1L; ABCF2; COX17; SCAMP2; SCAMP3; ERAL1; TSSC4; PDCD7; GIPC1; ARPC3; ACTR3; PPIF; CTDSP2; ARPC2; RAD50; ACTR1B; ACTR1A; ZNF263; PDIA6; ARIH1; NAMPT; AKAP9; G3BP1; CEBPZ; TRIM28; ATP6AP2; LPCAT3; RCL1; CNIH; RBM5; LHFPL2; ALYREF; TXNDC9; MPHOSPH10; NME6; NUTF2; USPL1; EIF1; FLOT1; PSMD14; PRDX2; PRKD3; SLC35B1; DCAF7; AP3S2; MRPS31; POP7; SRRM1; STAM2; SF3B4; ZMPSTE24; AKAP8; PURA; STUB1; STAG1; SIGMAR1; CWC27; SAP18; SMNDC1; BCAS2; EIF1B; DNAJA2; APC2; KATNB1; ACAT2; CAPRIN1; NBR1; MCM1; MDH2; MAP3K4; MFAP1; MIPEP; MLLT1; MTHFD1; NAB1; HNRNPM; NAP1L4; PRCC; RNF6; TSPAN31; TBCD; TSNAX; UQCRFS1; UQCRH; CLPP; LAGE3; ARID1A; ALKBH1; CDC123; H1FX; PCNT; CDC42BPB; HDAC6; SNAPC5; DSCR3; SMYD5; RRAGB; AGFG2; TUBA1B; IK; IRF9; BPNT1; PIAS3; LUC7L3; TAB1; MAN2A2; TMEM50B; CAPZA2; DYNC1LI2; NEDD8; NFYB; NUCB1; NUMA1; ORC2; PA2G4; PCBP1; PCM1; PIK3CA; PIN1; PITPNA; POLE; POLR2H; POLR2I; POLR2J; PPP2R5B; PPP2R5E; PRKAA1; PRKAB1; PKN2; DNAJC3; PSME1; RAD21; RANBP2; DPF2; SRSF6; ITSN2; TAF10; TESK1; TSG101; VARS; XRCC1; ZKSCAN8; SHFM1; ANP32A; SMC1A; NPEPPS; PCGF3; CDIPT; PGRMC2; ARIH2; TUBGCP3; CFDP1; RAN; TIMM23; LYPLA1; EMG1; TIMM17A; ZER1; HMG20B; MERTK; SLC30A9; PIBF1; PPIH; ZNHIT1; TIMM44; ZBTB18; TADA3; UBE2E3; EIF3M; SEC23A; CREB3; LRRC41; VTI1B; ENOX2; APPBP2; CIB1; CHERP; IPO7; NOP56; SSSCA1; RNASEH2A; ANP32B; LAMTOR5; AGPAT1; SPTLC1; ARFGEF2; ARFGEF1; RABAC1; SLU7; SIVA1; MRPL28; NPC2; TXNRD2; DRAP1; DNPH1; PRPF8; PAIP1; TBL3; MXD4; HEXIM1; RBCK1; STAMBP; POLR3F; POLR3C; IVNS1ABP; TAF6L; ATP5L; GNAI3; LGALS8; POLH; PSMC4; TRIM27; RSC1A1; SARS; DYNLT1; DYNLT3; TFE3; SLBP; YEATS4; ELL; NCOA2; SPHAR; EXOC5; NPRL2; MTX2; YKT6; PMVK; FARS2; CGRRF1; RRAGA; DCTN6; GNA13; MAP4K5; GMEB1; CCT8; POLD3; HSPA8; SLC12A7; NUDC; PTGES3; MAP3K2; ZBTB6; POP4; VAMPS; ZNF460; RPP40; SDCCAG8; CLPX; SRCAP; JTB; MAN1A2; TXNL4A; NUDT3; GLO1; EHMT2; COPSE; RNPS1; SUB1; SMPDL3A; DIAPH2; PSKH1; SURF6; SYPL1; TALDO1; TCEA1; YWHAE; IFRD2; LZTR1; LMO4; DDX18; QKI; ZFPL1; WDR3; MALT1; RALBP1; PRDX3; AFG3L2; KDELR1; SF3A3; HNRNPA0; SEC61B; SERINC3; PNRC1; PSMF1; TMED2; STIP1; CKAP4; YWHAQ; TMED10; ASCC3; UQCR11; COPSE; GCN1L1; COPS5; METAP2; SF3B2; ILVBL; SNRNP27; TMED1; LIAS; CALM1; MYO9A; PPA2; RAC1; RBBP6; RNF5; RPE; SDF2; ST3GAL2; SKIV2L; SKP1; SUMO3; SNRPD1; SOS2; ZNF33A; ZNF33B; ZNF12; ZNF17; ZNF22; ZNF24; ZNF28; ZBTB25; RNF113A; NPM3; SLC35D2; ADRM1; NUDT21; CPSF6; RTN4; DDX52; WWP1; CYB561D2; TMEM115; DUSP14; TOPBP1;

RER1; HNRNPUL1; KRR1; FAF1; POLR3A; CLASRP; KPTN; PWP1; CDC37; FICD; LSM6; ATP5I; RPL10A; UBL3; SSR3; TCEB2; TEP1; TFDP1; TMF1; TRIO; UTRN; VCP; ZNF41; VEZF1; ZNF175; ZXDA; ZXDB; SLMAP; ZMYM6; TESK2; NUP50; C14orf1; STRAP; CEP250; WBP4; ABCB8; SEC23IP; SUPT16H; POLI; PROSC; AKAP10; MRPL3; RPL35; PRAF2; SEC63; HPS5; RNF139; DCTN3; XPOT; CHP1; PXMP4; DUSP12; SNF8; ATXN2L; SYNRG; PNKP; B4GALT7; VPS45; LYPLA2; COPE; STXBP3; TUSC2; CBX3; EXOC3; GABARAP; RNF13; TWF2; GABARAPL2; STAT1; NUPL2; ZNF236; OGFR; ATF6; PAXIP1; CASC3; RALY; BRD3; DDX42; TARDBP; COMMD3; CCT5; DGAT1; ELL2; PGLS; ABCB10; MACF1; ADAT1; PRDX5; AP3M1; APPL1; CD3EAP; DNPEP; ARL2BP; AHSA1; CCRN4L; CD2AP; COPG2; FAM50B; AATF; SERGEF; CCNDBP1; FBXL3; FBXL4; FBXL6; FBXW2; FBXO22; FBXW8; FBXO3; FBXO8; FKBP8; TIMM10B; EIF2C1; GRHPR; GTF3C4; HNRNPH3; HARS2; MID2; NUBP2; MSRB2; POMZP3; PRDM2; RYBP; SCAP; SNW1; XRN2; ZNF212; HACL1; RHBDD3; ZNF346; FTSJ1; KEAP1; G3BP2; FBXW11; KIN; KPNA6; LETM1; PLA2G15; PIGN; DNAJB9; GTPBP4; NUFIP1; FBXO9; TTC33; BLOC1S6; PEF1; PFAS; PFDN2; CDK14; PITPNB; ANP32C; ICMT; PRDM4; ZMYND8; H2AFV; RAB3GAP2; RLF; RSU1; SF3B3; SEC22A; SNAPIN; STAT5B; TIMM10; TIMM13; TIMM8B; TIMM9; ATP6V0A2; PRPF6; TXN2; UCK2; WBP1; WBP2; YWHAG; ZNF281; EIF3K; DNAJC15; N6AMT1; C16orf80; VPS4A; HTRA2; NXT1; TBK1; SAP30BP; VPS51; MAT2B; POLM; GNL2; RBM15B; CPSF1; TRA2A; SAC3D1; CCDC106; EEF2K; SNX15; PRRC2B; UBIAD1; SNX8; SNX11; ATG4B; PAXBP1; NME7; GMPPB; GMPPA; SEC61A1; TIMM22; ALG6; TFPT; KCNJ14; NENF; CNOT7; ZNF225; ANAPC2; ANAPC4; ABT1; DPP7; PREB; NRBP1; FTSJ2; USP25; UBQLN1; STOML2; ST6GALNAC6; UBQLN2; BAZ1A; BAZ2A; BAZ2B; DHX38; CCDC22; SNRNP200; DEXI; SACM1L; MRPS28; WDR37; DCPS; OSTM1; ASF1A; SNX24; SPCS1; ANAPC15; UNC50; MRPS18B; C19orf53; MKL2; ACAD9; MRPL42; NOB1; NTMT1; ASTE1; FAM32A; MRPL13; ZNF770; C16orf72; ZC3H7A; ZBTB44; SETD2; MRPL18; NDUFAF4; CCDC59; METTL5; CHMP4A; GTPBP8; CRIPT; MRPL15; TIMM21; LGALSL; ORMDL; DYNLRB1; CNIH4; TMEM208; SSU72; AP2A1; TMEM258; NDUFA8; PPP2R1A; VAMP2; HSD17B8; UBL4A; GNPAT; EIF2B2; RAPGEF2; RBX1; TMEM5; CNPY2; C11orf58; MGAT4B; DNAJC8; SUCO; EXOSC2; NOMO1; TRAM1; CAPN7; ETHE1; BRD4; ISCU; TGDS; C22orf28; TMEM50A; KLHDC2; PDSS1; PATZ1; EDC4; PPIL2; PISD; MTCH2; ZNF318; TBC1D22A; ZNF324; HIBCH; GNL3; FAM162A; AKAP8L; RNF11; ACAD8; DIEXF; PELP1; SND1; GHITM; VPS41; UQCRQ; ZBTB11; AFF4; INVS; SNX5; TUBGCP4; CHMP2A; RNF115; KLHL20; LSM1; LSM3; DIMT1; ZNF330; TNRC6A; GOLIM4; PRPF19; UTP20; RABGEF1; TOR1B; MCAT; CNOT3; ZNF232; TMOD3; ZKSCAN5; LATS2; BRD1; ERO1L; ZNRD1; DNTTIP2; MAGED2; PIK3R4; UBXN4; MDN1; FAM120A; FAF2; PSME4; ATP11B; ZNF592; SH3PXD2A; CTR9; TTC37; MDC1; SAFB2; SLC25A44; TTI1; PHF14; KDM4A; UBE3C; EMC2; KIAA0100; KIAA0355; AQR; TMEM63A; CEP104; SART3; USP34; SETD1A; LAPTM4A; SLK; MLL4; MLEC; KIAA0195; EIF4A3; TM9SF4; MTSS1; SPCS2; BMS1; PTDSS1; SERTAD2; MAML1; SNX19; TATDN2; MRPL19; TOMM20; EFCAB14; URB2; TSC22D2; ARHGEF11; ZBTB24; PLEKHM1; C2CD5; ZNF518A; EPM2AIP1; C2CD2L; FARP2; CEP350; LRIG2; PJA2; TOMM70A; SEC24D; FCHSD2; URB1; ZC3H11A; TOX4; DDX46; ZBTB39; OSBPL2; ZBED4; FIG4; KIAA0196; AP5Z1; DENND4B; SUPT7L; FAM20B; RNF10; ZBTB5; JOSD1; HELZ; KIAA0020; N4BP2L2; PDAP1; SCAF8; ZFP30; DOLK; AAK1; LMTK2; ICK; R3HDM2; ZNF510; PPP6R1; MLXIP; TRAPPC8; MON1B; MORC2; ZHX2; KIAA0907; BAHD1; DHX30; TCF25; PDCD11; PCNX; HMGXB3; RALGAPA1; WDFY3; RAB21; SPEN; FBXO21; EXOSC7; KDM4B; USP33; PHLPP2; ZNF292; XPO7; MON2; PDXDC1; FRYL; PDS5B; ZHX3; KIAA0754; PIKFYVE; ZNF609; TBC1D9B; GGA2; WAPAL; SETX; SETD1B; FTSJD2; ERP44; RRP1B; MYCBP2; AVL9; PPRC1; ZC3H13; SARM1; CDK12; MRPS27; CUL9; FAM179B; SMG1; TAB2; PLXND1; ATG2A; RAD54L2; SMC5; MAST2; ZZEF1; ANKLE2; ZC3H3; GRAMD4; CIC; TBC1D9; WDR43; SNX13; MPRIP; NUP205; EFR3A; RTF1; TTLL12; METAP1; ZCCHC14; CEP68; PHF3; LARP4B; RCOR1; FAM168A; PMPCA; PLEKHM2; ZC3H4; RRS1; PRRC2C; TBC1D12; DNAJC9; KIAA0556; RPRD2; ATP11A; DNMBP; POFUT2; CLUH; NUP160; CSTF2T; ATMIN; KIF13B; FKBP15; SIN3B; NCAPD3; DNAJC13; MAN2B2; KIAA1033; USP22; DPY19L1; SZT2; WDR7; VPS39; DNAJC16; KHNYN; ANGEL1; USP24; FNBP4; KIAA1109; LARP1; PPP1R13B; PUM2; UFL1; RRP8; KIAA0947; SMGS; MAU2; NCSTN; NUDCD3; MED13L; ZDHHC17; ADNP; LARS2; PPWD1; ZFYVE26; TMEM131; GLTSCR1L; POFUT1; SUZ12; SCRIB; MORC3; SKIV2L2; R3HDM1; ELP5; PANX1; VPS13D; SAMM50; HECTD1; NIPBL; YIPF3; TECPR1; DCAF12; ABHD14A; EP400; C3orf17; DCAF13; TMEM186; AASDHPPT; POLR1A; CCDC28A; AHCTF1; CAMSAP1; CNOT6; NELFB; ZDHHC5; MTMR9; ATL3; NOL11; PTPN23; NIPSNAP3A; HEATRSA; FAM98A; SLC22A23; KBTBD2; SYF2; PNISR; KIAA1429; NECAP1; DHRS7B; IBTK; TBC1D10B; RNF167; C2CD3; DAK; ZZZ3; RPAP1; LRIG1; UPF2; PTCD1; GLCE; OPA1; UBXN7; LTN1; POLDIP2; GPATCH4; HERC4; CCDC9; CCZ1; LDLRAP1; PRPF31; EPC2; GAPVD1; TRPC4AP; IRF2BP1; C10orf12; NAT9; ZNF337; NOC2L; RSL1D1; GTPBP5; SENP3; TRUB2; WWC3; ZNF777; BRPF3; COQ2; GPKOW; MMADHC; RRP7A; DESI1; SGSM3; GLTSCR1; DCAF8; WARS2; UBXN1; GTF2A1; ZNF593; AZIN1; MBTPS2; PCF11; CDC40; ZBTB7A; UBR5; EIF5B; TRIM33; LAP3; NBAS; WDPCP; TXNDC12; TXNDC11; POPS; RPS27L; POMP; TMA7; NOP58; NMD3; TRMT6; ATP6V1H; MTERFD1; SLC35C2; PELO; GET4; MRPL2; DERA; MRPL4; APIP; CUTC; FCF1; NDUFA13; ERGIC3; MRPS17; MRPS7; TAF9B; UBE2D4; HEBP1; ATP6V1D; ADIPOR1; UTP18; ABHD5; NDUFAF1; PHF20L1; TFB1M; UBE2J1; RBMX2; LACTB2; SUV420H1; TRAPPC12; RMDN1; MRPS2; COQ4; UTP11L; SBDS; C14orf166; DERL2; FAHD2A; EXOSC1; SF3B14; ISOC1; EMC9; MRPL11; MRPL48; TMBIM4; TPRKB; PPIL1; MED31; FAM96B; MRPS16; MRPS18C; FIS1; PAM16; MRPS23; MRPS33; GOLT1B; BOLA1; VPS36; PTRH2; TVP23B; GLOD4; CDK5RAP1; STYXL1; RBM7; RPL26L1; COMMD2; IER3IP1; NAA20; ZFR; TELO2; RLIM; TMEM66; COPG1; RAB10; INSIG2; CHCHD2; DYNC1L11; HSD17B12; COMMD10; WDR83OS; TRAPPC4; RAB4B; PIAS1; NOL7; HEMK1; SDF4; MRTO4; LSM7; NAA38; PDGFC; CPSF3; VPS28; TRAPPC2L; TRIP4; DBR1; POLK; MAN1B1; DDX41; SNX9; VPS29; NLK; BIRC6; FAM8A1; NAGPA; TUBE1; SELT; TAOK3; HP1BP3; PCYOX1; HSPA14; RSL24D1;

SS18L2; DNAJB11; POLR3K; ATPIF1; WBP11; RAB14; ZNF274; ZNF639; SRRM2; ZDHHC2; DDX47; TACO1; ACP6; WWOX; AKAP7; C9orf114; CTDSPL2; TRIAP1; C11orf73; CWC15; TRMT112; UFC1; RTFDC1; GLRX5; RNF141; GLTP; RTEL1; NCKIPSD; EMC4; TMEM9; CXXC5; ANKRD39; C20orf111; CCDC174; ZC3HC1; C9orf156; PDZD11; VTA1; TMEM69; MRPL37; RNF181; MRPL51; PBDC1; MRPL27; ZCCHC17; KBTBD4; SCLY; C9orf78; KLF3; TM7SF3; SCAND1; BFAR; COA4; BCCIP; ERGIC2; RSF1; TIMMDC1; KDM3B; ARMCX3; TDP2; KRCC1; ZNF644; MRPL35; WAC; MRPS30; GDE1; CRNKL1; STX18; POLA1; RWDD2B; SEPSECS; USP18; NUP54; PTOV1; CPSF2; POLE3; CHRAC1; MRPL39; TMED9; HAUS7; ARID1B; MPHOSPH8; POGK; CNOT11; FOXRED1; MIER2; INO80; ZRANB1; UBE2Q1; TRIM44; WDR5; ZC3H7B; MED29; BMP2K; VEZT; ZCCHC8; RNPC3; ALKBH4; C17orf59; CNNM3; CDKN2AIP; KCTD9; KLHL24; TRIT1; FTSJ3; CNNM2; DYM; KLHL28; GATAD2A; ANKRD10; ZCCHC10; OTUB1; TRPM7; GIN1; MCM9; FBXL12; ANKRD49; WDR55; PGPEP1; TASP1; ZNF3; CC2D1A; TMEM104; QRICH1; THUMPD1; ZCCHC2; DPP8; ST7L; CWC25; UHRF1BP1; ALKBH5; PNRC2; MTMR10; SLC39A4; LRRC40; PXK; TBC1D22B; CDKAL1; CHD7; FAM208B; FOCAD; BTBD2; YTHDF1; HEATR2; OSGEP; ZSCAN32; UBE2R2; CHCHD3; IMPAD1; RAB20; WRAP73; TRMT10C; EXD3; KANSL2; MARCH5; ADPRHL2; COMMD4; CECR5; FAM206A; MRPL16; SDHAF2; SLC48A1; TRNAU1AP; FAM120C; C1orf109; PARP16; SSH3; INTS8; C4orf27; THG1L; SLC25A38; SLC35F6; ZNF416; CLN6; PINX1; C1orf123; VPS13B; PRPF40A; DDX27; GID8; HIF1AN; TMCO3; PAK1IP1; LAMTOR1; ZNF446; TRMT61B; CDC37L1; C19orf24; PIH1D1; PPP2R3C; STX17; NPLOC4; PRPF39; C14orf119; DENND4C; GPATCH2L; PHIP; USP47; PTCD3; TRMT12; VPS37C; IWS1; NRDE2; MRPL20; RUFY2; SCYL2; TMEM248; RNF31; TRMU; ARGLU1; C10orf118; MED9; YEATS2; WDYHV1; GPATCH1; SAMD4B; WDR6; LUC7L; WDR70; ATG2B; GPATCH2; SLFN12; AGGF1; RBM22; MAGOHB; PLEKHJ1; MANSC1; WDR60; VAC14; TMEM39B; IARS2; PRPF38B; AKIRIN2; GPN2; ARHGEF40; HEATR1; TRIM68; CCDC94; LARP1B; SRBD1; IPO9; ELP3; WDR74; GSPT2; NLE1; THAP1; MTPAP; LMBR1L; SDAD1; WDR11; ARMC1; DARS2; TMEM33; TSR1; PNPO; SHQ1; MRPS10; INTS10; RMDN3; RNMTL1; SMG8; RNF220; RIC8B; SLC4A1AP; NADSYN1; DNAJC17; ASUN; RPRD1A; MAP1S; N4BP2; GOLPH3L; ATF7IP; DHX32; ARL8B; ZFP64; DNAJC11; HMG20A; TBC1D13; TMEM57; VPS35; ARFGAP1; PANK4; USP40; COA1; SMU1; UBA6; AP5M1; NUP133; SLC38A7; OGFOD1; CCAR1; AGK; TMEM184C; CCDC25; WDR12; TTC17; TYW1; TMEM39A; WDR41; ADI1; THNSL2; TMEM19; NUDT15; IMP3; PHF10; QRSL1; ZNF654; CWF19L1; EXOC2; BRF2; PBRM1; CCDC91; RNF121; BRIX1; DDX19A; RFK; C6orf70; RSAD1; FGD6; TMA16; C5orf22; ABCF3; UFSP2; LIN7C; RSBN1; BLOC1S4; LMBRD1; SYNJ2BP; LSG1; METTL2B; DCP1A; COPRS; ST7; PI4K2A; TMEM63B; RRN3; UTP6; BDP1; RNF130; FBXO6; IMPACT; VIMP; EMC3; CAND1; UBAP2; TMEM242; EAPP; PPP2R2D; BRK1; ITFG2; CISD1; PLGRKT; USE1; TEX2; ZC3H15; TMEM165; ACTR10; ASH1L; TMCO6; LRRC59; KIAA1704; CSGALNACT2; WSB2; NOP10; SLC35E3; ZNF395; VPS33B; RNF114; CMAS; BIN3; FAM114A2; DHTKD1; COG1; MAML3; TRPV1; SLC25A40; MKKS; PCDHGB5; CLN8; NANS; UBB; DAZAP1; BRWD1; TERF2IP; SLC38A2; YIPF1; GAR1; SSH1; RBM27; KCTD5; FBXO42; MRPS21; FBXW5; ETAA1; ANKIB1; MIOS; SMCR7L; TOLLIP; TMX3; HEATR5B; DHX29; EXOSC4; ELP4; PUS7; CCDC93; ASNSD1; MRPL50; FAM35A; TOMM7; WDR5B; DDX49; ING3; TRMT13; VSIG10; GTPBP2; LIN37; C19orf10; SMG9; ALG1; UBFD1; TMEM234; PPP1R37; MOSPD1; YLPM1; RNF20; GPCPD1; FAM214A; WDR45B; METTL3; GSK3A; CHST7; DIABLO; INPP5E; POLE4; LARS; UGGT1; UGGT2; KCMF1; TM9SF3; UBQLN4; WRNIP1; GRIPAP1; BDH2; TMEM167B; PNO1; SH3GLB2; STARD7; EMC7; C1GALT1; EXOSC5; MCCC1; NCLN; FEM1C; DUSP22; CMC2; MRPS22; YAE1D1; C11orf30; MFF; SDR39U1; XAB2; CCDC47; C5orf15; NIT2; OTUD7B; PARP6; RNPEP; FAM20C; PRDM10; PPAN; PSMG2; ADPRM; MRPL1; TOMM22; CHPT1; CCNL1; MNT; CIAPIN1; C16orf62; ANKMY2; RARS2; RALGAPB; ZMIZ1; RALGAPA2; NKIRAS1; ENTPD7; PCNP; PITHD1; PARP11; UTP3; AVEN; C12orf4; C12orf5; MAN1C1; PDSS2; SETD8; REXO4; NUP107; MRPL47; ATP13A1; DDX24; SCYL3; SEPN1; ATP10D; TUBGCP6; LYRM2; SNX14; YIF1A; GALNT1; MCOLN1; CSRP2BP; TMEM9B; MRS2; CLK4; RAB22A; ANKHD1-EIF4EBP3; REXO1; KIAA1143; GATAD2B; LRRC47; ZNF512B; ZNF490; USP31; PRR12; ATXN7L1; NLN; ESYT2; KIDINS220; MTA3; AARS2; INTS2; XPO5; ARHGAP31; SERINC1; UBR4; NUFIP2; MIB1; ZNF398; KLHL42; PDP2; USP35; KLHL8; TMEM181; ARHGAP21; CRAMP1L; KIAA1430; WDFY1; ZNF687; WDR48; FNIP2; PITPNM2; SLAIN2; RANBP10; KIAA1468; VPS18; ZBTB2; SH3RF1; PHRF1; RDH14; FLYWCH1; ALS2; ZSWIM6; KIAA1586; DDX55; CWC22; GBA2; DENND1A; KIAA1609; ANO8; METTL14; EPG5; NCOA5; PPM1A; DHRS4; DEAF1; UBC; RAP2A; ZNFX1; MBNL1; ZNF253; NDUFV2; KAT2A; NMT1; ZNF8; MTMR3; MRPS12; POLR2L; PPA1; PPIA; MRPL23; TNFAIP1; TRAF2; KDM6A; XRCC5; ZNF273; TMX4; GATAD1; KIAA1967; LSM2; CCNB1IP1; C6orf47; SLC30A1; SRPRB; ENOPH1; RPRD1B; ZNF77; PRUNE; SCAF1; SELK; RBM25; WIZ; RRAGD; SNX6; TRIM39; C21orf59; ZFYVE1; SENP2; PDLIM2; KLHL12; GPBP1L1; C12orf10; UTP14C; ZNF500; VPS11; SAV1; CCDC90B; FASTKD5; GUF1; SPCS3; RINT1; RIC8A; MIIP; EEFSEC; TRAPPC11; ZFAND3; SRR; PPP1R11; ZNF148; POLR2F; ZNF277; ITM2B; TIA1; FB; ABHD4; MRPL17; UBE2O; HEATR6; NSUN3; CERS2; GPATCH3; HPS4; GALNT11; ZNF335; MRPS14; PCIF1; FKBPL; RBM26; GOLPH3; MCCC2; SNX16; MAGEF1; TMBIM1; DUS1L; MRPL46; XYLT2; EIF4H; C11orf24; ZFYVE20; PDF; C17orf75; OSGEPL1; MMS19; DNAJC1; TFB2M; TOR3A; HERPUD2; NOC3L; RNF25; NSD1; LMBR1; XPO4; HS1BP3; IKZF4; ZMAT3; KLHL25; GZF1; C5orf28; TMEM168; ATG3; POLR1E; SUDS3; TTC31; NARFL; ZDHHC6; PCNXL4; ACTR6; MRPS25; DNMT3A; VPS52; GIGYF1; VPS16; ANAPC1; SNRNP35; DGCR14; COPS7B; NUCKS1; ACBD3; TNS3; FAM160B2; PARP12; ZNF574; SFXN1; IPPK; CCDC14; C6orf106; C11orf1; RMND5B; CERK; LMF1; OSBPL11; RMND5A; MPHOSPH9; ARV1; NMNAT1; MAP1LC3B; PORCN; MARCH7; YTHDC2; TUT1; MRPS11; RFX7; PAPOLG; C12orf43; ACTR8; CASD1; CCDC71; MRPL44; VPS33A; NOL6; KRI1; UPF3B; UPF3A; RSRC2; INTS3; FRY; ANKRA2; SPATS2; ZNF649; SELRC1; UBE2Z; C8orf33; CAPN10; ZNF747; FUNDC2; DDRGK1; MRPS34; MRPL34; CDK11A; MRP63; YIPF2; PRR14; C19orf43; CUEDC2; METRN; DDX50; DDA1; NUP37; SPATA5L1; PDCL3; ERI3; C7orf26; NABP2;

SECISBP2; NOC4L; METTL16; FASTKD3; TMEM109; C2orf49; ASB8; DCTPP1; C1orf50; CCDC86; C11orf48; WDR18; WDR77; SLC25A23; SMIM7; ALG12; C9orf16; TAF1D; DHX58; TMEM185B; FAM134A; PHF23; PPDPF; DHRS11; GNPTAB; NOL12; LENG1; C1orf35; RBM42; ZNF343; FBXL15; DCAF10; NDUFS7; PGS1; IRF2BPL; LRFN3; HAUS3; CYP2R1; PAGR1; C2orf47; GCC1; ATP13A3; ABHD8; NKAP; CDC73; CARS2; MRPL24; C10orf76; MUL1; RNF219; ADIPOR2; FAM118B; TANGO6; SNRNP25; C6orf211; OCEL1; ARMC7; OSBPL9; ROGDI; CHMP6; SRD5A3; PANK3; HECTD3; NLRX1; FN3KRP; C22orf29; ZDHHC14; MSANTD2; NAA35; YRDC; MANEA; OGFOD3; BBS1; PRKRIP1; NOL9; TBL1XR1; ZNF768; THAP9; PALB2; TEFM; AAMDC; BBS10; SNIP1; ASB13; ASB7; KATNBL1; TXNDC15; CCDC82; KLHL36; FBXO31; HPS6; TTC21B; PTCD2; CAMKMT; METTL8; ZMYM1; GEMIN6; NHEJ1; ZBTB3; TMEM180; CSPP1; RPAP2; CBLL1; RABEP2; UBA5; TGS1; GGNBP2; ZNF672; NUP85; EIF2C3; PYROXD1; ACTR5; MRM1; KIAA0319L; SLC35E1; OBFC1; ZCCHC4; C10orf88; RMI1; FAM192A; PHC3; WWC2; NAA25; UBTD1; TMEM62; PANK2; FBXL18; GFM1; KLHL18; ZNF606; MZT2B; VCPIP1; RPF1; THOC7; CENPT; USP36; CTC1; MUS81; WDR19; CHD9; PROSER1; CCDC92; TM2D3; NAA50; COQ10B; ACSF2; C17orf70; SIK3; SLC35F5; FAM214B; C16orf70; EDEM3; ITPKC; GRPEL1; MED28; DNAJC5; WDR82; WDR61; TNKS2; THUMPD2; NDFIP1; CYB5B; ZNF34; WDR59; KLHL15; INTS5; EEPD1; DUSP16; SH3BP5L; SETD7; ACAP3; KIAA1715; MAP2K2; RAI1; TMX1; ILKAP; SLC25A32; CLPTM1L; PTDSS2; HM13; ITFG1; SGPP1; WBSCR16; C1orf21; CSRNP2; MRPS26; ANKRD13C; CCDC130; PLA2G12A; CTNNBL1; APOL2; TRIM5; SNX27; C6orf62; ISCA1; TRIM56; SBF2; MED25; SHARPIN; ARPC5L; RAB1B; QTRT1; SLC25A28; HDHD3; NECAB3; MRPS15; SF3B5; INO80B; RAB33B; HUWE1; MRPL9; RILP; COG3; GUCD1; ZMIZ2; FAM103A1; SELO; RIOK1; GRWD1; L3MBTL2; LONP2; RBM4B; BBS2; GORASP1; MRPS5; MRPL32; FRMD8; ATAD3B; TAF3; RSPH3; TMEM120A; SNX25; MRPS24; RNF26; STK40; C10orf11; EIF2A; TM2D1; ITFG3; SRSF8; MRPL14; MRPL43; RBM48; MAGT1; HDHD2; TMEM222; SLC10A7; KBTBD7; ANKRD27; ENKD1; CEP192; PCBD2; ZNF394; ATRIP; WDR75; USP42; TOMM40L; UTP15; PHAX; SLC7A6OS; FAM175B; KAT8; RNASEH2C; RPF2; SON; ANKRD17; CHD6; PCNXL3; ZCCHC7; SETD3; SGK196; TMEM117; WDR24; ZNRF1; TRAF7; MAF1; MED10; SLC37A3; DCUN1D5; POLR3GL; C9orf64; CHCHD5; C9orf89; POLDIP3; YIPF4; NOA1; COQ5; NICN1; PRADC1; BTBD10; TMEM79; NTPCR; TMEM175; ZDHHC16; ING5; UTP23; LLPH; MIEN1; MNF1; PDCD2L; MRPL45; BRMS1L; VPS25; LSMD1; ACBD6; DNAJC14; LZIC; APOPT1; TMEM101; ELOF1; GFM2; COG5; HPS3; C5orf4; MKI67IP; BAZ1B; PINK1; HOOK3; MSANTD4; SYVN1; ZNF333; FAM120B; CC2D1B; ZNF527; PPIL3; MRPS6; MRPL41; MRPL38; MRPL36; C14orf142; JAGN1; ZC3H8; MAK16; GNPTG; USP38; HIATL1; SMEK1; GLYR1; DPY30; FAM126A; USP32; HINT2; MCEE; LOXL3; USP30; FUT10; PCGF1; MPV17L2; TUBA1C; MFSD9; TXNDC17; LMNB2; PHF5A; LRCH3; KLHL22; CCDC142; CBR4; ZC3H10; PARP10; ZBTB45; SYAP1; SPPL2A; ADO; GTDC2; FAM73B; ATAD1; TBRG1; NFATC2IP; CEP89; ZNF341; FAM136A; TMEM87B; CIRH1A; PPP1R15B; FIZ1; DIRC2; SPRYD3; TMEM209; C8orf76; C12orf52; ATG4C; MUM1; WDR73; LACTB; ABHD13; LTV1; SERAC1; TIGD5; PRPF38A; ALKBH6; LSM10; ATG4D; PPP1R16A; PYURF; UBL7; TMEM128; TMEM141; TMEM60; C9orf37; POLR2C; CSRNP1; HIAT1; SYNE1; SARNP; EAF1; ALG2; ZCCHC3; PNPT1; RRP36; ZCRB1; NEK9; RBM18; SURF4; PIGS; LMF2; PPP1R3F; PURB; DGCR6L; BTBD6; MRPS36; C22orf32; MICALL1; KIAA1731; ZNF622; IMP4; METTL18; PGAP3; C9orf123; CDK11B; TPGS1; MFN1; INTS4; TRIM41; TP53RK; N4BP2L1; MMAB; CCDC97; GADD45GIP1; ADCK2; ZNF830; RFT1; MGME1; VPS26B; NACC1; MBD6; ESCO1; SMYD4; ATG4A; WDFY2; DNTTIP1; RBM33; TMEM203; EGLN2; MRPL53; SNAP47; TADA1; THEM4; GLMN; ANKH; KLHDC3; NAA15; TSR2; UBE2J2; LOH12CR1; SMIM11; FAM207A; RPUSD1; ZNF354B; MYO18A; SLC36A1; SCAMP4; PIGU; SLC44A1; B3GALT6; MED30; TMEM41A; CDKN2AIPNL; SLC35A4; DYNLL2; UBE2F; SRXN1; B3GAT2; ROMO1; DTD1; FAM210B; OVCA2; SPSB3; SOCS4; PRRC1; ELMO2; LRPPRC; WIPF2; RSPRY1; ZNF526; ZNF721; SAT2; HELQ; MED22; RAD52; NUP35; SPTSSA; PYGO2; FAM122A; KLC4; KIAA2013; FAM105B; SAMD1; C19orf52; CEP95; PRMT10; TTC5; OXNAD1; MTG1; G6PC3; TMEM183A; MARS2; NOM1; MVB12A; GTF3C6; KTI12; FAM195A; SAAL1; CASC4; C12orf57; MFSD2; MALSU1; ACYP2; BATF2; NUS1; GLI4; CDAN1; CYHR1; TECR; HINT3; TAF8; HAS3; PPP1R14B; MPLKIP; NDNL2; RHOT2; SLC25A46; ALKBH8; WDR85; ZNF653; GINM1; LEO1; ANKRD54; MITD1; TAMM41; HIGD2A; MSI2; SPPL3; PPIL4; ALKBH3; FGD4; MTFMT; PPM1L; TSTD2; EHD4; ORMDL3; WDR36; PPTC7; RPIA; SLC39A3; ANGEL2; HN1L; MAPK1IP1L; L3HYPDH; TEX261; LRRC28; FOPNL; ZC3H18; FLCN; CYB5D1; TBC1D20; TMEM42; NACC2; FAM76B; ZNF18; ZNF480; ZNF420; ZNF558; ZNF570; BROX; LSM14B; PUS10; SEPT10; CCDC12; SPICE1; THAP6; ZMAT2; APOA1BP; MBNL2; FAM91A1; DENND5B; ZNF564; IMMP1L; ZFC3H1; LRRC45; TSNARE1; CCNY; UBLCP1; UPRT; FUK; ZUFSP; OARD1; NSMCE1; FAM200A; ZSCAN25; SFT2D1; MAP2K7; NAPRT1; CSNK1A1L; VTI1A; MRPL30; OMA1; FRA10AC1; UBALD1; MRPL10; CCDC127; NUDCD2; C6orf57; ZBTB49; SLC15A4; ATPAF2; KIFC2; ABTB2; ZNF511; MTPN; CRYZL1; ZNF23; ZSCAN21; ZNRF2; SGMS1; RPP25L; SVIP; RPUSD2; C12orf23; CHMP7; ZNF585B; ARRDC1; ORAI3; ZNF561; TADA2B; TRMT61A; SLC36A4; ARL14EP; C12orf45; TARSL2; SPATA2L; LSM12; ZNF491; ZNF440; C1orf131; KCTD18; METTL6; GRPEL2; ZNF786; NDUFAF6; TMEM68; HGSNAT; ARHGAP42; KBTBD3; CWF19L2; C12orf66; LYSMD4; ZSCAN29; ZNF785; TMEM199; ZNF417; C19orf25; B3GALNT2; ZNF362; MROH8; COMMD1; KANSL1L; XXYLT1; SCFD2; TRMT44; SRFBP1; SNRNP48; ZNF579; ZNF383; SDE2; RNF168; MIER3; TCEANC; ARID2; UBE2E2; NANP; DENND6A; RWDD4; CCDC111; HIPK1; SENP5; STT3A; PATL1; EFHA1; CPNE2; NT5DC1; C6orf89; HIBADH; BRAT1; RICTOR; YTHDF3; TMEM256; MFSD8; D2HGDH; TAB3; TMEM18; UHRF2; TANGO2; N4BP1; TCEANC2; EID2; NPHP3; ZNF461; LRRC57; CNEP1R1; PUSL1; TMEM161B; ZNF791; TAPT1; KIAA1919; LNX2; AGXT2L2; MED19; COG7; CRYBG3; CPNE8; PIGP; ZFP1; C2orf69; ZNF367; AAED1; KDELC2; TTL; CACUL1; ZFPM1; MLL3; MLX; C11orf31; PGBD3; TRIM35; HSCB; CBWD2; RC3H1; TNFSF12-TNFSF13; SUGP1; MMAA; MRPL54; PSENEN; RUNDC1; FAM149B1; MMGT1; DCUN1D3; CCDC117; ZNF584;

KCTD20; PRR14L; ANKRD52; DIP2B; INO80E; HEXDC; RTTN; ZNF776; SLC9A9; C3orf33; DCBLD1; NSMCE2; PDZD8; BLOC1S2; TTC9C; FAM126B; C3orf38; RABL3; COX18; SREK1IP1; KRTCAP2; NDUFAF2; PPP4R2; CCDC50; TMEM167A; NOP9; UBR1; ADCK5; N6AMT2; GPATCH11; ZNF575; EMC10; DDX51; UBR7; TXLNA; EXOC8; ZADH2; CRIPAK; C5orf51; CDK5RAP3; CHMP4B; ZNF800; GATC; INADL; NR2C2AP; MIDN; NUDT14; CYP20A1; P4HTM; PDE12; PPM1G; TUBB; GGT7; ERC1; FAM134C; SLC35B2; ZNF598; MRPL52; GMCL1; DRAM2; PIGW; ZNF616; ZBTB8OS; ZNF678; ZDHHC21; MTDH; ARL5B; AGPAT6; STT3B; GPR180; ZACN; MRPL55; GCC2; ZNF445; EXOSC8; MRPL21; AUP1; C17orf58; OGT; QSOX2; LYRM7; DNAJC24; BCDIN3D; GRASP; UBXN2A; CRTC2; METTL2A; TMTC3; DPY19L4; AASDH; TMED7; ZSCAN22; ZSCAN2; COQ6; USP12; ZNF227; ZNF428; MTERFD2; C9orf85; CMC1; ZNF595; NSUN6; TMED4; BRICD5; PDDC1; C15orf38; MRPS9; TPRG1L; TRNT1; TICAM1; HEATR3; ZNF326; CYP2U1; C9orf142; ARRDC4; HNRNPA3; DND1; ISCA2; SPTY2D1; RPS19BP1; PHLPP1; RNF126; C7orf55; TSC22D3; GNPNAT1; COX20; C1orf52; CCZ1B; GANC; ARSK; E2F6; LYSMD3; GANAB; APOOL; RSBN1L; C19orf54; RPL7L1; CCDC84; FAM174A; NHLRC2; ZNF710; HDDC3; ATP9B; ZNF773; MIA3; TMEM110; ACACA; FAM120AOS; NUP43; SS18L1; DHX57; NELFCD; NSUN4; NDUFAF3; CARM1; TMEM189-UBE2V1; CCDC137; NACA2; PHF17; FAHD2B; TMEM179B; CCDC23; FAM86A; SLC25A35; RP9; POLR1C; CHCHD1; RAPH1; TMEM81; RBM12B; MBLAC1; MRFAP1L1; COMMD6; C19orf70; CLYBL; MRAP; RNF216; GTF2H5; FAM199X; ERICH1; ZDHHC24; TSEN54; CYP4V2; C1orf174; BLOC1S3; METTL10; ZNF543; ZNF789; ZNF517; SFXN4; and any combinations thereof. In some embodiments, the reference gene(s) is/are analyzed by an additional qPCR reaction.

In some embodiments, the in-process control is a control for reverse transcriptase and/or PCR reaction performance. These in-process controls include, by way of non-limiting examples, a reference RNA (also referred to herein as ref.RNA), that is spiked in after RNA isolation and prior to reverse transcription. In some embodiments, the ref RNA is a control such as Qbeta. In some embodiments, the ref RNA is analyzed by an additional PCR reaction.

In some embodiments, the extracted nucleic acids, e.g., RNA and circulatingNA, are further analyzed based on detection of the T790M mutation, the L858R mutation, the one or more exon19 deletions and/or the one or more exon19 insertions.

The T790M mutation has been identified as a gatekeeper mutation. This so-called gatekeeper mutation is not only thought to appear through selective pressure during treatment, but it can in rare cases (<5%) also be found in TKI untreated tumors, potentially contributing to primary resistance to these drugs (See e.g., Gazdar et al., "Activating and resistance mutations of EGFR in non-small-cell lung cancer: role in clinical response to EGFR tyrosine kinase inhibitors." Oncogene, vol. 28 Suppl 1: S24-31 (2009), Suda et al., "EGFR T790M mutation: a double role in lung cancer cell survival?" J Thorac Oncol, vol. 4: 1-4 (2009); Mulloy et al., "Epidermal growth factor receptor mutants from human lung cancers exhibit enhanced catalytic activity and increased sensitivity to gefitinib." Cancer Res., vol. 67(5): 2325-30 (2007), and Vikis et al., "EGFR-T790M is a rare lung cancer susceptibility allele with enhanced kinase activity." Cancer Res., 67(10): 4665-70 (2007), the contents of which are hereby incorporated by reference in their entirety). The emergence of more sensitive molecular methods has also facilitated the detection of this mutation in tumors from treatment naïve patients, potentially contributing to primary resistance to TKIs as well. Finally, the presence of T790M in pre-treated patients was associated with a significant progression-free survival compared to pre-treated patients without detectable T790M (see e.g., Pao et al., "Acquired resistance of lung adenocarcinomas to gefitinib or erlotinib is associated with a second mutation in the EGFR kinase domain." PLoS Med., vol. 2(3): e73 (2005), Maheswaran et al., "Detection of mutations in EGFR in circulating lung-cancer cells." N Engl J Med, vol. 359(4): 366-77 (2008), and Isobe et al., "Clinical significance of BIM deletion polymorphism in non-small-cell lung cancer with epidermal growth factor receptor mutation." J Thorac Oncol, vol. 9(4): 483-87 (2014), the contents of which are hereby incorporated by reference in their entirety).

Patients that harbor other EGFR mutations (such as exon 21, L858R and exon 19 insertion and deletions) have shown better radiographic response rate in prospective trials, including randomized phase III trials [Fukuoka et al. 2011; "Biomarker analyses and final overall survival results from a phase III, randomized, open-label, first-line study of gefitinib versus carboplatin/paclitaxel in clinically selected patients with advanced non-small-cell lung cancer in Asia (IPASS).", Journal of Clinical Oncology, vol. 29(21):2866-74 (2011)]. For L858R and exon 19 insertion and deletions, significant treatment benefits were demonstrated for gefitinib and erlotinib, in Summary of Safety and Effectiveness Data (SSED) P160045 and P150044, available on the Internet at accessdata.fda.gov/cdrh_docs/pdf16/p1060045b.pdf and accessdata.fda.gov/cdrh_docs/pdf15/p150044b.pdf, respectively.

In some embodiments, additional analysis is performed using machine-learning based modeling, data mining methods, and/or statistical analysis. In some embodiments, the data is analyzed to derive a cutoff value in order to identify or predict disease outcome of the patient. In some embodiments, the data is analyzed to stratify the patient within a patient population. In some embodiments, the data is analyzed to identify or predict whether the patient is resistant to treatment with an EGFR therapy, such as, by way of non-limiting example, treatment with an EGFR inhibitor. In some embodiments, the data is to measure progression-free survival progress of the subject.

In some embodiments, the data is analyzed to select a treatment option for the subject when the T790M mutation, the L858R mutation, the one or more exon19 insertions and/or the one or more exon19 deletions is detected. In some embodiments, the treatment option is treatment with an EGFR inhibitor. In some embodiments, the EGFR inhibitor is a tyrosine kinase inhibitor or a combination of tyrosine kinase inhibitors or any other molecular drug including immunotherapy drugs. In some embodiments, the EGFR inhibitor is a first-generation tyrosine kinase inhibitor or a combination of first-generation tyrosine kinase inhibitors. In some embodiments, the EGFR inhibitor is a second-generation tyrosine kinase inhibitor or a combination of second-generation tyrosine kinase inhibitors. In some embodiments, the EGFR inhibitor is a third-generation tyrosine kinase inhibitor or a combination of third-generation tyrosine kinase inhibitors. In some embodiments, the EGFR inhibitor is a combination of a first-generation tyrosine kinase inhibitor, a second-generation tyrosine kinase inhibitor, and/or a third-generation tyrosine kinase inhibitor. In some embodiments, the EGFR inhibitor is erlotinib, gefitinib, another tyrosine kinase inhibitor, or combinations thereof. In some embodiments, the EGFR inhibitor is a next generation tyrosine kinase inhibitors (i.e. fourth-generation tyrosine kinase inhibitor) or another molecular drug that targets T790M or any mutation or genetic alteration within EGFR. In further embodiments, the above EGFR inhibitors are used in combination with immunotherapy drug(s) that boosts the patient's own immune response against tumor cells.

Various aspects and embodiments of the invention will now be described in detail. It will be appreciated that modification of the details may be made without departing from the scope of the invention. Further, unless otherwise required by context, singular terms shall include pluralities and plural terms shall include the singular.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representations as to the contents of these documents are based on the information available to the applicants and do not constitute any admission as to the correctness of the dates or contents of these documents.

DETAILED DESCRIPTION OF THE INVENTION

Figure 1A:
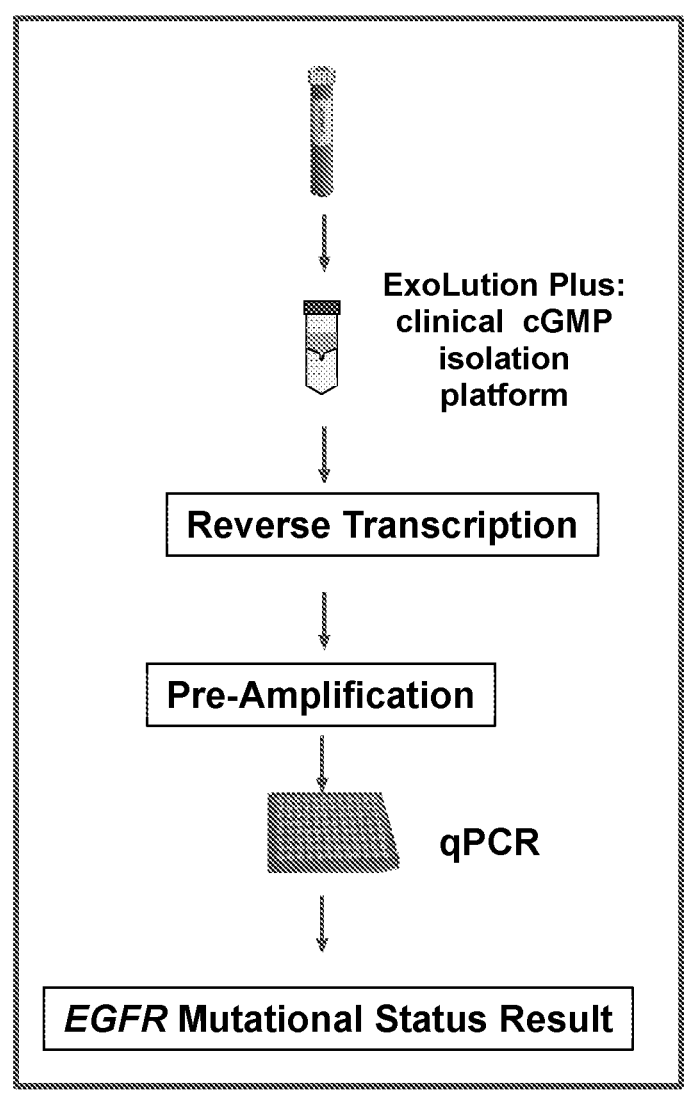
FIG. 1 is a schematic representation of the T790M detection assay workflow from sample extraction to mutation calling.

The present disclosure provides methods of detecting one or more biomarkers, such as an Epidermal Growth Factor Receptor (EGFR) mutation in a biological sample to aid in diagnosis, prognosis, monitoring, or therapy selection for a disease such as, for example, cancer. In some embodiments, the cancer is a lung cancer. In some embodiments, the cancer is non-small cell lung cancer (NSCLC).

The methods and kits provided herein are useful in detecting an EGFR resistance and/or sensitizing mutations in a biological sample. In some embodiments, the EGFR mutation is the T790M mutation on exon 20 of the EGFR gene. In some embodiments, the mutation is an activating mutation, including, but not limited to, one or more insertion mutations in exon 19 of the EGFR gene, one or more deletion mutations in exon 19 of the EGFR gene, the L858R mutation on exon 21 of the EGFR gene. The methods and kits provided herein co-isolate both extracellular NA and cell free NA from plasma, and the extracellular NA and cell free NA are reverse transcribed. At the reverse transcription step, an amplification control (DNA) and an RNA spike in control are added to ensure reverse transcription and subsequent amplifications occur. In the next step, a pre-amplification reaction is performed. In some embodiments, the pre-amplification reaction is a multiplex pre-amplification reaction. In some embodiments, the pre-amplification reaction is a multiplex pre-amplification reaction that includes a wild type blocker. In some embodiments, the multiplex pre-amplification reaction includes a wild type blocker for exon 19, exon 20, and/or exon 21 of EGFR, which favors amplification of mutant molecules from circulatingNA and cDNA. In some embodiments, the wild type blocker is a hydrophobic nucleic acid, a bridge nucleic acid, a peptide nucleic acid, any oligonucleotide with a 3' end terminator, any other modification that prevents efficient detection of the wild type molecule or combinations thereof. In some embodiments, the pre-amplification step is performed under conditions that favor pre-amplification of a mutant EGFR sequence, e.g., a mutant EGFR exon 19 sequence, a mutant EGFR exon 20 sequence, and/or a mutant EGFR exon 21 sequence, over a wild type sequence. In some embodiments, the pre-amplification reaction is a single-plex pre-amplification reaction. In some embodiments, the pre-amplification reaction and the reverse transcription are run in a single step. In the next step, the nucleic acids are analyzed using a sequencing-based detection technique such as NGS. In some embodiments, the sequencing-based detection technique comprises a PCR-based technique. In some embodiments, the sequencing-based detection technique also involves qPCR. In some embodiments, qPCR is based on an Amplification Refractory Mutation System (ARMS).

The methods and kits provided herein can be used to guide treatment of NSCLC patients with this mutation, which as a result will be resistant to first generation of Tyrosine Kinase Inhibitors (TKI).

The methods and kits provided herein have several advantages over current lung cancer diagnostics. Current methods of detecting T790M in patient samples are described, for example, in Thress et al. ("EGFR mutation detection in ctDNA from NSCLC patient plasma: A cross-platform comparison of leading technologies to support the clinical development of AZD9291." Lung Cancer, vol. 90(3): 509-15 (2015)) and in Karlovich et al. ("Assessment of EGFR Mutation Status in Matched Plasma and Tumor Tissue of NSCLC Patients from a Phase I Study of Rociletinib (CO-1686)." Clin. Cancer Res., vol. 22(10): 2386-95 (2016)). A sample of the sensitivity and specificity of these methods of detecting T790M in NSCLC patients is shown in the table below:

| | Method | Sensitivity | Specificity | Positives Patient no. | Negatives Patient no. | Total no. patients |
|---|---|---|---|---|---|---|
| Thress et al. | Cobas® | 41% | 100% | 7/17 | 6/6 | 23 |
| | Therascreen | 29% | 100% | 5/17 | 6/6 | |
| | ddPCR | 71% | 83% | 12/17 | 5/6 | |
| | Beaming | 71% | 67% | 12/17 | 4/6 | |
| | Cobas® | 73% | 67% | 30/41 | 16/24 | 65 |
| | Beaming | 81% | 58% | 33/41 | 14/24 | |
| Karlovich et al. | Cobas® | 64% (PPA) | 98% (NPA) | 21/33 | 61/62 | 95 |
| | Beaming | 73% (PPA) | 50% (NPA) | 33/45 | 9/18 | 63 |

The table below shows the sensitivity and specificity for all three targets from the AURA3 clinical trial (NCT02151981) (presented by J. Laskin in the International Association for Study of Lung Cancer, "Detection of EGFR mutations from plasma ctDNA in the osimertinib Phase III trial (AURA3): comparison of three plasma assays", 2017, available at library.iaslc.org/search-speaker?search_speaker=51233)

Concordance data from a subset of osimertinib-dosed patients with a valid cubas tissue T790M-positive result and matched plasma samples.

| Test | EGFR T790M | | EGFR Ex19ol | | EGFR L858R | |
|---|---|---|---|---|---|---|
| | PPA | NPA* | PPA | NPA | PPA | NPA |
| AS-PCR (ex226) | 51% (115/226) | NA | 85% (132/158) | 99% (70/71) | 59% (40/68) | 100% (158/158) |
| ddPCR (ex208) | 57% (118/208) | NA | 72% (102/142) | 100% (66/66) | 69% (44/64) | 99% (141/143) |
| NGS (ex227) | 66% (148/227) | NA | 81% (126/158) | 99% (70/71) | 62% (42/68) | 98% (156/159) |

*Specificity for T790M was not evaluated as only T790M positive tissues were available.
NA: not applicable;
NPA: negative percent agreement (specificity);
PPA: positive percent agreement (sensitivity).

Current lung cancer diagnosis is done by pathologists, and sampling tumor tissue has significant inherent limitations, such as, for example, tumor tissue is a single snapshot in time, is subject to selection bias resulting from tumor heterogeneity, and can be difficult to obtain. In some cases, a sufficient sample of tumor tissue is not available for some patients and/or obtaining a tissue sample can cause complications such as pneumothorax. However, so far, the reference non-standard method for patient stratification has been tissue biopsies.

The kits and methods provided herein leverage the ability to look at the entire disease process and the tumor environment, as there are several processes that are leading to the release of nucleic acids (extracellular NA) into any given biofluid. Amongst these processes are, for example, apoptosis and necrosis. Apoptotic or necrotic cells may release cell free nucleic acids by different mechanisms (i.e. apoptotic vesicles or as circulating nucleosomes). Additionally, EVs are actively released by living cells directly from the plasma membrane or via the multivesicular body pathway carrying nucleic acids into circulation (exoNA). In contrast to the current methods of detecting T790M, L858R, one or more exon19 insertions and/or one or more exon19 deletions in a patient sample, the methods and kits provided herein are able to analyze all of the processes that are simultaneously happening inside the tumor.

These methods and kits are novel: While the detection of T790M, L858R, and one or more exon19 insertions and/or one or more exon19 deletions in DNA from tissue biopsies is routinely performed already, detecting T790M, L858R, and one or more exon19 insertions and/or one or more exon19 deletions in circulatingNA in addition to the exosomal NA fraction is entirely new. These methods and kits are also not obvious over current methods as it has only recently been understood, that biofluids contain tumor-derived NA that can be used for diagnostic assays.

The working examples provided herein describe a complete workflow for the detection of T790M, L858R, one or more exon19 insertions and/or one or more exon19 deletions in EGFR from sample extraction to mutation calling using cell free NA and extracellular NA as sample input material. While the working examples provide one exemplary embodiment, it is understood that the skilled artisan can modify the methods used there to produce general methods for detection of T790M, L858R, and one or more exon19 insertions and/or one or more exon19 deletions, in EGFR. Generally, the presence of T790M, L858R, one or more exon19 insertions and/or one or more exon19 deletions is detected as follows:

1) T790M, L858R, and/or exon 19 insertions and/or deletions, present in the extracellular NA and circulatingNA, are co-isolated from plasma or other biofluids by using any suitable separation means, including, by way of non-limiting example, an affinity binding column or beads, an ion exchange binding column or beads, or centrifugation, ultracentrifugation, or Polyethylene Glycol (PEG) precipitation.

2) Isolated nucleic acids get reverse transcribed, and at this step, a known quantity of a control nucleic acid, is added into the reaction as a control of inhibition. Any exogenous nucleic acid or synthetic nucleic acid can be used in the methods provided herein. Suitable controls include, by way of non-limiting example, one or more nucleic acids from the Q-beta bacteriophage, virus particles, any other exogenous nucleic acid sequence(s), and any other non-human nucleic acid sequence that acts as an external spike-in. The spike-in can be whole particles (e.g., Qbeta or other viral particles, liposome or protein complexes) or only the nucleic acid thereof. Whole particles are better suited when the spike-in occurs into the biofluid prior to nucleic acid isolation and "free" nucleic acid spike-ins that are not protected by a lipid complex, protein complex or other are better suited to be spiked into the sample after nucleic acid purification.

3) At this stage, the reverse transcription (RT) reaction can be pre-amplified. The pre-amplification step occurs in the presence of a wild type clamp or blocker, producing a mutant biased population of molecules. Suitable wild-type clamps for use in this step include, by way of non-limiting example, one or more hydrophobic nucleic acid(s), one or more bridge nucleic acids, one or more peptide nucleic acids, any oligonucleotide with a 3' end terminator (e.g., inverted base, C3-spacer, Phosphate, etc.), or combinations thereof. In some embodiments, the pre-amplification step occurs under any PCR conditions that favor amplification of the mutant sequence over the wild type sequence. In some embodiments, the pre-amplification step is not required and the method proceeds direct to the qPCR step below.

4) The qPCR step occurs in a multiplex reaction (endogenous control, T790M and/or L858R and/or exon19 insertions and/or deletions and control of inhibition). The T790M and/or L858R and/or exon19 insertions and/or deletions can be detected using any suitable detection methods, including those that favor the amplification of the mutant molecule over the wild type molecule. In some embodiments, the T790M, L858R, and exon19 insertions and/or deletions is detected using an ARMS approach. The 3' base of the reverse primer is fully matched to the mutant sequence (T790M and/or L858R and/or exon19 insertions and/or deletions) and has a mismatch with the wild type template. The base modification near the 3' end includes a modified base such as 2-aminopurine, 8-amino-2'-deoxyadenosine, trimetroxystilbene, C-5 propynyl-deoxycytidine, C-5 propynyl-deoxyuridine, 2-amino-2'-deoxyadenosine-5'-triphosphate, 2,6-diaminopurine (2-amino-dA), inverted dT, inverted dideoxy-T, hydroxymethyl dC, iso-dC, 5-methyl dC, aminoethyl-phenoxazine-deoxycytidine, and locked nucleic acids (LNA's), and the inclusion of at least one mismatched base at one of the bases to increase the nucleic acid interaction at the 3' end of the mutant specific primer. Also contemplated is an additional mismatch at one of the bases of the mutant specific primer. In some embodiments, at least one mismatched base is the fourth to the last, antepenultimate, penultimate or the last base of the mutant specific primer.

5) To discriminate or quantify the disease outcome of patients, state-of-the-art machine learning and data-mining techniques are used to train a model on several features from the qPCR step, such as, but not limited to, CT values, delta CT values, raw Rn values as well as ROX normalized dRn values.

6) Various boundary conditions on internal controls are determined to establish filters for quality control before sample classification to exclude samples that show spurious behavior.

In some embodiments, the presence T790M, L858R, and/or exon 19 insertions and/or deletions is detected as follows:

1) T790M, L858R, and/or exon 19 insertions and/or deletions, present in the extracellular NA and circulatingNA gets co-isolated from plasma or other biofluids by using an affinity binding column.

2) Isolated nucleic acids get reverse transcribed using a first strand cDNA synthesis kit. At this step, 4000 copies of QBeta (synthetic RNA, exogenous spike) is added into the reaction as a control of inhibition.

3) The RT reaction gets pre-amplified. The pre-amplification step occurs in the presence of a wild type blocker (hydrophobic nucleic acid), producing a mutant biased population of molecules.

4) qPCR step occurs in a multiplex reaction (endogenous control, T790M, L858R, and/or exon19 insertions and/or or deletions and control of inhibition). T790M, L858R, and/or exon19 insertions and/or deletions gets detected using an ARMS approach. The 3' base of the reverse primer is fully matched to the mutant sequence (T790M, L858R, and/or exon19 insertions and/or deletions) and has a mismatch with the wild type template. The base modification near the 3' end includes a modified base such as 2-aminopurine, 8-amino-2'-deoxyadenosine, trimetroxystilbene, C-5 propynyl-deoxycytidine, C-5 propynyl-deoxyuridine, 2-amino-2'-deoxyadenosine-5'-triphosphate, 2,6-diaminopurine (2-amino-dA), inverted dT, inverted dideoxy-T, hydroxymethyl dC, iso-dC, 5-methyl dC, aminoethyl-phenoxazine-deoxycytidine, and locked nucleic acids (LNA's), and the inclusion of at least one mismatched base at one of the bases to increase the nucleic acid interaction at the 3' end of the mutant specific primer. Also contemplated is an additional mismatch at one of the bases of the mutant specific primer. In some embodiments, at least one mismatched base is the fourth to the last, antepenultimate, penultimate or the last base of the mutant specific primer.

5) To discriminate or quantify the disease outcome of patients, state-of-the-art machine learning and data-mining techniques are used to train a model on several features from the qPCR step such as but not limited to CT values, delta CT values, raw Rn values as well as normalized dRn values against any passive reference (or no passive reference).

6) We determine various boundary conditions on internal controls to establish filters for quality control before sample classification to exclude samples that show spurious behavior.

The methods and kits were designed to identify and detect the T790M mutation, which is a 2369C to T mutation found in exon 20 of the EGFR gene; the L858R mutation, which is a 2573T to G mutation found in exon 21 of the EGFR gene; and one or more exon19 insertions and/or deletions of the EGFR gene. The methods and kits provided herein were designed to detect short amplicons (e.g., <200 base pairs), as circulating free NA is highly fragmented. The methods and kits provided herein include a control assay (wild type assay) to define the amount of amplifiable EGFR. The methods and kits provided herein use of a control of inhibition to assess the presence/absence of enzymatic inhibitors in a sample. The methods and kits provided herein also include the use of a wild type specific blocker to further prevent wild type amplification.

The methods and kits include the use of a modified nucleotide in the primer. The base modification near the 3' end includes a modified base such as 2-aminopurine, 8-amino-2'-deoxyadenosine, trimetroxystilbene, C-5 propynyl-deoxycytidine, C-5 propynyl-deoxyuridine, 2-amino-2'- deoxyadenosine-5'-triphosphate, 2,6-diaminopurine (2-amino-dA), inverted dT, inverted dideoxy-T, hydroxymethyl dC, iso-dC, 5-methyl dC, aminoethyl-phenoxazine-deoxycytidine, and locked nucleic acids (LNA's), and the inclusion of at least one mismatched base at one of the bases to increase the nucleic acid interaction at the 3' end of the mutant specific primer, to increase the Tm. Incorporation of duplex-stabilizing base modifications positively affects PCR, thereby allowing it to be conducted at higher temperatures, a range in which Taq polymerase is known to exhibit maximum activity.

It is understood that while specific primers and probe sequences are provided herein, the methods and kits of the disclosure can also use primers and/or probe sequences that comprise the sequences shown in Table 1, or primers and/or probe sequences that are modified versions of the sequences shown in Table 1. Modified versions of these primers and/or probe sequences can include, by way of non-limiting example, adding one or more nucleotides to the 5' end, adding one or more nucleotides to the 3' end, adding one or more nucleotides to both the 5' end and the 3' end, adding tails, shortening the sequences, lengthening the sequences, moving the sequences several bases up or downstream, or any combination thereof.

It is understood that while specific sequences for the positive control and the control of inhibition are provided herein, the methods and kits of the disclosure can also use control sequences that comprise these sequences, or control sequences that are modified versions of these sequences. Modified versions of these control sequences can include, by way of non-limiting example, adding one or more nucleotides to the 5' end, adding one or more nucleotides to the 3' end, adding one or more nucleotides to both the 5' end and the 3' end, adding tails, shortening the sequences, lengthening the sequences, moving the sequences a several bases up or downstream, or any combination thereof.

Furthermore, it is understood that the positive control sequences and control of inhibition sequence provided herein are exemplary. The methods and kits of the disclosure can use any suitable synthetic gene sequence that acts as a positive control. For example, in some embodiments, the positive control sequence can be the EGFR gene, a fragment of the EGFR gene, or a sequence that is derived from the EGFR gene, including, by way of non-limiting example, a modified version of the EGFR gene. Likewise, the methods and kits of the disclosure can use any suitable gene sequence that acts as a control of inhibition. For example, in some embodiments, the control of inhibition sequence can be a Q-beta RNA sequence, a fragment of a Q-beta RNA sequence, or a sequence that is derived from a Q-beta RNA sequence, including, by way of non-limiting example, a modified version of a Q-beta RNA sequence, as well as any other non-human sequence that can be used to spike in any given biofluids (i.e. any viral/bacterial sequence). Modified versions of any of these control sequences can include, by way of non-limiting example, adding one or more nucleotides to the 5' end, adding one or more nucleotides to the 3' end, adding one or more nucleotides to both the 5' end and the 3' end, adding tails, shortening the sequences, lengthening the sequences, moving the sequences several bases up or downstream, or any combination thereof.

The methods and kits described herein isolate EVs by capturing the extracellular vesicles to a surface and subsequently lysing the microvesicles to release the nucleic acids, particularly RNA, contained therein. EVs may be shed by eukaryotic cells, or budded off of the plasma membrane, to the exterior of the cell. These membrane vesicles are heterogeneous in size with diameters ranging from about 10 nm to about 5000 nm. These microvesicles include microvesicles, microvesicle-like particles, prostasomes, dexosomes, texosomes, ectosomes, oncosomes, apoptotic bodies, retrovirus-like particles, and human endogenous retrovirus (HERV) particles and any other terms that refer to such extracellular structures. Small microvesicles (approximately 10 to 5000 nm, and more often 30 to 200 nm in diameter) that are released by exocytosis of vesicles are referred to in the art as "microvesicles."

Microvesicles are a rich source of high quality nucleic acids, excreted by all cells and present in all human biofluids. The RNA in microvesicles provides a snapshot of the transcriptome of primary tumors, metastases and the surrounding microenvironment in real-time. Thus, accurate assessment of the RNA profile of microvesicles by assays provides companion diagnostics and real-time monitoring of disease. This development has been stalled by the current standard of isolating exosomes which is slow, tedious, variable and not suited for a diagnostic environment.

The isolation and extraction methods and/or kits provided herein use a spin-column based purification process using an affinity membrane that binds microvesicles. The isolation and extraction methods are further described in PCT Publication Nos. WO 2016/007755 and WO 2014/107571, the contents of each of which are described herein in their entirety. The methods and kits of the disclosure allow for the capability to run large numbers of clinical samples in parallel, using volumes from 0.2 up to 8 mL on a single column. The isolated RNA is highly pure, protected by a vesicle membrane until lysis, and intact vesicles can be eluted from the membrane. The isolation and extraction procedures are able to extract all mRNA from any given plasma input, and are equal or better in mRNA/miRNA yield when compared to ultracentrifugation or direct lysis. In contrast, the methods and/or kits provided herein enrich for the microvesicle bound fraction of miRNAs, and they are easily scalable as well as amenable to automation to large amounts of input material. This ability to scale up enables research on interesting, low abundant transcripts. In comparison with other commercially available products on the market, the methods and kits of the disclosure provide unique capabilities that are demonstrated by the examples provided herein.

The isolation of microvesicles from a biological sample prior to extraction of nucleic acids is advantageous for the following reasons: 1) extracting nucleic acids from microvesicles provides the opportunity to selectively analyze disease or tumor-specific nucleic acids obtained by isolating disease or tumor-specific microvesicles apart from other microvesicles within the fluid sample; 2) nucleic acid-containing microvesicles produce significantly higher yields of nucleic acid species with higher integrity as compared to the yield/integrity obtained by extracting nucleic acids directly from the fluid sample without first isolating microvesicles; 3) scalability, e.g., to detect nucleic acids expressed at low levels, the sensitivity can be increased by concentrating microvesicles from a larger volume of sample using the methods described herein; 4) more pure or higher quality/integrity of extracted nucleic acids in that proteins, lipids, cell debris, cells and other potential contaminants and PCR inhibitors that are naturally found within biological samples are excluded before the nucleic acid extraction step; 5) more choices in nucleic acid extraction methods can be utilized as isolated microvesicle fractions can be of a smaller volume than that of the starting sample volume, making it possible to extract nucleic acids from these fractions or pellets using small volume column filters; and 6) isolation of microvesicles can be amenable to automation, which is advantageous because it prevents from human error and provides the capability or scaling up Several methods of isolating microvesicles from a biological sample have been described in the art. For example, a method of differential centrifugation is described in a paper by Raposo et al. (Raposo et al., 1996), a paper by Skog et al. (Skog et al., 2008) and a paper by Nilsson et al. (Nilsson et al., 2009). Methods of ion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel Taylor (Taylor and Gercel-Taylor, 2008). A method of nanomembrane ultrafiltration concentration is described in a paper by Cheruvanky et al. (Cheruvanky et al., 2007). A method of Percoll gradient isolation is described in a publication by Miranda et al. (Miranda et al., 2010). Further, microvesicles may be identified and isolated from bodily fluid of a subject by a microfluidic device (Chen et al., 2010). In research and development, as well as commercial applications of nucleic acid biomarkers, it is desirable to extract high quality nucleic acids from biological samples in a consistent, reliable, and practical manner.

Nucleic Acid Extraction

The methods disclosed herein use a highly enriched microvesicle fraction for extraction of high quality nucleic acids from said microvesicles. The nucleic acid extractions obtained by the methods described herein may be useful for various applications in which high quality nucleic acid extractions are required or preferred, such as for use in the diagnosis, prognosis, or monitoring of diseases as well as other application for any medical condition, such as for example, cancer. The methods and kits provided herein are useful in detecting a T790M EGFR mutation, a L858R EGFR mutation, one or more exon19 insertions and/or one or more exon19 deletions of EGFR for the diagnosis of non-small cell lung cancer (NSCLC).

The quality or purity of the isolated microvesicles can directly affect the quality of the extracted microvesicle nucleic acids, which then directly affects the efficiency and sensitivity of biomarker assays for disease diagnosis, prognosis, and/or monitoring. Given the importance of accurate and sensitive diagnostic tests in the clinical field, methods for isolating highly enriched microvesicle fractions from biological samples are needed. To address this need, the present invention provides methods for isolating microvesicles from biological sample for the extraction of high quality nucleic acids from a biological sample. As shown herein, highly enriched microvesicle fractions are isolated from biological samples by methods described herein, and wherein high quality nucleic acids subsequently extracted from the highly enriched microvesicle fractions. These high quality extracted nucleic acids are useful for measuring or assessing the presence or absence of biomarkers for aiding in the diagnosis, prognosis, and/or monitoring of diseases or other medical conditions.

As used herein, the term "biological sample" refers to a sample that contains biological materials such as nucleic acids and protein. In some embodiments, the biological sample may suitably comprise a bodily fluid from a subject. The bodily fluids can be fluids isolated from anywhere in the body of the subject, for example, a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, intra-organ system fluid, ascitic fluid, tumor cyst fluid, amniotic fluid and cell culture supernatant, and combinations thereof. In some embodiments, the body fluid is plasma. Suitably a sample volume of about 0.1 mL to about 100 mL fluid may be used. The volume of fluid may depend on a few factors, e.g., the type of fluid used. For example, the volume of serum samples may be about 0.1 mL to about 8 mL, for example, about 0.2 mL to 8 mL. The volume of plasma samples may be about 0.1 mL to about 4 mL, for example, 0.5 mL to 4 mL. The volume of urine samples may be about 10 mL to about 30 mL, for example, about 20 ml. Biological samples can also include fecal or cecal samples, or supernatants isolated therefrom.

The term "subject" is intended to include all eukaryotic organisms shown to or expected to have nucleic acid-containing particles. In particular embodiments, the subject is a mammal, a human or nonhuman primate, a dog, a cat, a horse, a cow, other farm animals, or a rodent (e.g. mice, rats, guinea pig. etc.). A human subject may be a normal human being without observable abnormalities, e.g., a disease. A human subject may be a human being with observable abnormalities, e.g., a disease. The observable abnormalities may be observed by the human being himself, or by a medical professional. The term "subject," "patient," and "individual" are used interchangeably herein.

As used herein, the term "nucleic acids" refer to DNA and RNA (including all their variations, such as microRNA, longRNA, etc). The nucleic acids can be single stranded or double stranded. In some instances, the nucleic acid is DNA. In some instances, the nucleic acid is RNA. RNA includes, but is not limited to, messenger RNA, transfer RNA, ribosomal RNA, non-coding RNAs, microRNAs, and HERV elements.

In one aspect, useful primers and probes comprises a nucleotide sequence greater than 60%, 65%, 70%, 75%. 80%, 85%, 90%, 91%, 92%, 93%, 94%, 95%, 96%, 97%, 98%, or 99% identity to the primer or probe provided in Table 1. Modifications of such primers and probes are also contemplated and can be prepared according to standard techniques.

The term "% identity," in the context of two or more nucleotide or amino acid sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For example, % identity is relative to the entire length of the coding regions of the sequences being compared.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Percent identity can be determined using search algorithms such as BLAST and PSI-BLAST (Altschul et al., 1990, J Mol Biol 215:3, 403-410; Altschul et al., 1997, Nucleic Acids Res 25:17, 3389-402).

In some embodiments, a high quality nucleic acid extraction is an extraction in which one is able to detect 18S and 28S rRNA. In some embodiments, the quantification of 18S and 28S rRNAs extracted can be used determine the quality of the nucleic acid extraction. In some embodiments, the quantification of 18S and 28S rRNA is in a ratio of approximately 1:1 to approximately 1:2; for example, approximately 1:2. Ideally, high quality nucleic acid extractions obtained by the methods described herein will also have an RNA integrity number of greater than or equal to 5 for a low protein biological sample (e.g., urine), or greater than or equal to 3 for a high protein biological sample (e.g., serum), and a nucleic acid yield of greater than or equal to 50 pg/ml from a 20 ml low protein biological sample or a 1 ml high protein biological sample.

High quality RNA extractions are desirable because RNA degradation can adversely affect downstream assessment of the extracted RNA, such as in gene expression and mRNA analysis, as well as in analysis of non-coding RNA such as small RNA and microRNA. The new methods described herein enable one to extract high quality nucleic acids from microvesicles isolated from a biological sample so that an accurate analysis of nucleic acids within the microvesicles can be performed.

Following the isolation of microvesicles from a biological sample, nucleic acid may be extracted from the isolated or enriched microvesicle fraction. To achieve this, in some embodiments, the microvesicles may first be lysed. The lysis of microvesicles and extraction of nucleic acids may be achieved with various methods known in the art, including those described in in PCT Publication Nos. WO 2016/007755 and WO 2014/107571, the contents of each of which are described herein in their entirety. Such methods may also utilize a nucleic acid-binding column to capture the nucleic acids contained within the microvesicles. Once bound, the nucleic acids can then be eluted using a buffer or solution suitable to disrupt the interaction between the nucleic acids and the binding column, thereby successfully eluting the nucleic acids.

In some embodiments, the nucleic acid extraction methods also include the step of removing or mitigating adverse factors that prevent high quality nucleic acid extraction from a biological sample. Such adverse factors are heterogeneous in that different biological samples may contain various species of adverse factors. In some biological samples, factors such as excessive DNA may affect the quality of nucleic acid extractions from such samples. In other samples, factors such as excessive endogenous RNase may affect the quality of nucleic acid extractions from such samples. Many agents and methods may be used to remove these adverse factors. These methods and agents are referred to collectively herein as an "extraction enhancement operations." In some instances, the extraction enhancement operation may involve the addition of nucleic acid extraction enhancement agents to the biological sample. To remove adverse factors such as endogenous RNases, such extraction enhancement agents as defined herein may include, but are not limited to, an RNase inhibitor such as Superase-In (commercially available from Ambion Inc.) or RNaseINplus (commercially available from Promega Corp.), or other agents that function in a similar fashion; a protease (which may function as an RNase inhibitor); DNase; a reducing agent; a decoy substrate such as a synthetic RNA and/or carrier RNA; a soluble receptor that can bind RNase; a small interfering RNA (siRNA); an RNA binding molecule, such as an anti-RNA antibody, a basic protein or a chaperone protein; an RNase denaturing substance, such as a high osmolarity solution, a detergent, or a combination thereof.

For example, the extraction enhancement operation may include the addition of an RNase inhibitor to the biological sample, and/or to the isolated microvesicle fraction, prior to extracting nucleic acid; for example, in some embodiments, the RNase inhibitor has a concentration of greater than 0.027 AU (1×) for a sample equal to or more than 1 μl in volume; alternatively, greater than or equal to 0. 1 35 AU (5×) for a sample equal to or more than 1 μl; alternatively, greater than or equal to 0.27 AU (10×) for a sample equal to or more than 1 μl; alternatively, greater than or equal to 0.675 AU (25×) for a sample equal to or more than 1 μl; and alternatively, greater than or equal to 1.35 AU (50×) for a sample equal to or more than 1 μl; wherein the 1× concentration refers to an enzymatic condition wherein 0.027 AU or more RNase inhibitor is used to treat microvesicles isolated from 1 μl or more bodily fluid, the 5× concentration refers to an enzymatic condition wherein 0.135 AU or more RNase inhibitor is used to treat microvesicles isolated from 1 μl or more bodily fluid, the 10× protease concentration refers lo an enzymatic condition wherein 0.27 AU or more RNase inhibitor is used to treat particles isolated from 1 μl or more bodily fluid, the 25× concentration refers to an enzymatic condition wherein 0.675 AU or more RNase inhibitor is used to treat microvesicles isolated from 1 μl or more bodily fluid, and the 50× protease concentration refers to an enzymatic condition wherein 1.35 AU or more RNase inhibitor is used to treat particles isolated from 1 μl or more bodily fluid. Preferably, the RNase inhibitor is a protease, in which case, 1 AU is the protease activity that releases folin-positive amino acids and peptides corresponding to 1 μmol tyrosine per minute.

These enhancement agents may exert their functions in various ways, e.g., through inhibiting RNase activity (e.g., RNase inhibitors), through a ubiquitous degradation of proteins (e.g., proteases), or through a chaperone protein (e.g., a RNA-binding protein) that binds and protects RNAs. In all instances, such extraction enhancement agents remove or at least mitigate some or all of the adverse factors in the biological sample or associated with the isolated particles that would otherwise prevent or interfere with the high quality extraction of nucleic acids from the isolated particles.

Detection of Nucleic Acid Biomarkers

The analysis of nucleic acids present in the isolated particles is quantitative and/or qualitative. For quantitative analysis, the amounts (expression levels), either relative or absolute, of specific nucleic acids of interest within the isolated particles are measured with methods known in the art (described below). For qualitative analysis, the species of specific nucleic acids of interest within the isolated microvesicles, whether wild type or variants, are identified with methods known in the art.

The present invention also includes various uses of the new methods of isolating microvesicles from a biological sample for high quality nucleic acid extraction from a for (i) aiding in the diagnosis of a subject, (ii) monitoring the progress or reoccurrence of a disease or other medical condition in a subject, or (iii) aiding in the evaluation of treatment efficacy for a subject undergoing or contemplating treatment for a disease or other medical condition; wherein the presence or absence of one or more biomarkers in the nucleic acid extraction obtained from the method is determined, and the one or more biomarkers are associated with the diagnosis, progress or reoccurrence, or predicting treatment efficacy, respectively, of a disease or other medical condition.

To this end, the present invention further embodies the derivation of clinically meaningful cutoff threshold(s) for the above-stated purposes by use of a method to discriminate between positive and negative samples. The cutoff value(s) is based on the absolute value of the delta between Exon20 CT and Exon7 CT. Intensity thresholds to estimate CT values for Exon20, Exon7 and QBeta have been optimized using an internal grid-search where the best of a family of models is selected by a grid of parameters. Delta CT cutoff to discriminate between positive and negative samples has been learned with the optimal intensity thresholds and has been selected based on Youden's J statistics.

In some embodiments, it may be beneficial or otherwise desirable to amplify the nucleic acid of the microvesicle prior to analyzing it. Methods of nucleic acid amplification are commonly used and generally known in the art, many examples of which are described herein. If desired, the amplification can be performed such that it is quantitative. Quantitative amplification will allow quantitative determination of relative amounts of the various nucleic acids, to generate a genetic or expression profile.

In some embodiments, the extracted nucleic acid comprises RNA. In this instance, the RNA is reverse-transcribed into complementary DNA (cDNA) before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. Another example of the method comprises two separate steps: a first of reverse transcription to convert RNA into cDNA and a second step of quantifying the amount of cDNA using quantitative PCR. As demonstrated in the examples that follow, the RNAs extracted from nucleic acid-containing particles using the methods disclosed herein include many species of transcripts including, but not limited to, ribosomal 18S and 28S rRNA, microRNAs, transfer RNAs, transcripts that are associated with diseases or medical conditions, and biomarkers that are important for diagnosis, prognosis and monitoring of medical conditions. For example, quantitative PCR (qPCR) analysis determines a Ct (cycle threshold) value for each reaction. In qPCR, a positive reaction is detected by, for example, accumulation of a fluorescence signal. The Ct value is defined as the number of qPCR cycles required for the fluorescent signal to cross the threshold (i.e., exceeds background level). Ct levels are inversely proportional to the amount of target nucleic acid, or control nucleic acid, in the sample (i.e., the lower the Ct level, the greater the amount of control nucleic acid in the sample). For the purpose of describing the present invention, the meaning of Ct also includes what is also described as "Cp" for "crossing point" for the skilled in the art. Cp refers to the point at which the amplification curve crosses the vertical threshold line/noise band), therefore both Ct and Cp can be used interchangeably. The methods of deriving Ct or Cp include: 1) the conventional method using the cycle value at which the (baseline-corrected) amplification curve crosses some arbitrary threshold value; 2) the second derivative maximum (SDM) method, where there's no need to define an arbitrary threshold value; and 3) ""fit points" method through a linear regression fit through the points of the log-linear phase of the amplification curve. In another embodiment, the copy number of the control nucleic acid can be measured using any of a variety of art-recognized techniques, including, but not limited to, qPCR or any other PCR or PCR-free methods. Copy number of the control nucleic acid can be determined using methods known in the art, such as by generating and utilizing a calibration, or standard curve.

In some embodiments, one or more biomarkers can be one or a collection of genetic aberrations, which is used herein to refer to the nucleic acid amounts as well as nucleic acid variants within the nucleic acid-containing particles. Specifically, genetic aberrations include, without limitation, transcript variants, over-expression of a gene (e.g., an oncogene) or a panel of genes, under-expression of a gene (e.g., a tumor suppressor gene such as p53 or RB) or a panel of genes, alternative production of splice variants of a gene or a panel of genes, gene copy number variants (CNV) (e.g., DNA double minutes) (Hahn, 1993), nucleic acid modifications (e.g., methylation, acetylation and phosphorylations), single nucleotide polymorphisms (SNPs), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splice variants and/or changes of gene expression level, or combinations of any of the foregoing.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., 1990), transcriptional amplification system and its variants (Kwoh et al., 1989), Qb Replicase and its variants (Miele et al., 1983), cold-PCR (Li et al., 2008), BEAMing (Li et al., 2006) or any other nucleic acid amplification methods, followed by the detection of the amplified molecules using techniques well known to those of skill in the art. Especially useful are those detection schemes designed for the detection of nucleic acid molecules if such molecules are present in very low numbers. The foregoing references are incorporated herein for their teachings of these methods. In other embodiment, the step of nucleic acid amplification is not performed. Instead, the extract nucleic acids are analyzed directly (e.g., through next-generation sequencing).

The determination of such genetic aberrations can be performed by a variety of techniques known to the skilled practitioner. For example, expression levels of nucleic acids, alternative splicing variants, chromosome rearrangement and gene copy numbers can be determined by microarray analysis (see, e.g., U.S. Pat. Nos. 6,913,879, 7,364,848, 7,378,245, 6,893,837 and 6,004,755) and quantitative PCR. Particularly, copy number changes may be detected with the Illumina Infinium II whole genome genotyping assay or Agilent Human Genome CGH Microarray (Steemers et al., 2006). Nucleic acid modifications can be assayed by methods described in, e.g., U.S. Pat. No. 7,186,512 and patent publication WO2003/023065. Particularly, methylation profiles may be determined by Illumina DNA Methylation OMA003 Cancer Panel. SNPs and mutations can be detected by hybridization with allele-specific probes, enzymatic mutation detection, chemical cleavage of mismatched heteroduplex (Cotton et al., 1988), ribonuclease cleavage of mismatched bases (Myers et al., 1985), mass spectrometry (U.S. Pat. Nos. 6,994,960, 7,074,563, and 7,198,893), nucleic acid sequencing, single strand conformation polymorphism (SSCP) (Orita et al., 1989), denaturing gradient gel electrophoresis (DGGE)(Fischer and Lerman, 1979a; Fischer and Lerman, 1979b), temperature gradient gel electrophoresis (TGGE) (Fischer and Lerman, 1979a; Fischer and Lerman, 1979b), restriction fragment length polymorphisms (RFLP) (Kan and Dozy, 1978a; Kan and Dozy, 1978b), oligonucleotide ligation assay (OLA), allele-specific PCR (ASPCR) (U.S. Pat. No. 5,639,611), ligation chain reaction (LCR) and its variants (Abravaya et al., 1995; Landegren et al., 1988; Nakazawa et al., 1994), flow-cytometric heteroduplex analysis (WO/2006/113590) and combinations/modifications thereof. Notably, gene expression levels may be determined by the serial analysis of gene expression (SAGE) technique (Velculescu et al., 1995). In general, the methods for analyzing genetic aberrations are reported in numerous publications, not limited to those cited herein, and are available to skilled practitioners. The appropriate method of analysis will depend upon the specific goals of the analysis, the condition/history of the patient, and the specific cancer(s), diseases or other medical conditions to be detected, monitored or treated. The forgoing references are incorporated herein for their teaching of these methods.

Many biomarkers may be associated with the presence or absence of a disease or other medical condition in a subject. Therefore, detection of the presence or absence of genetic variants in EGFR in a nucleic acid extraction from isolated particles, according to the methods disclosed herein, aid diagnosis of a disease or other medical condition such as NSCLC in the subject.

Further, many biomarkers may help disease or medical status monitoring in a subject. Therefore, the detection of the presence or absence of such biomarkers in a nucleic acid extraction from isolated particles, according to the methods disclosed herein, may aid in monitoring the progress or reoccurrence of a disease or other medical condition in a subject.

Many biomarkers have also been found to influence the effectiveness of treatment in a particular patient. Therefore, the detection of the presence or absence of such biomarkers in a nucleic acid extraction from isolated particles, according to the methods disclosed herein, may aid in evaluating the efficacy of a given treatment in a given patient. The identification of these biomarkers in nucleic acids extracted from isolated particles from a biological sample from a patient may guide the selection of treatment for the patient.

In certain embodiments of the foregoing aspects of the invention, the disease or other medical condition is a neoplastic disease or condition (e.g., cancer or cell proliferative disorder). In some embodiments, the disease or other medical condition is a lung cancer. In some embodiments, the disease or other medical condition is non-small cell lung cancer (NSCLC).

Kits for Isolating Microvesicles from a Biological Sample

One aspect of the present invention is further directed to kits for use in the methods disclosed herein. The kit comprises a capture surface apparatus sufficient to separate microvesicles from a biological sample from unwanted particles, debris, and small molecules that are also present in the biological sample, and a means for detecting a T790M EGFR mutation, a L858R EGFR mutation, one or more exon19 insertions and/or one or more exon19 deletions. The present invention also optionally includes instructions for using the foregoing reagents in the isolation and optional subsequent nucleic acid extraction process.

EXAMPLES

Table 1 provides the primer and probe sequences used in the study described herein:

TABLE 1

Primer/Probe Sequences for T790M, L858R, and Exon 19 Deletion/Insertion Tests

| Target | Name | Sequence/Modifications | Pre-amp Conc. µM | qPCR Reaction µM |
|---|---|---|---|---|
| EGFR exon 7 | MA15_49 | CTACAACCCCACCACGTACC (SEQ ID NO: 1) | 0.2 | 0.1 |
| | MA15_50 | GGTGGCACCAAAGCTGTATT (SEQ ID NO: 2) | 0.2 | 0.9 |
| | MA15_51 | Cy5/AGATGGATGTGAACCCCGAG/ 3IAbRQSp/-3' (SEQ ID NO: 3) | | |
| | | Cy5/ACATACCAGATGGATGTGAAC/ 3IAbRQSp/-3' (SEQ ID NO: 4) | NA* | 0.2 |
| | | Cy5/ATACCAGATGGATGTGAACC/ 3IAbRQSp/-3' (SEQ ID NO: 5) | | |
| EGFR exon 20 | MA14_55 | GCCTGCTGGGCATCT (SEQ ID NO: 6) | 0.2 | 0.7 |
| | MA15_52 | AGCCGAAGGGCATGAGCTG (SEQ ID NO: 7) | 0.2 | NA |
| | MA14_56 | 5'-/56-FAM/TCACCTCCA/ZEN/CCGTGCA/3IABkFQ/-3' (SEQ ID NO: 8) | NA | 0.2 |
| | | 5'-/56-FAM/TCCACC/ZEN/GTGCAGCT/3IABkFQ/-3' (SEQ ID NO: 9) | | |
| | | 5'-/56-FAM/ACCTCCA/ZEN/CCGTGCAGC/3IABkFQ/-3' (SEQ ID NO: 10) | | |
| | | 5'-/56-FAM/ACCGTGCAG/ZEN/CTCATCA/3IABkFQ/-3' (SEQ ID NO: 11) | | |
| | | 5'-/56-FAM/TGCACGGTG/ZEN/GAGGTGAGGC/3IABkFQ/-3' (SEQ ID NO: 12) | | |
| | | 5'-/56-FAM/TGAGCTG/ZEN/CACGGTGGA/3IABkFQ/-3' (SEQ ID NO: 13) | | |
| | | 5'-/56-FAM/TGCACGG/ZEN/TGGAGGT/3IABkFQ/-3' (SEQ ID NO: 14) | | |

TABLE 1-continued

Primer/Probe Sequences for T790M, L858R, and Exon 19 Deletion/Insertion Tests

| Target | Name | Sequence/Modifications | Pre-amp Conc. µM | qPCR Reaction µM |
|---|---|---|---|---|
| | | 5'-/56-FAM/TGATGAGCTGC/ZEN/ACGGT/3IABkFQ/-3' (SEQ ID NO: 15) | | |
| | MA15_45 | GCCGAAGGGCATGAGCTGAG (C3 spacer on 3' end)(SEQ ID NO: 16) | 0.24 | NA |
| | | 5-GCATGAGCTGC + GTGATGAG-3- (C3 spacer) (SEQ ID NO: 17) and a BNA GCCGAAGGGCATGAGCTGC + C3 blocker (SEQ ID NO: 18) | | |
| | | 5' (ZG)AGCT(ZG)C(ZG)TGATG(ZA)3'** (SEQ ID NO: 19) | | |
| | | GCATGAGCTGCGTGATGAG/3SpC3 (SEQ ID NO: 20) | | |
| | | CTCATCACGCAGCTCATGC/3InvdT (SEQ ID NO: 21) | | |
| | | 5' (ZG)GCATGAGCT(ZG)C(ZG) 3'PNA (SEQ ID NO: 22) | | |
| | | 5' (ZG)AGCT(ZG)C(ZG)TGATG(ZA)3'PNA (SEQ ID NO: 23) | | |
| | MA15_42 | 5'-GCCGAAGGGCATGAGCTGA[A] -3'*** (SEQ ID NO: 24) | NA | 0.1 |
| QBeta | MA15_46 | /5HEX/CGCCAGGCA/ZEN/TATGCTGACGTG/3IABkFQ/-3' (SEQ ID NO: 25) | NA | 0.2 |
| | MA15_47 | AACGGTTCTTGTGACCCATC (SEQ ID NO: 26) | 0.2 | 0.5 |
| | MA15_48 | CGAACAAAAGCTCGTTCCTC (SEQ ID NO: 27) | 0.2 | 0.5 |
| EGFR exon21 | MA14_120 | GGCAGCCAGGAACGTACT (SEQ ID NO: 28) | NA | NA |
| | MA17_152 | CTTCCGCACCCAGCAGTT (SEQ ID NO: 29) | NA | NA |
| | MA15_346 | 5FAM/TGGGCGGGCCAAA/MGBNFQ (SEQ ID NO: 30) | NA | NA |
| | | 5FAM/CACAGATTTTGGGCGGG/MGBNFQ (SEQ ID NO: 31) | NA | NA |
| | | 5FAM/GGGCGGGCCAAACTGCTGG/MGBNFQ (SEQ ID NO: 32) | NA | NA |
| | | 5FAM/TTGGGCGGGCCAAAC/MGBNFQ (SEQ ID NO: 33) | NA | NA |
| | | 5FAM/ACAGATTTTGGGCGGGC/MGBNFQ (SEQ ID NO: 34) | NA | NA |
| | | 5FAM/TTTGGGCGGGCCAAACT/MGBNFQ (SEQ ID NO: 35) | NA | NA |
| | | 5FAM/GATTTTGGGCGGGCCAAAC/MGBNFQ (SEQ ID NO: 36) | NA | NA |
| | MA15_150 | GTATGGCCCGCCCAAAAT (SEQ ID NO: 37) | NA | NA |
| | | CCCAGCAGTTTGGCACGG (SEQ ID NO: 38) | NA | NA |
| | | CAGTTTGGCCCTCCG (SEQ ID NO: 39) | NA | NA |
| | | GGCCCGCCCAAAACCA (SEQ ID NO: 40) | NA | NA |
| | | CACCCAGCAGTTTGGTCC (SEQ ID NO: 41) | NA | NA |
| | | GTTTGGCCCGCCCTAT (SEQ ID NO: 42) | NA | NA |
| EGFR exon19 | MA15_167 | TGGATCCCAGAAGGTGAGAA (SEQ ID NO: 43) | NA | NA |
| | MA15_163 | CGAGGATTTCCTTGTTGG (SEQ ID NO: 44) | NA | NA |
| | MA17_187 | 5FAM/AAGCCAACAAGGAAATC/ MGBNFQ (SEQ ID NO: 45) | NA | NA |
| | | 5FAM/AGGAATTAAGAGAAGCAACATC/MGBNFQ (SEQ ID NO: 46) | NA | NA |
| | | 5FAM/AGTTAAAATTCCCGTCGCTAT/MGBNFQ (SEQ ID NO: 47) | NA | NA |
| | | 5FAM/TTAAAATTCCCGTCGCTATCAA/MGBNFQ (SEQ ID NO: 48) | NA | NA |
| | | 5FAM/TTAAAATTCCCGTCGCT/MGBNFQ (SEQ ID NO: 49) | NA | NA |
| | | 5FAM/AGTTAAAATTCCCGTCG/MGBNFQ (SEQ ID NO: 50) | NA | NA |
| | | 5FAM/TTAAAATTCCCGTCGCTATC/MGBNFQ (SEQ ID NO: 51) | NA | NA |
| | | 5FAM/TAAAATTCCCGTCGCTATCA/MGBNFQ (SEQ ID NO: 52) | NA | NA |
| | MA17_182 | AGCAACCTTGATAGCGACGG (SEQ ID NO: 53) | NA | NA |
| | | CGGAGATGTTTTGATAGCGAC (SEQ ID NO: 54) | NA | NA |
| | | TGTTTTGATAGCGACGGGAAT (SEQ ID NO: 55) | NA | NA |
| | | TTTGATAGCGACGGGAATTTTAAC (SEQ ID NO: 56) | NA | NA |

TABLE 1-continued

Primer/Probe Sequences for T790M, L858R, and Exon 19 Deletion/Insertion Tests

| Target | Name | Sequence/Modifications | Pre-amp Conc. µM | qPCR Reaction µM |
|---|---|---|---|---|
| | | GATGTTTTGATAGCGACGGGAA (SEQ ID NO: 57) | NA | NA |
| | | GCTTTCGGAGATGTTTTG (SEQ ID NO: 58) | NA | NA |
| | | TTCGGAATTTTGATAGCGACG (SEQ ID NO: 59) | NA | NA |
| | | TCGGAGATTCCTTGATAGCGA (SEQ ID NO: 60) | NA | NA |
| | | CGGAGATGTTGCTTCCTTGAT (SEQ ID NO: 61) | NA | NA |
| | | GGAGATTTCCTTGATAGCGACG (SEQ ID NO: 62) | NA | NA |
| | | TTGTTGGCTTTCGATTCCTTG (SEQ ID NO: 63) | NA | NA |
| | | TTGTTGGCTTTCGAGACCTTG (SEQ ID NO: 64) | NA | NA |
| | | TTGGCTTTCGGAACCTTGATAG (SEQ ID NO: 65) | NA | NA |
| | | CTTGTTGGCTTTCGGAGACTTG (SEQ ID NO: 66) | NA | NA |
| | | CTTTCGGAGCCTTGATAGCG (SEQ ID NO: 67) | NA | NA |
| | | TTGTTGGCTTTCGGAGTCCTT (SEQ ID NO: 68) | NA | NA |
| | | CTTTCGTGTTCCTTGATAGCGA (SEQ ID NO: 69) | NA | NA |
| | | CGGAGATACCTTGATAGCGACG (SEQ ID NO: 70) | NA | NA |
| | | CGGAGATGCCTTGATAGCGA (SEQ ID NO: 71) | NA | NA |
| | | TTGTTGGCTTTCGGAGATGTCT (SEQ ID NO: 72) | NA | NA |
| | | TCGGAGATATTTTGATAGCGACG (SEQ ID NO: 73) | NA | NA |
| | | CGGAGATGTTGCGCTCCTTG (SEQ ID NO: 74) | NA | NA |
| | | GCTTTCGGAGATGTGCTCCT (SEQ ID NO: 75) | NA | NA |
| | | GGAGATGTTGGAATTTTGATAGCG (SEQ ID NO: 76) | NA | NA |
| | | GCTTTCGGAGATGTTGGTTCC (SEQ ID NO: 77) | NA | NA |
| | | TTCGGATTGTTCCTTGATAGCG (SEQ ID NO: 78) | NA | NA |
| | | CGGAGATGTCCTTGATAGCGA (SEQ ID NO: 79) | NA | NA |
| | | CGGAGATGGAATTTTGATAGCG (SEQ ID NO: 80) | NA | NA |
| | | GCTTTCGGAGATGGTTCCTTG (SEQ ID NO: 81) | NA | NA |
| | | GGCTTTCGGAGATGATTCCTT (SEQ ID NO: 82) | NA | NA |
| | | GCTTTCGGAGAAGCAACCTTG (SEQ ID NO: 83) | NA | NA |

*NA: Not applicable
**(ZG) and (ZA): Pentabase
***[A]: 2,6-diaminopurine-2'-deoxyriboside

Example 1: T790M Mutation Assay Workflow

Figure 1B:
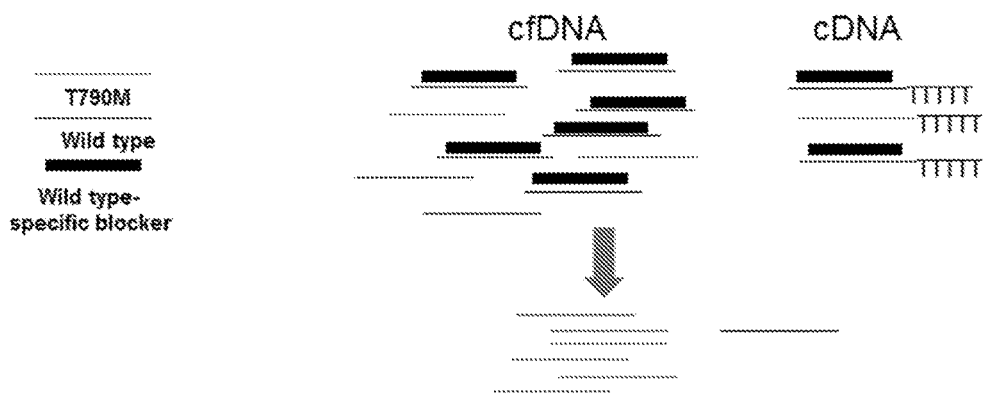
Figure 1C:
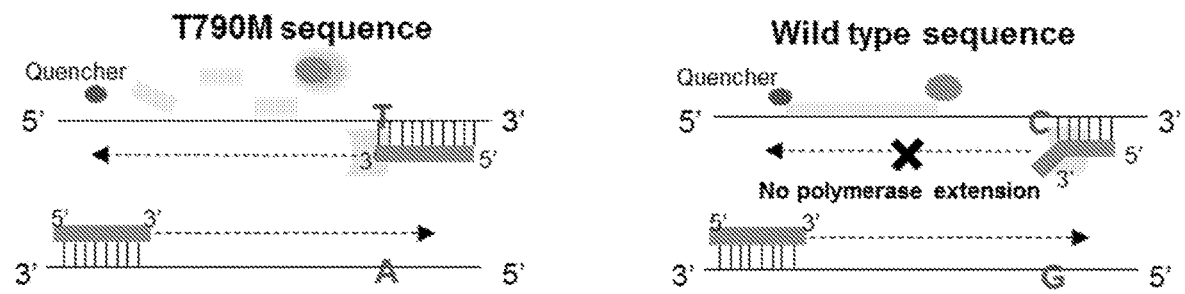

FIGS. 1A-1C are a series of illustrations of the assay workflow design and qPCR overview. FIG. 1A depicts how both extracellular NA and circulatingNA get co-isolated from plasma and reverse transcribed. At the reverse transcription step, an amplification control (DNA) and an RNA spike in control are added to ensure reverse transcription and subsequent amplifications occur (pre-amplification and multiplex qPCR). FIG. 1B depicts how multiplex pre-amplification reaction includes a wild type blocker for exon 20 of EGFR, which favors amplification of mutant molecules from circulating NA and cDNA. FIG. 1C depicts how qPCR is based on an Amplification Refractory Mutation system (ARMS).

This workflow provides a method for the detection of T790M in extracellular NA and circulating NA in biofluids from patients with NSCLC.

The assay described in this example uses the Amplification Refractory Mutation detection System (ARMS) for the qualitative and quantitative detection of T790M in exon 20 of EGFR in circulating NA and extracellular NA, obtained using the extraction procedures described in PCT Publication Nos. WO 2016/007755 and WO 2014/107571, the contents of each of which are incorporated by reference herein in their entirety.

It is understood that while Table 1 presents specific primers and probe sequences, the methods and kits of the disclosure can also use primers and/or probe sequences that comprise the sequences shown above in Table 1, or primers and/or probe sequences that are modified versions of the sequences shown above in Table 1. Modified versions of these primers and/or probe sequences can include, by way of non-limiting example, adding one or more nucleotides to the 5' end, adding one or more nucleotides to the 3' end, adding one or more nucleotides to both the 5' end and the 3' end, adding tails, shortening the sequences, lengthening the sequences, moving the sequences a few bases up or downstream, or any combination thereof.

Furthermore, it is understood that the concentrations provided in Table 1 are exemplary. The methods and kits of the disclosure can use any suitable concentration of the pre-amplification concentration, the qPCR reaction concentration, or a combination thereof. For example, in some embodiments, the pre-amplification concentration, the qPCR reaction concentration, or a combination thereof is a concentration in the range of about 0.05 µM to about 1 µM and any value in between.

The methods and kits of the disclosure can use any suitable concentration of the pre-amplification concentration, the qPCR reaction concentration, or a combination thereof. For example, in some embodiments, the pre-amplification concentration, the qPCR reaction concentration, or a combination thereof is a concentration in the range of about 0.05 µM to about 100 µM and any value in between, such as about 0.05 µM to about 20 µM, about 0.05 µM to about 1 µM, about 1 µM to about 10 µM, more particularly about 1 µM, about 2 µM, about 4 µM, about 8 µM, about 10 µM, about 15 µM, or about 20 µM.

Tables 2 and 3 depict the conditions used for the pre-amplification and qPCR primer mix used in the study described herein.

TABLE 2

Preparation of 50× Pre-Amplification Primer Mix

| Stock Concentration | Component | Volume | Final Concentration |
|---|---|---|---|
| NA | H$_2$O | 14 | NA* |
| 100 µM | MA15_49 | 5 | 10 µM |
| 100 µM | MA15_50 | 5 | 10 µM |
| 100 µM | MA15_47 | 5 | 10 µM |
| 100 µM | MA15_48 | 5 | 10 µM |
| 100 µM | MA14_55 | 5 | 10 µM |
| 100 µM | MA15_52 | 5 | 10 µM |
| 100 µM | MA15_45 | 6 | 12 µM |
| | Final reaction Volume | 50 µL | |

TABLE 3

Preparation of 20× qPCR Assay Mix

| Stock Concentration | Component | Volume | Final Concentration |
|---|---|---|---|
| NA | H$_2$O | 32 | NA* |
| 100 µM | MA14_55 | 14 | 14 µM |
| 100 µM | MA15_42 | 2 | 2 µM |
| 100 µM | MA14_56 | 4 | 4 µM |
| 100 µM | MA15_49 | 2 | 2 µM |
| 100 µM | MA15_50 | 18 | 18 µM |
| 100 µM | MA15_51 | 4 | 4 µM |
| 100 µM | MA15_47 | 10 | 10 µM |
| 100 µM | MA15_48 | 10 | 10 µM |
| 100 µM | MA15_46 | 4 | 4 µM |
| | Final reaction Volume | 100 uL | |

It is understood that the concentrations provided in Tables 2 and 3 are exemplary. The methods and kits of the disclosure can use any suitable concentration of the pre-amplification concentration, the qPCR reaction concentration, or a combination thereof. For example, in some embodiments, the pre-amplification concentration, the qPCR reaction concentration, or a combination thereof is a concentration in the range of about 0.05 µM to about 1 µM and any value in between.

Tables 4 and 5 depict the reverse transcription (RT) mix for the sample and control RT reactions. The following cycling conditions were used: 25° C. for 10 minutes; 42° C. for 70 minutes; 85° C. for 5 minutes; Hold at 4° C.

TABLE 4

Preparation of Sample RT Reactions

| Component | Sample | Master Mix (for 9 samples plus QBeta control) |
|---|---|---|
| 5× VILO Reaction Mix | 4.8 | 52.8 |
| 10× SuperScript Enzyme Mix | 2.4 | 26.4 |
| Exosomal RNA and cfDNA | 14 | — |
| 4 × 10$^3$ QBeta RNA spike | 1 | 11 |
| H$_2$O | 1.8 | 19.8 |
| Final RT Reaction Volume | 24 | — |

TABLE 5

Preparation of Control RT Reactions

| Component | Negative Control RT-VILO Mix | Positive Control RT-VILO Mix |
|---|---|---|
| 5× VILO Reaction Mix | 4.8 | 4.8 |
| 10× SuperScript Enzyme Mix | 2.4 | 2.4 |
| 48 copies of T790M/Exon 7 gblock (added in DNA lab) | — | 2.08 |
| H$_2$O | 16.8 | 14.72 |
| Final RT Reaction Volume | 24 | 24 |

It is understood that the reactions and mixtures provided in Tables 4 and 5 are exemplary. The methods and kits of the disclosure can use any suitable reactions and mixtures. For example, in some embodiments, the reaction and/or mixture is based on the reactions and mixtures provided in Tables 4 and 5, for example, using the mixtures and/or reactions in combination with any other suitable first strand DNA synthesis kit.

Furthermore, it is understood that while the examples provided herein incorporate separate reverse transcription and pre-amplification steps, the methods and kits of the disclosure can also use a single step process of revere transcription and pre-amplification.

Tables 6A and 6B provide the pre-amplification master mix and the cycling conditions used in the pre-amplification reaction.

TABLE 6A

Preparation of Pre-Amplification Master Mix

| Master Mix Stock Concentration | Pre-Amplification Assay Component | Volume/ Reaction (µL) | Final Concentration |
|---|---|---|---|
| 2× | Q5 ® Hot Start High-Fidelity 2× Master Mix | 25 | 1× |
| 50× | Preamp Primer Mix | 1 | 1× |
| | Input Template-RT Reaction | 24 | |

TABLE 6B

Cycling conditions:

| Cycling conditions | |
|---|---|
| Initial denaturation | 98° C. for 3 minutes |
| 14 cycles | 98° C. for 10 seconds |
| | 60° C. for 20 seconds |
| | 72° C. for 10 seconds |
| Final extension | 72° C. for 2 minutes |
| Hold | 4° C. |

It is understood that the mixture in Table 6A and the cycling conditions in Table 6B are exemplary. The methods and kits of the disclosure can use any suitable mixtures and/or cycling conditions. For example, in some embodiments, the mixture is based on the mixture provided in Table 6A, for example, using a modified version of the mixture provided in Table 6A. Modified versions of the mixture can include, by way of non-limiting example, the use of any suitable high fidelity enzyme and/or the use of any suitable RT reaction template including, but not limited to, a fragment of the RT reaction template shown in Table 6A.

Furthermore, it is understood that the cycling conditions provided in Table 6B are exemplary. The methods and kits of the disclosure can use any suitable cycling conditions. For example, the cycling conditions can be modified based on the cycling conditions shown in Table 6B, for example, at a temperature that is within about 5-10% of the values shown in Table 6B, e.g., 5° C. of the values shown in Table 6B, and/or a time that is within about 5-10% of the values shown in Table 6B.

Tables 7A and 7B provide the qPCR reaction mix and cycling conditions"

TABLE 7A

Preparation of qPCR Master Mix

| Master Mix Stock Concentration | Triplex qPCR Assay Component | Volume/ Reaction (µL) | Final Concentration |
|---|---|---|---|
| NA | H$_2$O | 8.75 | NA |
| 2× | Rotor-Gene Multiplex PCR Kit | 12.5 | 1× |
| 50× | ROX | 0.5 | |
| 20× | Assay Mix | 1.25 | 1× |
| | Input Template | 2 | — |
| | Final Reaction Volume | 25 | |

TABLE 7B

Cycling Conditions
Cycling conditions

| Hold | 95° C. | 5 minutes |
|---|---|---|
| Cycle × 40 | 95° C. | 15 seconds |
| | 60° C. | 1 minute |

It is understood that the mixture in Table 7A and the cycling conditions in Table 7B are exemplary. The methods and kits of the disclosure can use any suitable mixtures and/or cycling conditions. For example, in some embodiments, the mixture is based on the mixture provided in Table 7A, for example, using a modified version of the mixture provided in Table 7A. Modified versions of the mixture can include, by way of non-limiting example, the use of any suitable master mix and/or the use of any suitable RT reaction template including, but not limited to, a fragment of the RT reaction template shown in Table 7A.

Furthermore, it is understood that the cycling conditions provided in Table 7B are exemplary. The methods and kits of the disclosure can use any suitable cycling conditions. For example, the cycling conditions can be modified based on the cycling conditions shown in Table 7B, for example, at a temperature that is within about 5-10% of the values shown in Table 7B, e.g., 5° C. of the values shown in Table 7B, and/or a time that is within about 5-10% of the values shown in Table 7B.

The assay is tested on plasma from 210 patient samples. Of these, 105 of the NSCLC samples were classified as EGFR T790M positive at baseline by tissue analysis (i.e., prior to treatment with mutant-selective inhibitor of EGFR), and 105 are either NSCLC samples negative by formalin-fixed paraffin-embedded (FFPE) tissue analysis, or were obtained from individual or pooled healthy donors. Half of the samples from each category (T790M positive by tissue analysis or negative) are used as the training cohort and the remainder for the validation cohort.

Within the 51 samples from the validation cohort classified as T790M positive by FFPE analysis, approximately 37% (19/51) are patients with intrathoracic (M0-M1a) disease or unknown M stage (MX) that have historically been very difficult to detect by circulating NA analysis alone (without the extracellular NA component).

Additional analytical validation for this assay was performed using 89 individual spike-ins of varying concentrations of T790M (0.75-2660 copies/mL) into healthy pooled plasma by different operators and on different days.

The clinical cohort of 210 samples is split into stage matched training and validation cohorts. The optimal Ct cutoff threshold value(s) is estimated by maximizing Youden's J statistic on 100 bootstraps of the training data with an 80% sub-training and 20% sub-testing split. Average analytical sensitivity and specificity on the training cohort is 91% (±9%) and 95% (±6%) respectively with an average AUC of 94% (±6%). Average precision, NPV and PPV were 95% (±6%), 92% (±7%) and 95% (±6%) respectively. The validation cohort has a sensitivity of 92% and a specificity of 89% along with an AUC of 96%, with precision, NPV and PPV being 89%, 92% and 89% respectively.

The derived clinical cutoff threshold value(s) in T790M test includes a series of values to be met in order for a sample to be called positive. For example, the sample wells that did not fulfill the following quality filters for the positive, negative and/or QBeta controls were excluded: Exon20 Ct between 10 and 40, preferably between 15 and 35; Exon7 Ct values between 15 and 35, preferably between 20 and 30; Negative control (RT and qPCR steps) Ct values larger than 30, preferably larger than 35; QBeta control Ct values between 15 to 30, preferably between 20 to 25; QBeta assay (control of inhibition): delta Ct (Ct sample-Ct control well) smaller than 20, preferably 10; T790M assay positive: delta Ct (Ct sample-Ct control well) smaller than 30, preferably 25; Exon 7 assay valid: Ct sample smaller than 25, preferably 20.

Figure 2:
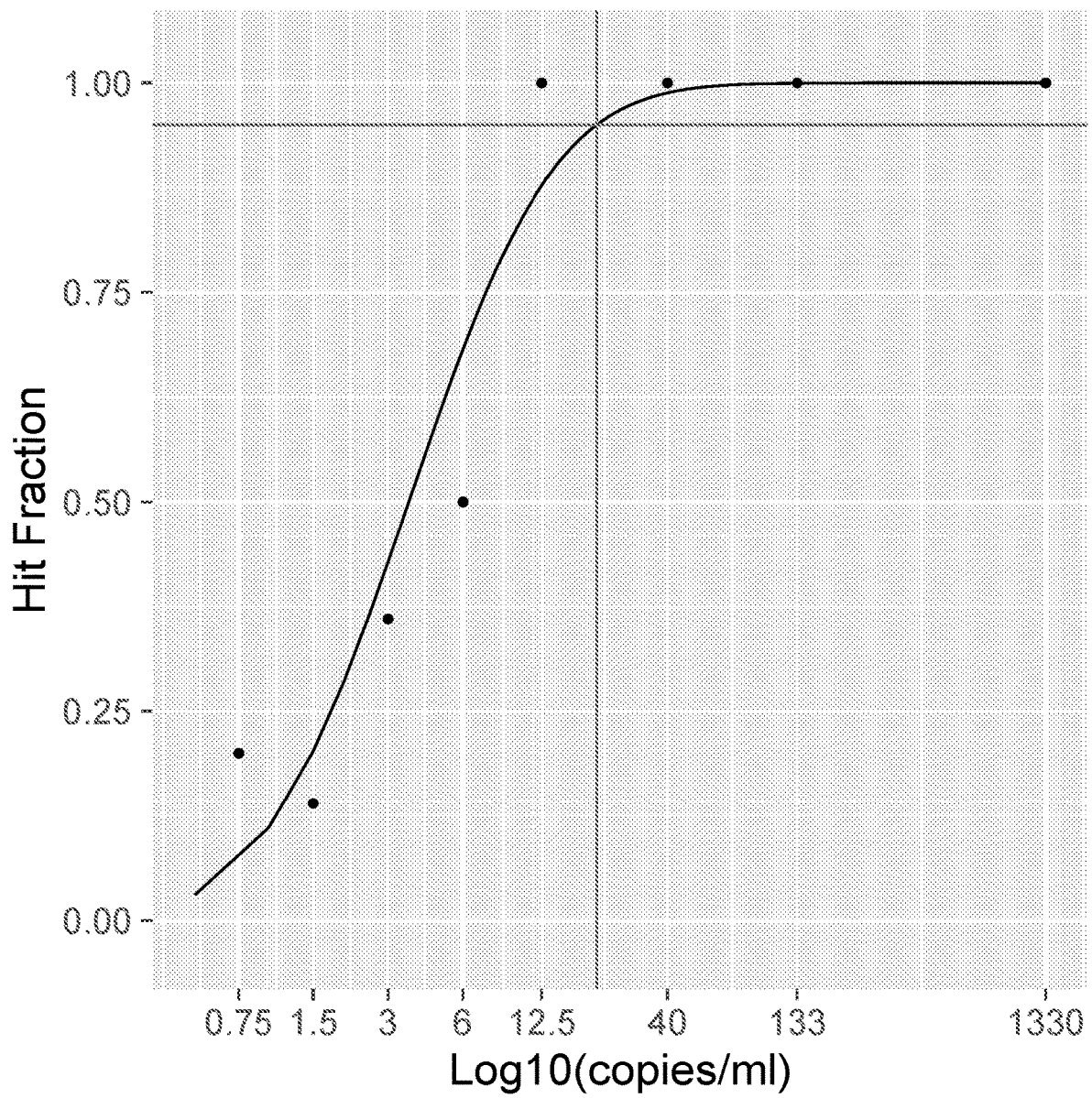
FIG. 2 is a graph depicting the analytical performance of the T790M detection assay shown in FIG. 1. Each data point represents up to 14 independent experiments. Data has been plotted using log 10 scale, but copies of T790M/mL are shown for visual aid.

FIG. 2 is a graph depicting the analytical performance of the T790M detection assay used in this study. Canchola et al. ("Limit of Detection (LoD) Estimation Using Parametric Curve Fitting to (Hit) Rate Data: The LoD_Est SAS® Macro." Working paper (2016), available at DOI: 10.13140/ RG.2.1.3622.9203) define The Limit of Detection (LoD) as the lowest concentration or amount of material, target or analyte that is consistently detectable (CI 95%). As shown in FIG. 2, the LOD of the study described herein is 21 copies/mL (95% CI: 9-38 copies/mL). 1.5 copies/mL was detected 14% of the time and 12.5 copies/mL was detected 100% of the time. LOD is only limited by the presence of material.

Figure 3:
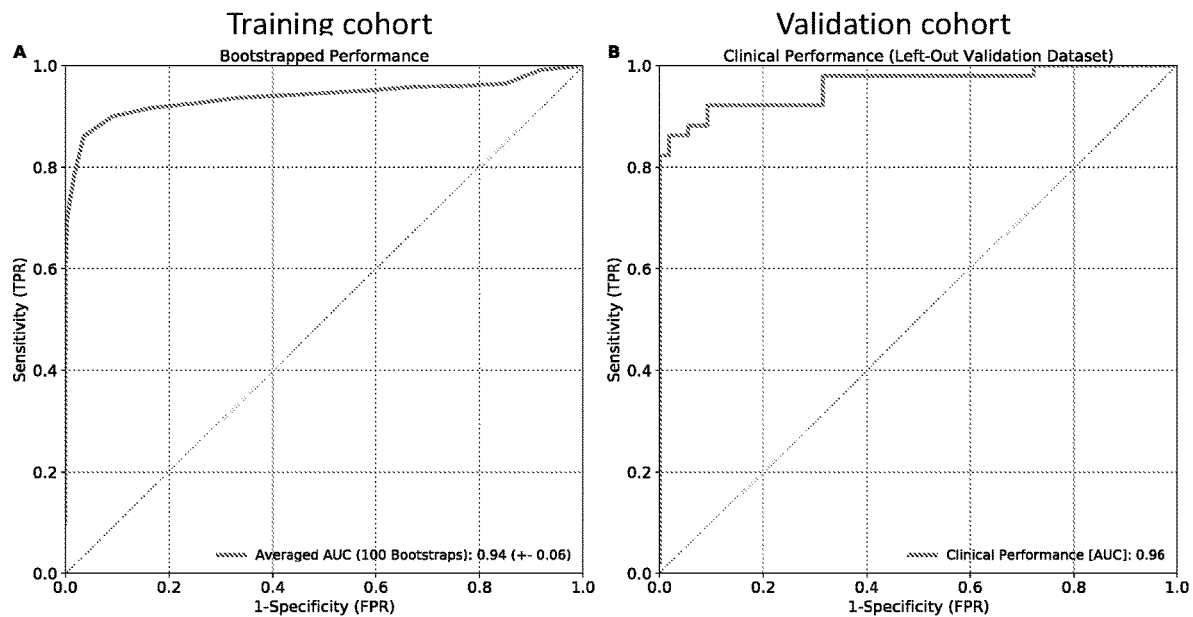
FIG. 3 is a graph depicting the clinical performance of the T790M detection assay shown in FIG. 1.

FIG. 3 is a graph depicting the clinical performance of the T790M detection assay on the clinical validation cohort. The AUC was 96% on the validation cohort.

This is the first CLIA-validated qPCR-based method that combines circulating NA and extracellular NA and can detect T790M in this sample selection (where 37% of the patients had intrathoracic or unknown disease stage) with 92% sensitivity and 89% specificity. This is the highest level of sensitivity and specificity reported to date.

Example 2: Development of T790M Assay

The studies described herein demonstrate the advantages of using a short amplicon and a modified nucleotide in the ARMS primer to detect and analysis highly fragmented sample material.

Figure 4:
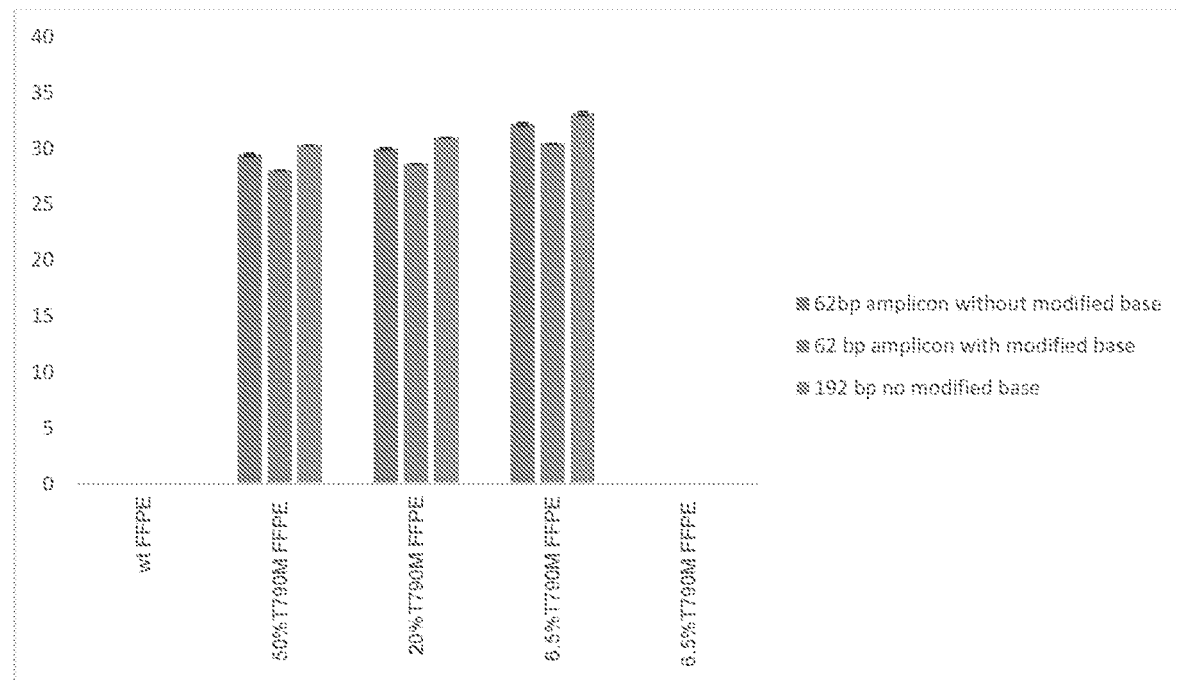
FIG. 4 is a graph depicting a comparison of a large versus short amplicon (with or without a base modification) to detect mutations in highly degraded DNA.

FIG. 4 is a graph depicting a comparison of a large versus short amplicon (with or without the base modification) to detect mutations in highly degraded DNA. Using commercially available FFPE with known % of T790M (wild type, 50%, 20%, 6.5%) and different amplicon sizes 192 bp (see e.g., Leelatian et al., "Highly sensitive EGFR mutation detection by specific amplification of mutant alleles." Exp Mol Pathol., vol. 96(1): 85-91 (2014)) and 62 bp with and without the base modification on the primer. FIG. 4 demonstrates that 62 bp with the base modification yields the earliest Ct value.

Figure 5A:
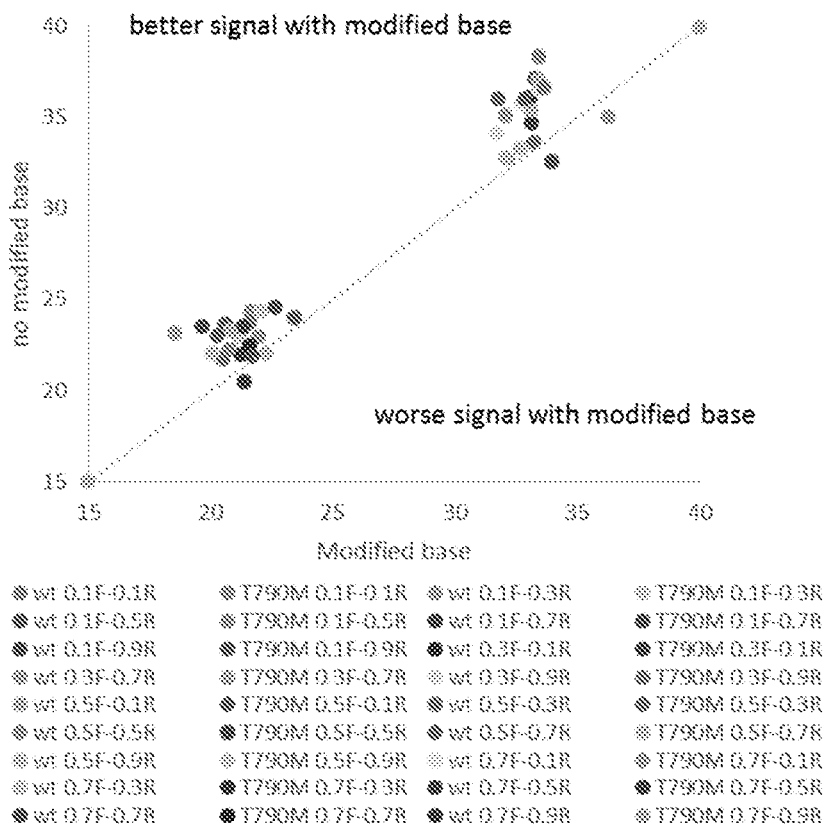
FIGS. 5A and 5B are a series of graphs depicting a comparison of ARMS primers that include a base modification and ARMS primers that do not include a base modification.
Figure 5B:
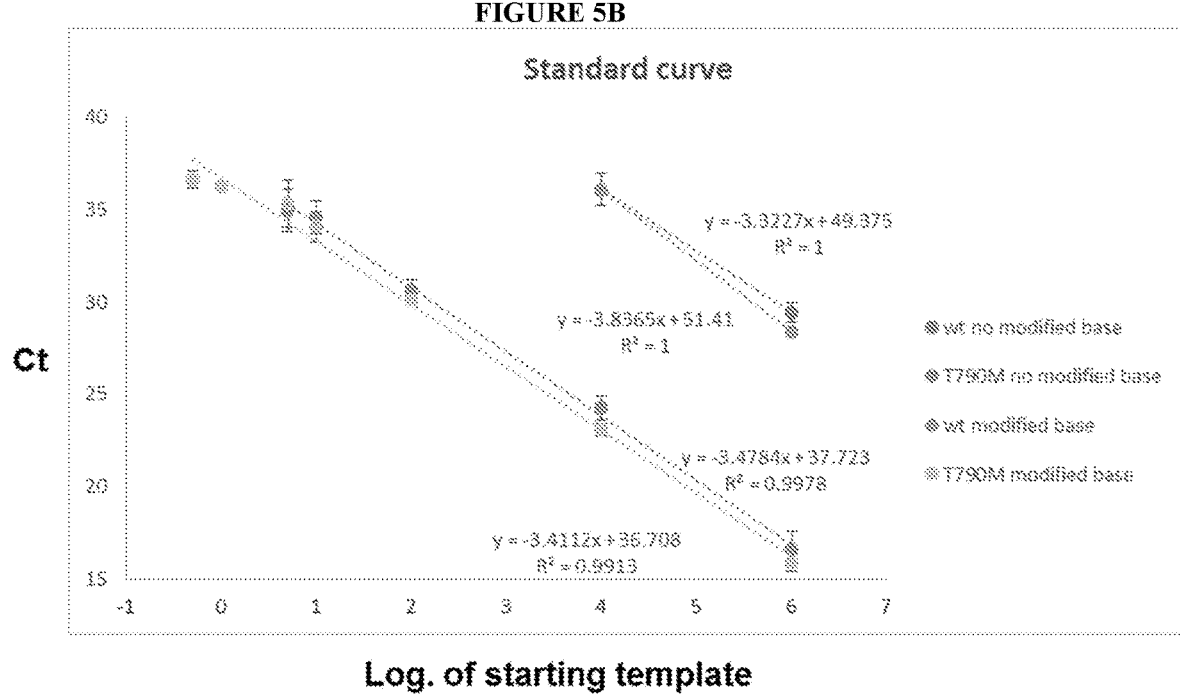

FIGS. 5A and 5B are a series of graphs depicting a comparison of ARMS primers that include a modified nucleotide and ARMS primers that do not include a modified nucleotide. These graphs demonstrate an advantage in terms of earlier Ct for T790M when a base modification was incorporated into the ARMS primer. Efficiency and linearity for best two conditions are shown FIG. 5B.

Figure 6:
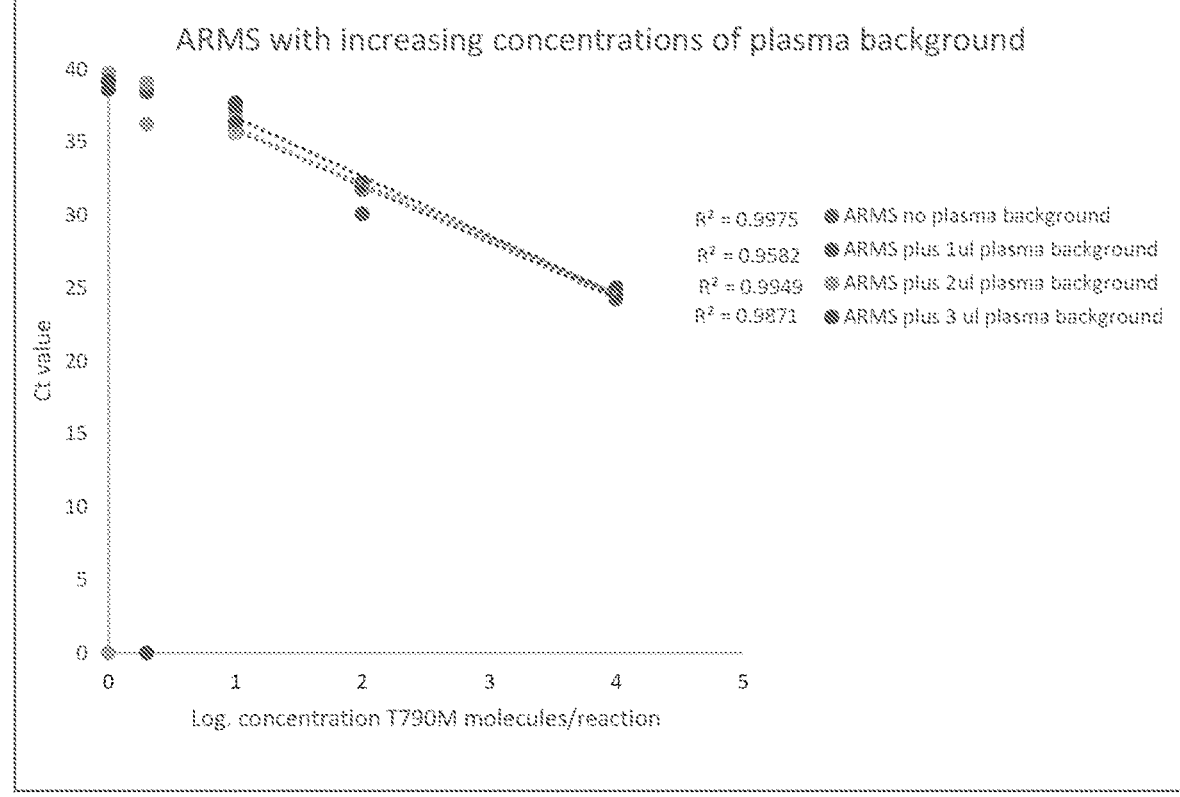
FIG. 6 is a graph that demonstrates the ability of the assay described herein to accommodate increasing amounts of exoNA and circulatingNA from normal healthy plasma.

FIG. 6 is a graph that demonstrates the ability of the assay described herein to accommodate increasing amounts of extracellular NA and circulating NA from normal healthy plasma.

Example 3: L858R and Exon 19 Deletion/Insertion Mutation Assay Workflow

The assay workflow for L858R and Exon 19 deletion/insertion mutation detection also conforms to what is disclosed in FIGS. 1A-1C. FIG. 1A depicts how both extracellular NA and circulatingNA are co-isolated from plasma and reverse transcribed. At the reverse transcription step, an amplification control (DNA) and an RNA spike in control are added to ensure reverse transcription and subsequent amplifications occur (pre-amplification and multiplex qPCR). FIG. 1B depicts how multiplex pre-amplification reaction includes a wild type blocker for corresponding wild type of L858R and exon 19 deletion and insertion mutations of EGFR, which favors amplification of mutant molecules from circulating NA and cDNA. FIG. 1C depicts how qPCR is based on an Amplification Refractory Mutation system (ARMS).

This workflow provides a method for the detection of L858R and exon 19 deletion and insertion mutations in extracellular NA and circulating NA in biofluids from patients with NSCLC.

The assay described in this example uses the Amplification Refractory Mutation detection System (ARMS) for the qualitative and quantitative detection of L858R and exon 19 deletion and insertion mutations of EGFR in circulating NA and extracellular NA, obtained using the extraction procedures described in PCT Publication Nos. WO 2016/007755 and WO 2014/107571, the contents of each of which are incorporated herein in their entirety.

It is understood that while Table 1 presents specific primers and probe sequences, the methods and kits of the disclosure can also use primers and/or probe sequences that comprise the sequences shown above in Table 1, or primers and/or probe sequences that are modified versions of the sequences shown therein. Modified versions of these primers and/or probe sequences can include, by way of non-limiting example, adding one or more nucleotides to the 5' end, adding one or more nucleotides to the 3' end, adding one or more nucleotides to both the 5' end and the 3' end, adding tails, shortening the sequences, lengthening the sequences, moving the sequences a few bases up or downstream, or any combination thereof.

Furthermore, it is understood that the concentrations disclosed in this invention are exemplary. The methods and kits of the disclosure can use any suitable concentration of the pre-amplification concentration, the qPCR reaction concentration, or a combination thereof. For example, in some embodiments, the pre-amplification concentration, the qPCR reaction concentration, or a combination thereof is a concentration in the range of about 0.05 µM to about 1 µM and any value in between.

In some embodiments, PCR enhancers or PCR additives are included in the pre-amplification or qPCR reactions, or combinations of reactions thereof. The enhancers and additives are selected from the list consisting of 7-deaza-2'-deoxyguanosine; 7-deaza dGTP, betaine (N,N,N-trimethylglycine, BSA (bovine serum albumin), DMSO (dimethyl sulfoxide), formamide, non-ionic detergents e.g. triton X-100, tween 20 or Nonidet P-40 (NP-40), TMAC (tetramethylammonium chloride), AmpFLSTR™ and aptamer.

The methods and kits of the disclosure can use any suitable concentration of the pre-amplification concentration, the qPCR reaction concentration, or a combination thereof. For example, in some embodiments, the pre-amplification concentration, the qPCR reaction concentration, or a combination thereof is a concentration in the range of about 0.05 µM to about 100 µM and any value in between, such as about 0.05 µM to about 20 µM, about 0.05 µM to about about 1 µM, about 1 µM to about 10 µM, more particularly about 1 µM, about 2 µM, about 4 µM, about 8 µM, about 10 µM, about 15 µM, or about 20 µM.

The methods and kits of the disclosure can use any suitable reactions and mixtures.

Furthermore, it is understood that while the examples provided herein incorporate separate reverse transcription and pre-amplification steps, the methods and kits of the disclosure can also use a single step process of revere transcription and pre-amplification, or no pre-amplification.

The methods and kits of the disclosure can use any suitable mixtures and/or cycling conditions. The mixture can include, by way of non-limiting example, the use of any suitable high-fidelity enzyme and/or the use of any suitable RT reaction template including, but not limited to, a fragment of the RT reaction template.

The mixture can include, by way of non-limiting example, the use of any suitable master mix and/or the use of any suitable RT reaction template including, but not limited to, a fragment of the RT reaction template.

Table 1 is a listing of sequences used for L858R (exon 21) mutation test probes, as well as a listing of sequences used for exon 19 deletion/insertion mutation test probes.

Figure 7:
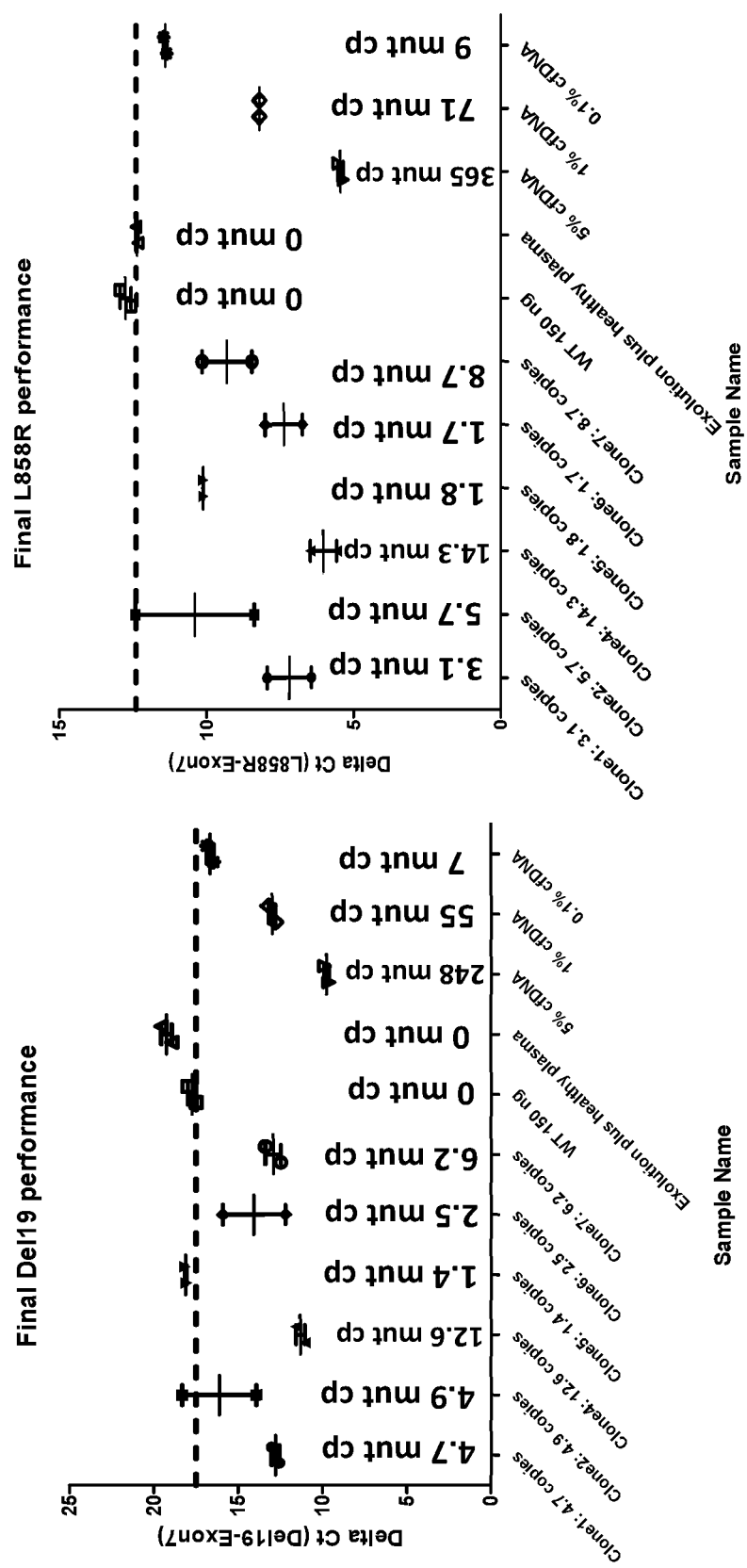
FIG. 7 is a graph demonstrating the performance of L858R and Del19 detection assays. As shown in the graph there is a clear separation between the wild type sample and the mutant samples.

FIG. 7 is a graph demonstrating the performance of L858R and Del19 detection assays. As shown in the graph there is a clear separation between the wild type sample and the mutant samples.

The derived clinical cutoff threshold values in L858R and exon 19 deletion/insertion tests comprise a series of values to be met in order for a sample to be called positive. By way of not limiting, the sample wells that did not fulfill the following quality filters for the positive, negative and/or QBeta controls were excluded: Exon 19 or Exon 21 Ct between 10 and 40, preferably between 15 and 35; Exon7 Ct values between 15 and 35, preferably between 20 and 30; Negative control (RT and qPCR steps) Ct values larger than 30, preferably larger than 35; QBeta control Ct values between 15 to 30, preferably between 20 to 25; QBeta assay (control of inhibition): delta Ct (Ct sample-Ct control well) smaller than 20, preferably 10; L858R and exon 19 deletion/insertion assay positive: delta Ct (Ct sample-Ct control well) smaller than 30, preferably 25; Exon 7 assay valid: Ct sample smaller than 25, preferably 20.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed is:

1. A method for treating lung cancer in a subject in need thereof comprising:
  (a) extracting RNA and DNA from at least one microvesicle isolated from a plasma sample from the subject;
  (b) isolating at least one circulating nucleic acid from the plasma sample;
  (c) performing a reverse transcription reaction using the RNA and DNA extracted from the at least one microvesicle and the at least one circulating nucleic acid;
  (d) performing a pre-amplification reaction of the products of step (c), wherein the preamplification reaction step is a multiplex pre-amplification reaction that comprises a wildtype blocker for exon 20 of the Epidermal Growth Factor Receptor (EGFR) gene;
  (e) detecting the amount of at least one Epidermal Growth Factor Receptor (EGFR) variant and the amount of exon 7 of the EGFR gene in the products of step (d) using quantitative PCR (qPCR), wherein the at least one EGFR variant is $EGFR^{T790M}$;
  (f) comparing each amount detected in step (e) to a corresponding pre-defined cutoff threshold to determine the presence or the absence of the EGFR variant in the plasma sample; and
  (g) administering to the subject at least one anti-cancer therapy when the EGFR variant is determined to be present in the plasma sample.

2. The method of claim 1, wherein the at least one circulating nucleic acid comprises cell-free DNA, cell-free RNA, necrotic DNA, necrotic RNA or any combination thereof.

3. The method of claim 1, further comprising prior to step (a), adding a known quantity of at least one control nucleic acid to the plasma sample, and wherein step (e) comprises detecting the amount of the at least one control nucleic acid.

4. The method of claim 1, wherein the wild type blocker comprises a hydrophobic nucleic acid, a bridge nucleic acid, a peptide nucleic acid, an oligonucleotide comprising a 3' end terminator or any combination thereof.

5. The method of claim 1, wherein the qPCR comprises a mutant-specific amplification system, a mutation-biased amplification system or any combination thereof.

6. The method of claim 1, wherein the qPCR comprises an Amplification Refractory Mutation system (ARMS).

7. The method of claim 6, wherein the ARMS comprises at least one primer comprising at least one modified nucleotide, at least one primer comprising at least one modified base, at least one primer comprising at least one modified sequence, at least one probe comprising at least one modified nucleotide, at least one probe comprising at least one modified base, at least one probe comprising at least one modified sequence or any combination thereof.

8. The method of claim 7, wherein the ARMS comprises at least one primer comprising 2-aminopurine, 8-amino-2'-deoxyadenosine, trimetroxystilbene, C-5 propynyl-deoxycytidine, C-5 propynyl-deoxyuridine, 2-amino-2'-deoxyadenosine-5'-triphosphate, 2,6-diaminopurine (2-amino-dA), inverted dT, inverted dideoxy-T, hydroxymethyl dC, iso-dC, 5-methyl dC, aminoethyl-phenoxazine-deoxycytidine, locked nucleic acids, at least one mismatched base or any combination thereof.

9. The method of claim 1, wherein the lung cancer is non-small cell lung cancer.

10. The method of claim 1, wherein the anti-cancer therapy comprises administering to the subject at least one therapeutically effective amount of an EGFR inhibitor.

11. The method of claim 10, wherein the EGFR inhibitor is gefitinib, erlotinib, lapatinib, cetuximab, panitumumab, vandetanib, neratinib, necitumumab, osimertinib or any combination thereof.

12. The method of claim 1, wherein the anti-cancer therapy comprises administering to the subject at least one therapeutically effective amount of a second generation tyrosine kinase EGFR inhibitor, a third generation tyrosine kinase EGFR inhibitor, an $EGFR^{T790M}$-targeting compound, an $EGFR^{L858R}$-targeting compound, a compound that targets EGFR comprising at least one exon 19 insertion, a compound that targets EGFR comprising at least one exon 19 deletion or any combination thereof.

* * * * *

UNITED STATES PATENT AND TRADEMARK OFFICE
CERTIFICATE OF CORRECTION

PATENT NO. : 11,427,864 B2
APPLICATION NO. : 16/463820
DATED : August 30, 2022
INVENTOR(S) : Skog et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 265 days.

Signed and Sealed this
Twenty-first Day of January, 2025

Coke Morgan Stewart
*Acting Director of the United States Patent and Trademark Office*

```
                          SEQUENCE LISTING

<160> NUMBER OF SEQ ID NOS: 83

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
ctacaacccc accacgtacc                                                   20

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
ggtggcacca aagctgtatt                                                   20

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 3
agatggatgt gaaccccgag                                                   20

<210> SEQ ID NO 4
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 4
acataccaga tggatgtgaa c                                                 21

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 5
ataccagatg gatgtgaacc                                                   20

<210> SEQ ID NO 6
<211> LENGTH: 15
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
gcctgctggg catct                                                    15

<210> SEQ ID NO 7
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
agccgaaggg catgagctg                                                19

<210> SEQ ID NO 8
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 8
tcacctccac cgtgca                                                   16

<210> SEQ ID NO 9
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 9
tccaccgtgc agct                                                     14

<210> SEQ ID NO 10
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 10
acctccaccg tgcagc                                                   16

<210> SEQ ID NO 11
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 11
accgtgcagc tcatca                                                   16
```

<210> SEQ ID NO 12
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 12
tgcacggtgg aggtgaggc                                                    19

<210> SEQ ID NO 13
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 13
tgagctgcac ggtgga                                                       16

<210> SEQ ID NO 14
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 14
tgcacggtgg aggt                                                         14

<210> SEQ ID NO 15
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 15
tgatgagctg cacggt                                                       16

<210> SEQ ID NO 16
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
gccgaagggc atgagctgag                                                   20

<210> SEQ ID NO 17
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:

```
      Synthetic primer"
<220> FEATURE:
<221> NAME/KEY: modified_base
<222> LOCATION: (12)..(12)
<223> OTHER INFORMATION: Locked nucleic acid

<400> SEQUENCE: 17
gcatgagctg cgtgatgag                                                19

<210> SEQ ID NO 18
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (20)..(20)
<223> OTHER INFORMATION: Locked nucleic acid

<400> SEQUENCE: 18
gccgaagggc atgagctgcg                                               20

<210> SEQ ID NO 19
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (1)..(1)
<223> OTHER INFORMATION: Pentabase
<220> FEATURE:
<221> NAME/KEY: modified_base
<222> LOCATION: (6)..(6)
<223> OTHER INFORMATION: Pentabase
<220> FEATURE:
<221> NAME/KEY: modified_base
<222> LOCATION: (8)..(8)
<223> OTHER INFORMATION: Pentabase
<220> FEATURE:
<221> NAME/KEY: modified_base
<222> LOCATION: (14)..(14)
<223> OTHER INFORMATION: Pentabase

<400> SEQUENCE: 19
gagctgcgtg atga                                                     14

<210> SEQ ID NO 20
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
gcatgagctg cgtgatgag                                                19

<210> SEQ ID NO 21
<211> LENGTH: 20
<212> TYPE: DNA
<213> ORGANISM: Artificial Sequence
<220> FEATURE:
<221> NAME/KEY: source
```

-continued

<223> OTHER INFORMATION: /note="Description of Artificial Sequence:
      Synthetic primer"

<400> SEQUENCE: 21
ctcatcacgc agctcatgct                                                    20

<210> SEQ ID NO 22
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (1)..(1)
<223> OTHER INFORMATION: Pentabase
<220> FEATURE:
<221> NAME/KEY: modified_base
<222> LOCATION: (11)..(11)
<223> OTHER INFORMATION: Pentabase
<220> FEATURE:
<221> NAME/KEY: modified_base
<222> LOCATION: (13)..(13)
<223> OTHER INFORMATION: Pentabase

<400> SEQUENCE: 22
ggcatgagct gcg                                                           13

<210> SEQ ID NO 23
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (1)..(1)
<223> OTHER INFORMATION: Pentabase
<220> FEATURE:
<221> NAME/KEY: modified_base
<222> LOCATION: (6)..(6)
<223> OTHER INFORMATION: Pentabase
<220> FEATURE:
<221> NAME/KEY: modified_base
<222> LOCATION: (8)..(8)
<223> OTHER INFORMATION: Pentabase
<220> FEATURE:
<221> NAME/KEY: modified_base
<222> LOCATION: (14)..(14)
<223> OTHER INFORMATION: Pentabase

<400> SEQUENCE: 23
gagctgcgtg atga                                                          14

<210> SEQ ID NO 24
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (20)..(20)
<223> OTHER INFORMATION: 2,6-diaminopurine-2'-deoxyriboside

<400> SEQUENCE: 24
gccgaagggc atgagctgaa                                              20

<210> SEQ ID NO 25
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 25
cgccaggcat atgctgacgt g                                            21

<210> SEQ ID NO 26
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
aacggttctt gtgacccatc                                              20

<210> SEQ ID NO 27
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
cgaacaaaag ctcgttcctc                                              20

<210> SEQ ID NO 28
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
ggcagccagg aacgtact                                                18

<210> SEQ ID NO 29
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
cttccgcacc cagcagtt                                                18

<210> SEQ ID NO 30
<211> LENGTH: 13
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic probe"

<400> SEQUENCE: 30
tgggcgggcc aaa                                                      13

<210> SEQ ID NO 31
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 31
cacagatttt gggcggg                                                  17

<210> SEQ ID NO 32
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 32
gggcgggcca aactgctgg                                                19

<210> SEQ ID NO 33
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 33
ttgggcgggc caaac                                                    15

<210> SEQ ID NO 34
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 34
acagattttg gcgggc                                                   17

<210> SEQ ID NO 35
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 35
tttgggcggg ccaaact                                                  17

<210> SEQ ID NO 36
```

```
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 36
gattttgggc gggccaaac                                                    19

<210> SEQ ID NO 37
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
gtatggcccg cccaaaat                                                     18

<210> SEQ ID NO 38
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
cccagcagtt tggcacgg                                                     18

<210> SEQ ID NO 39
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
cagtttggcc ctccg                                                        15

<210> SEQ ID NO 40
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
ggcccgccca aaacca                                                       16

<210> SEQ ID NO 41
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41
```

```
cacccagcag tttggtcc                                                  18

<210> SEQ ID NO 42
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
gtttggcccg ccctat                                                    16

<210> SEQ ID NO 43
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
tggatcccag aaggtgagaa                                                20

<210> SEQ ID NO 44
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
cgaggatttc cttgttgg                                                  18

<210> SEQ ID NO 45
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 45
aagccaacaa ggaaatc                                                   17

<210> SEQ ID NO 46
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 46
aggaattaag agaagcaaca tc                                             22

<210> SEQ ID NO 47
<211> LENGTH: 21
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic probe"

<400> SEQUENCE: 47
agttaaaatt cccgtcgcta t                                              21

<210> SEQ ID NO 48
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 48
ttaaaattcc cgtcgctatc aa                                             22

<210> SEQ ID NO 49
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 49
ttaaaattcc cgtcgct                                                   17

<210> SEQ ID NO 50
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 50
agttaaaatt cccgtcg                                                   17

<210> SEQ ID NO 51
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 51
ttaaaattcc cgtcgctatc                                                20

<210> SEQ ID NO 52
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 52
taaaattccc gtcgctatca                                                20
```

```
<210> SEQ ID NO 53
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
agcaaccttg atagcgacgg                                              20

<210> SEQ ID NO 54
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
cggagatgtt ttgatagcga c                                            21

<210> SEQ ID NO 55
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
tgttttgata gcgacgggaa t                                            21

<210> SEQ ID NO 56
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
tttgatagcg acgggaattt taac                                         24

<210> SEQ ID NO 57
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
gatgttttga tagcgacggg aa                                           22

<210> SEQ ID NO 58
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 58
gctttcggag atgttttg                                                  18

<210> SEQ ID NO 59
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 59
ttcggaattt tgatagcgac g                                              21

<210> SEQ ID NO 60
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60
tcggagattc cttgatagcg a                                              21

<210> SEQ ID NO 61
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
cggagatgtt gcttccttga t                                              21

<210> SEQ ID NO 62
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62
ggagatttcc ttgatagcga cg                                             22

<210> SEQ ID NO 63
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
ttgttggctt tcgattcctt g                                              21

<210> SEQ ID NO 64
<211> LENGTH: 21
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 64
ttgttggctt tcgagacctt g                                                    21

<210> SEQ ID NO 65
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
ttggctttcg gaaccttgat ag                                                   22

<210> SEQ ID NO 66
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
cttgttggct ttcggagact tg                                                   22

<210> SEQ ID NO 67
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
ctttcggagc cttgatagcg                                                      20

<210> SEQ ID NO 68
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
ttgttggctt tcggagtcct t                                                    21

<210> SEQ ID NO 69
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
ctttcgtgtt ccttgatagc ga                                                   22
```

<210> SEQ ID NO 70
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
cggagatacc ttgatagcga cg                                              22

<210> SEQ ID NO 71
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
cggagatgcc ttgatagcga                                                 20

<210> SEQ ID NO 72
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
ttgttggctt tcggagatgt ct                                              22

<210> SEQ ID NO 73
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73
tcggagatat tttgatagcg acg                                             23

<210> SEQ ID NO 74
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
cggagatgtt gcgctccttg                                                 20

<210> SEQ ID NO 75
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

```
<400> SEQUENCE: 75
gctttcggag atgtgctcct                                               20

<210> SEQ ID NO 76
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 76
ggagatgttg gaattttgat agcg                                          24

<210> SEQ ID NO 77
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77
gctttcggag atgttggttc c                                             21

<210> SEQ ID NO 78
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78
ttcggattgt tccttgatag cg                                            22

<210> SEQ ID NO 79
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 79
cggagatgtc cttgatagcg a                                             21

<210> SEQ ID NO 80
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
cggagatgga attttgatag cg                                            22

<210> SEQ ID NO 81
<211> LENGTH: 21
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 81
gctttcggag atggttcctt g                                               21

<210> SEQ ID NO 82
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82
ggctttcgga gatgattcct t                                               21

<210> SEQ ID NO 83
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
gctttcggag aagcaacctt g                                               21
```